US007598355B2

(12) United States Patent
Nicchitta et al.

(10) Patent No.: US 7,598,355 B2
(45) Date of Patent: Oct. 6, 2009

(54) CHARACTERIZATION OF GRP94-LIGAND INTERACTIONS AND PURIFICATION, SCREENING, AND THERAPEUTIC METHODS RELATING THERETO

(75) Inventors: Christopher V. Nicchitta, Durham, NC (US); James J. Wassenberg, Durham, NC (US); Meredith F. N. Rosser, Durham, NC (US); Robyn C. Reed, Durham, NC (US)

(73) Assignee: Duke University, Durham, NC (US)

( * ) Notice: Subject to any disclaimer, the term of this patent is extended or adjusted under 35 U.S.C. 154(b) by 839 days.

(21) Appl. No.: 10/210,333

(22) Filed: Aug. 1, 2002

(65) Prior Publication Data

US 2003/0054996 A1 Mar. 20, 2003

Related U.S. Application Data

(63) Continuation of application No. PCT/US01/09512, filed on Mar. 26, 2001.

(60) Provisional application No. 60/192,118, filed on Mar. 24, 2000.

(51) Int. Cl.
C07K 1/22 (2006.01)
(52) U.S. Cl. .................. 530/413; 530/412; 530/417; 530/415; 530/350
(58) Field of Classification Search .................. 530/350, 530/412, 413, 417, 415
See application file for complete search history.

(56) References Cited

U.S. PATENT DOCUMENTS

| 5,571,840 A | 11/1996 | Mayor et al. ................. 514/567 |
| 5,747,332 A | 5/1998 | Wallen et al. ................ 435/272 |
| 5,801,160 A | 9/1998 | Sandage et al. ............... 514/49 |

FOREIGN PATENT DOCUMENTS

| WO | WO98/12208 | 3/1998 |
| WO | WO99/29182 | 6/1999 |
| WO | WO 01/64834 | 9/2001 |
| WO | 01/94629 A2 | 12/2001 |

OTHER PUBLICATIONS

Sigma Catalog, p. 1581, 1991 edition.*
Hermanson ("Immobilized Affinity Ligand Techniques", Academic Press, 1992, pp. 53-55).*
Peng, J Immunol Meth 204, 13-21, 1997.*
Massa et al., The Stress Gene Response in Brain, *Cerebrovascular and Brain Metabolism Reviews* 8:95-158 (1996).
Csermely et al., The 90-kDa Molecular Chaperone Family: Structure, Function, and Clinical Applications. A Comprehensive Review, *Pharmacol. Ther.* 79, No. 2:129-168 (1998).
Xiao et al., Geldanamycin Provides Posttreatment Protection Against Glutamate-Induced Oxidative Toxicity in a Mouse Hippocampal Cell Line, *J. of Neurochemistry* 72, No. 1:95-101 (1999).
Hearse et al., Experimental Models for the Study of Cardiovascular Function and Disease, *Pharmacological Research* 41, No. 6:598-603 (2000).
Fan et al., Therapeutic approaches for ischemia/reperfusion injury in the liver, *J. Mol Med* 77:577-596 (1999).
Horch et al., Destabilization of Cortical Dendrites and Spines by BDNF, *Neuron* 23:353-364 (Jun. 1999).
McAllister et al., Opposing Roles for Endogenous BDNF and NT-3 in Regulating Cortical Dendritic Growth, *Neuron* 18:767-778 (May 1997).
Chen et al., Stress Proteins and Tolerance to Focal Cerebral Ischemia, *J. of Cerebral Blood Flow and Metabolism* 16:566-577 (1996).
Yagita et al., Molecular Cloning of a Novel Member of the HSP110 Family of Genes, Ischemia-Responsive Protein 94 kDa (irp94), Expressed in Rat Brain After Transient Forebrain Ischemia, *J. of Neurochemistry* 72, No. 4:1544-1551 (1999).
Sciandra et al., Induction of glucose-regulated proteins during anaerobic exposure and of heat-shock proteins after reoxygenation, *Proc. Natl. Acad. Sci. USA* 81:4843-4847 (Aug. 1984).
Kusnetsov et al., Perturbations in maturation of secretory proteins and their association with endoplasmic reticulum chaperones in a cell culture model for epithelial ischemia, *Proc. Natl. Acad. Sci. USA* 93:8584-8589 (Aug. 1999).
International Search Report for PCT/US01/09512.
Obermann et al., In Vivo Function of Hsp90 is Dependent on ATP Binding and ATP Hydrolysis, *J. of Cell Biology* 143, No. 4:901-910 (Nov. 16, 1998).
Pratt, The hsp90-based Chaperone System: Involvement in Signal Transduction from a Variety of Hormone and Growth Factor Receptors, *Journal of the Society for Experimental Biology and Medicine* 127, No. 4:420-434 (Apr. 1998).
Fang et al., Hsp90 Regulates Androgen Receptor Hormone Binding Affinity in Vivo, *J. of Biological Chemistry* 271, No. 45:28697-28702 (1996).
Hutchison et al., Soluble and Membrane-Associated Human Low-Affinity Adenosine Binding Protein (Adenotin): Properties and Homology with Mammalian and Avian Stress Proteins, *Biochemistry* 29:5138-5144 (1990).
Maki et al., Human homologue of murine tumor rejection antigen gp96: 5'-Regulatory and coding regions and relationship to stress-induced proteins, *Proc. Natl. Acad. Sci. USA* 87:5658-5662 (Aug. 1990).
Cala et al., GRP94 Resides within Cardiac Sarcoplasmic Reticulum Vesicles and Is Phosphorylated by Casein Kinase II, *J. of Biological Chemistry* 269(8):5926-5931 (1994).

(Continued)

*Primary Examiner*—David Lukton
(74) *Attorney, Agent, or Firm*—Jenkins, Wilson, Taylor & Hunt, P.A.

(57) ABSTRACT

The present invention discloses characterization of interactions between ligands and Hsp90 proteins, including GRP94, wherein ligand binding to the N-terminal nucleotide binding domain of GRP94 elicits a conformational change that converts the GRP94 from an inactive to an active conformation, and wherein the chaperone and peptide-binding activities of the GRP94 are markedly stimulated. Also disclosed are purification, screening, and therapeutic methods pertaining to the biological activity of GRP94, and in some instances HSP90, based upon the characterization of ligand interactions of Hsp90 peptide-binding proteins, including GRP94.

41 Claims, 17 Drawing Sheets

OTHER PUBLICATIONS

International Search report for PCT/US02/31014.

Wassenberg et al., Ligand Interactions in the Adenosine Nucleotide-binding Domain of theHsp90 Chaperone, GRP94, *J. of Biological Chemistry* 275(30):22806-22814 (Jul. 28, 2000).

Linderoth et al., Identification of the Peptide-Binding Site in the Heat Shock Chaperone/Tumor Rejection Antigen gp96 (Grp94), *J. of Biological Chemistry* 275(8):5472-5477 (Feb. 25, 2000).

Supplementary Partial European Search Report for 01920734.9-2401-US0109512 dated Jun. 1, 2004.

Argon et al. "GRP94, an ER chaperone with protein and peptide binding properties", *Cell & Developmental Biology* 10:495-505 (1999).

Grenert et al., "The Amino-terminal Domain of Heat Shock Protein 90 (hsp90) That Binds Geldanamycin Is an ATP/ADP Switch Domain That Regulates hsp90 Conformation", *The J. of Biological Chemistry* 272(38):23843-23850 (Sep. 19, 1997).

Hutchinson et al., "Soluble and Membrane-Associated Human Low-Affinity Adenosine Binding Protein (Adenotin): Properties and Homology with Mammalian and Avian Stress Proteins" *Biochemistry* 29:5138-5144 (1990).

Srivastava, "Peptide-Binding Heat Shock Proteins in the Endoplasmic Reticulum: Role in Immune Response to Cancer and in Antigen Presentation" *Advances in Cancer Research* 62:153-177 (1993).

Notification of Transmittal of International Preliminary Examination Report for PCT/US02/31014 dated Sep. 28, 2004.

European Office Action corresponding to European patent application No. 1920734.9 dated May 31, 2005.

Communication pursuant to Article 96(2) EPC corresponding to EP Patent Application No. 01920734.9 dated Sep. 12, 2006.

Communication pursuant to Article 96(2) EPC corresponding to European Application No. 01 920 734.9-2401 dated Sep. 14, 2007.

Communication pursuant to Article 94(3) EPC corresponding to European Patent Application No. 01 920 734.9-2401 dated Sep. 11, 2008.

Official Communication corresponding to U.S. Appl. No. 11/821,459 dated Nov. 17, 2008.

\* cited by examiner

SEQUENCE LISTING

```
<160> NUMBER OF SEQ ID NOS: 3

<210> SEQ ID NO 1
<211> LENGTH: 8
<212> TYPE: PRT
<213> ORGANISM: Homo sapiens

<400> SEQUENCE: 1

Arg Gly Tyr Val Tyr Gln Gly Leu
1               5

<210> SEQ ID NO 2
<211> LENGTH: 11
<212> TYPE: PRT
<213> ORGANISM: Homo sapiens

<400> SEQUENCE: 2

Tyr Ser Gln Phe Ile Asn Phe Pro Ile Tyr Val
1               5                   10

<210> SEQ ID NO 3
<211> LENGTH: 13
<212> TYPE: PRT
<213> ORGANISM: Homo sapiens

<400> SEQUENCE: 3

His Ser Gln Phe Ile Gly Tyr Pro Ile Thr Leu Phe Val
1               5                   10
```

CHARACTERIZATION OF GRP94-LIGAND INTERACTIONS AND PURIFICATION, SCREENING, AND THERAPEUTIC METHODS RELATING THERETO

CROSS REFERENCE TO RELATED APPLICATIONS

This application is a continuation of International Application No. PCT/US01/09512 filed Mar. 26, 2001, which is based on and claims priority to U.S. Provisional Application Ser. No. 60/192,118, filed Mar. 24, 2000. Both are herein incorporated by reference in their entirety.

GRANT STATEMENT

This work was supported by NIH grant RO1 DK53058. Thus, the U.S. Government has certain rights in the invention.

TECHNICAL FIELD

The present invention relates to compositions and methods pertaining to the modulation of molecular chaperone function by regulatory ligands. In a preferred embodiment, the present invention relates to the characterization of ligand interactions of GRP94, and purification, screening and therapeutic methods associated therewith.

| Table of Abbreviations | |
|---|---|
| 8-ANS | 1,8-anilinonaphthalenesulfonate |
| APC | antigen presenting cells |
| BiP | ER hsp70 homolog |
| bis-ANS | 4,4'-dianilino-1,1-binaphthyl-5,5-disulfonic acid |
| BMDC | bone marrow-derived dendritic cells |
| BN-PAGE | blue native polyacrylamide gel electrophoresis |
| CEA | carcinoembryonic antigen(s) |
| CT | computed tomographic |
| CTL | cytotoxic T lymphocyte(s) |
| DC | dendritic cells |
| DMEM | Dulbecco's modified Eagle's medium |
| DTH | delayed-type hypersensitivity |
| ER | endoplasmic reticulum |
| GALT | gut-associated lymphoid tissue |
| GRP94 | glucose regulated protein of 94 kDa, ER paralog of the Hsp90 family of chaperones |
| HIV | human immunodeficiency virus |
| HPLC | high pressure liquid chromatography |
| hr | hour(s) |
| hsp(s) | heat shock protein(s) |
| HSP70 | heat shock protein of 70 kDa |
| Hsp90 | any member of the Hsp90 family of chaperones |
| HSP90 | heat shock protein of 90 kDa |
| HSV | herpes simplex virus |
| IFN | interferon |
| Ig | immunoglobulin |
| IGF-1 | insulin-like growth factor |
| IgG | immunoglobulin G |
| IL | interleukin |
| MHC | major histocompatability complex |
| min | minute |
| MLTC | mixed lymphocyte tumor cell assay |
| NECA | N-ethylcarboxamidoadenosine |
| PDI | protein disulfide isomerase |
| PSA | prostate-specific antigen |
| RSV | respiratory syncytial virus |
| RT | room temperature |
| SDS-PAGE | sodium dodecyl sulfate-polyacrylamide gel electrophoresis |
| TAP | transporter associated with antigen presentation complex |
| TFA | trifluoroacetic acid |
| TNF | tumor necrosis factor |

BACKGROUND ART

The pursuit of approaches for treatment and prevention of cancer and infectious diseases represents an ongoing effort in the medical community. Recent efforts to combat cancer and infectious disease have included attempts to induce or enhance immune responses in subjects suffering from a type of cancer or an infectious disease. See, e.g. Srivastava et al. (1998) *Immunity* 8:657-665.

Ischemia/reperfusion injury is a significant source of morbidity and mortality in a number of clinical disorders, including myocardial infarction, cerebrovascular disease, and peripheral vascular disease. In addition, ischemia/reperfusion is relevant to the function of transplanted organs and to the recovery expedience following any cardiovascular surgery. See Fan et al. (1999) *J Mol Med* 77:577-596. Thus, the identification of cellular protective mechanisms against ischemia-induced damage is a central goal for therapy of, for example, heart attacks, strokes, and neurodegenerative diseases, as well as for improvement of recovery following surgery or transplantation.

The Hsp90 class of molecular chaperones are among the most abundant proteins in eukaryotic cells. Hsp90 family members are phylogenetically ubiquitous whereas the endoplasmic reticulum paralog of HSP90, GRP94 (gp96, ERp99, endoplasmin), is found only in higher plants and metazoans (Nicchitta (1998) *Curr Opin Immunol* 10:103-109). The Hsp90 family of proteins are known to be involved in directing the proper folding and trafficking of newly synthesized proteins and in conferring protection to the cell during conditions of heat shock, oxidative stress, nutrient stress, and other physiological stress scenarios (Toft (1998) *Trends Endocrinol Metab* 9:238-243; Pratt (1998) *Proc Soc Exp Biol Med* 217:420-434). Under such stress conditions, protein folding, protein oligomeric assembly, and protein stability can be profoundly disrupted. It is the function of the Hsp90 family of proteins, in concert with other molecular chaperones, to assist in preventing and reversing stress-induced inactivation of protein structure and function.

At a molecular level, HSP90 function in protein folding is known to require the activity of a series of co-chaperones and accessory molecules, including Hsp70, p48Hip, p60Hop, p23, and FKBP52 (Prodromou et al. (1999) *EMBO J* 18:754-762; Johnson et al. (1996) *J Steroid Biochem Mol Biol* 56:31-37; Chang et al. (1997) *Mol Cell Biol* 17:318-325; Duina et al. (1996) *Science* 274:1713-1715; Chen et al. (1996) *Mol Endocrinol* 10:682-693; Smith et al. (1993) *J Biol Chem* 268:18365-18371; Dittmar et al. (1998) *J Biol Chem* 273:7358-7366; Kosano et al. (1998) *J Biol Chem* 273:3273-3279). These co-chaperones and accessory molecules participate in both concerted and sequential interactions with HSP90 and thereby serve to regulate its chaperone activity (Buchner (1999) *Trends Biochem Sci* 24:136-141; Pratt et al. (1996) *Exs* 77:79-95; Pratt (1998) *Proc Soc Exp Biol Med* 217:420-434; Caplan (1999) *Trends Cell Biol* 9:262-268).

In addition to the contribution of co-chaperone proteins to the regulation of HSP90 function, recent crystallographic studies have identified an ATP/ADP binding pocket in the N-terminal domain of yeast and human HSP90, suggesting that HSP90 activity is regulated through cyclic ATP binding and hydrolysis, as has been established for the Hsp70 family of chaperones (Kassenbrock & Kelly (1989) *EMBO J* 8:1461-1467; Flynn et al. (1989) *Science* 245:385-390; Palleros et al. (1991) *Proc Natl Acad Sci USA* 88:519-523; Sriram et al. (1997) *Structure* 5:403-14; Prodromou et al. (1997) *Cell* 90:65-75; Obermann et al. (1998) *J Cell Biol* 143:901-910; Csermely & Kahn (1991) *J Biol Chem* 266:4943-4950;

Csermely et al. (1993) *J Biol Chem* 268:1901-1907; Sullivan et al. (1997) *J Biol Chem* 272:8007-8012; Scheibel et al. (1997) *J Biol Chem* 272:18608-18613; Scheibel et al. (1998) *Proc Natl Acad Sci USA* 95:1495-1499; Panaretou et al. (1998) *EMBO J* 17:4829-4836; Caplan (1999) *Trends Cell Biol* 9:262-268; Grenert et al. (1999) *J Biol Chem* 274:17525-17533).

It has also been reported that HSP90 contains motifs bearing significant similarities to the Walker "A" and "B" sequences associated with ATP binding (Csermely & Kahn (1991) *J Biol Chem* 266:4943-4950; Jakob et al. (1996) *J Biol Chem* 271:10035-10041). Although these sequences are substantially different from the consensus sequences found among serine and tyrosine kinases, they are homologous to the ATP binding sequence seen in the Hsp70 family of proteins (Csermely & Kahn (1991) *J Biol Chem* 266:4943-4950). Consistent with sequence predictions, ATP binding, autophosphorylation activity, and ATPase activity have all been demonstrated for HSP90, though these findings are not without controversy (Csermely & Kahn (1991) *J Biol Chem* 266: 4943-4950; Nadeau et al. (1993) *J Biol Chem* 268:1479-1487, Jakob et al. (1996) *J Biol Chem* 271:10035-10041; Grenert et al. (1999) *J Biol Chem* 274:17525-17533; Scheibel et al. (1997) *J Biol Chem* 272:18608-18613; Prodromou et al. (1997) *Cell* 90:65-75).

In part because of the very low affinity of HSP90 for ATP, a role for ATP in the regulation of HSP90 function remained under question until crystallographic resolution of the N-terminal domain of yeast and human HSP90 in association with bound adenosine nucleotides (Prodromou et al. (1997) *Cell* 90:65-75; Obermann et al. (1998) *J Cell Biol* 143:901-910). Aided by atomic scale structural insights, amino acid residues critical for ATP binding and hydrolysis were subsequently identified and analyzed (Prodromou et al. (1997) *Cell* 90:65-75; Panaretou et al. (1998) *EMBO J* 17:4829-4836; Obermann et al. (1998) *J Cell Biol* 143:901-910). Thus, in the human HSP90, aspartate 93 (D128 for GRP94; D79 for yeast HSP90) provides a direct hydrogen bond interaction with the N6 group of the purine moiety of the adenosine ring and is essential for ATP binding (Prodromou et al. (1997) *Cell* 90:65-75; Obermann et al. (1998) *J Cell Biol* 143:901-910). Glutamate 47 (E82 for GRP94; E33 for yeast HSP90) was postulated to play an important catalytic role in ATP hydrolysis, based both on its location relative to bound nucleotide and through comparison with the ATP binding domain of *E. coli* DNA gyrase B (Prodromou et al. (1997) *Cell* 90:65-75; Obermann et al. (1998) *J Cell Biol* 143:901-910). In subsequent mutagenesis studies of yeast HSP90, it was observed that the D79 mutant was deficient in ATP binding and that E47 mutants were deficient in ATP hydrolysis activity (Obermann et al. (1998) *J Cell Biol* 143:901-910; Panaretou et al. (1998) *EMBO J* 17:4829-4836). As further evidence for a function of these residues in HSP90 activity, yeast containing either mutant form of HSP90 were inviable (Obermann et al. (1998) *J Cell Biol* 143:901-910; Panaretou et al. (1998) *EMBO J* 17:4829-4836).

Progress in the development of Hsp90-based therapeutic and other applications has been impeded by a lack of characterization of ligand interactions of Hsp90 proteins, including GRP94. Despite the above-described characterization of ATP interaction with HSP90, evidence in support of intrinsic ATP binding and ATPase activities with respect to GRP94 is controversial and, as with HSP90, a clear consensus regarding the molecular basis of an adenosine nucleotide-mediated regulation of GRP94-substrate interactions has yet to emerge (Jakob et al. (1996) *J Biol Chem* 271:10035-10041; Wearsch & Nicchitta (1997) *J Biol Chem* 272:5152-5156; Li and Srivastava (1993) *EMBO J* 12:3143-3151; Csermely et al. (1995) *J Biol Chem* 270:6381-6388; Csermely et al. (1998) *Pharmacol Ther* 79:129-168).

What is needed, then, is characterization of ligand interactions at the ligand binding pocket of a HSP90 protein, in particular GRP94 and HSP90. To this end, the present invention discloses methods for assessing ligand-HSP-90 chaperone interactions. Using such methods, the active and inactive structural conformations of GRP94 and HSP90 are herein disclosed, and the regulative capacity of several compounds to induce the active or inactive conformation is also demonstrated. The disclosure herein also provides purification, screening, and therapeutic methods pertaining to the biological activity of Hsp90 proteins. Thus, the present invention meets a long-standing need in the art for methods and compositions that contribute to the understanding, diagnosis and treatment of disorders related to Hsp90 protein function.

SUMMARY OF THE INVENTION

A method for purifying a complex comprising a GRP94 protein is disclosed. The method comprises: (a) contacting a complex comprising a GRP94 protein with a binding agent that preferentially binds GRP94, the binding agent immobilized to a solid phase support, to immobilize the complex to the solid phase support; (b) collecting the remaining sample; and (c) eluting the complex from the solid phase support to give purified complex in the eluate. The present invention also provides a complex obtained by performing the disclosed method.

A method for isolating an antigenic molecule associated with a complex comprising a GRP94 protein is also disclosed. The method comprises: (a) contacting a complex comprising GRP94 and an antigenic molecule with a binding agent that preferentially binds GRP94, the binding agent immobilized to a solid phase support, to immobilize the complex to the solid phase support; (b) collecting the remaining sample; (c) eluting the complex from the solid phase support to give purified complex in the eluate; and isolating the antigenic molecule from the eluate. The present invention also provides an antigenic molecule isolated according to the disclosed method.

A method for detecting a GRP94 complex in a sample suspected of containing a GRP94 complex is also disclosed. The method comprises (a) contacting the sample with a binding agent that preferentially binds GRP94 under conditions favorable to binding a complex comprising GRP94 to the binding substance to form a second complex there between; and (b) detecting the second complex via a label conjugated to the binding substance or via a labeled reagent that specifically binds to the second complex subsequent to its formation.

A kit for detecting, isolating, or purifying a complex comprising a GRP94 protein and an antigenic molecule is also disclosed.

A method of screening a candidate substance for an ability to modulate the biological activity of a Hsp90 protein is also disclosed. The method comprises: (a) establishing a test sample comprising a GRP94 protein and a ligand for a Hsp90 protein; (b) administering a candidate substance to the test sample; and (c) measuring the effect of the candidate substance on binding of a Hsp90 protein and the ligand for a Hsp90 protein in the test sample to thereby determine the ability of the candidate substance to modulate biological activity of a Hsp90 protein. In the method, the Hsp90 protein can comprise a GRP94 protein and the ligand can comprise bis-ANS.

Further disclosed is a method for identifying a candidate substance as an activator of the biological activity of a Hsp90 protein. The method comprises: (a) establishing a test sample comprising a Hsp90 protein and a candidate substance, (b) administering 8-ANS to the test sample, (c) detecting a fluorescence signal produced by the 8-ANS, and (d) identifying the candidate substance as an activator of the biological activity of a Hsp90 protein based upon an amount of fluorescence signal produced by the 8-ANS as compared to a control sample. Preferably, the Hsp90 protein comprises GRP94 or HSP90.

A method is also provided for identifying a candidate substance as an inhibitor of the biological activity of a Hsp90 protein. The method comprises: (a) establishing a test sample to induce a conformational change to the Hsp90 protein, (b) heat-shocking the test sample to induce a conformational change to the Hsp90 protein, (c) administering 8-ANS to the test sample, (d) detecting a fluorescence signal produced by binding of 8-ANS to the Hsp90, and (e) identifying the candidate substance as an inhibitor of the biological activity of a Hsp90 protein based upon an amount of fluorescence signal produced by the 8-ANS as compared to a control sample. Preferably, the Hsp90 protein comprises GRP94 or HSP90.

A method of modulating biological activity of a Hsp90 protein is also disclosed. The method comprises contacting an Hsp90 protein with an effective amount of a Hsp90 protein activity-modulating substance to thereby modulate the biological activity of the Hsp90 protein. Preferably, the Hsp90 protein is GRP94 or HSP90. A pharmaceutical composition comprising a therapeutically effective amount of a modulator of a biological activity of a Hsp90 protein, and a pharmaceutically acceptable diluent or vehicle, is also disclosed. Preferably, the Hsp90 protein is GRP94 or HSP90.

A method of treating a subject suffering from a disorder wherein modulation of the biological activity of a Hsp90 protein is desirable is also disclosed. The method comprises administering to the subject an effective amount of a Hsp90 protein activity modulator, whereby modulation of the biological activity of a Hsp90 protein in the subject is accomplished. Preferably, the Hsp90 protein is GRP94 or HSP90. Hsp90 biological activity (in a preferred embodiment—GRP94 biological activity) that is modulated can comprise immunogenicity, protein transport from the endoplasmic reticulum, recovery from stress and tissue injury arising from, for example, hypoxia/anoxia, nutrient deprivation, or heat stress, or combinations thereof. The disorder to be treated can comprise a type of cancer; an infectious disease; a disorder associated with impaired protein transport from the endoplasmic reticulum; a disease state, such as cancer, wherein it would be of therapeutic benefit to inhibit or block the egress of proteins (e.g., growth factor receptors) from the endoplasmic reticulum; a disorder associated with ischemia; or combinations thereof. The method can further comprise administering to the subject a composition comprising a therapeutically or prophylactically effective amount of a purified complex, said complex comprising a Hsp90 protein bound to an antigenic molecule specific to said disorder.

A method for preparing an immunogenic composition for inducing an immune response in a vertebrate subject is also disclosed. The method comprises: (a) harvesting from a eukaryotic cell an immunogenic complex comprising an Hsp90 protein non-covalently bound to an antigenic molecule, said complex, when administered to said vertebrate subject being operative at initiating an immune response in said vertebrate subject, wherein said eukaryotic cell has been treated with an activating ligand; and (b) combining said complex with pharmaceutically acceptable carrier. Preferably, the Hsp90 protein is GRP94 or HSP90. The ligand can comprise bis-ANS.

A method for preparing an immunogenic composition for inducing an immune response in a vertebrate subject is also disclosed. The method comprises: (a) reconstituting in vitro an antigenic molecule and an Hsp90 protein molecule in the presence of a Hsp90 activating ligand to thereby produce an immunogenic complex comprising a Hsp90 protein non-covalently bound to an antigenic molecule, said complex, when administered to said vertebrate subject being operative at initiating an immune response in said vertebrate subject; and (b) combining said complex with pharmaceutically acceptable carrier. Preferably, the Hsp90 protein is GRP94 or HSP90, and the ligand comprises bis-ANS.

A method for preparing an immunogenic composition for inducing an immune response in a vertebrate subject is also disclosed. The method comprises: (a) sensitizing antigen presenting cells in vitro with a complex comprising a Hsp90 protein non-covalently bound to an antigenic molecule and with an activating ligand; and (b) combining said at least one sensitized antigen presenting cell with pharmaceutically acceptable carrier. Preferably, the Hsp90 protein is GRP94 or HSP90, and the ligand comprises bis-ANS.

Accordingly, it is an object of the present invention to provide novel purification methods, novel screening methods, and novel therapeutic methods pertaining to the biological activity of GRP94 and other Hsp90 proteins. The object is achieved in whole or in part by the present invention.

An object of the invention having been stated hereinabove, other objects will become evident as the description proceeds when taken in connection with the accompanying Drawings and Laboratory Examples as best described herein below.

DETAILED DESCRIPTION OF THE INVENTION

Figure 1A:
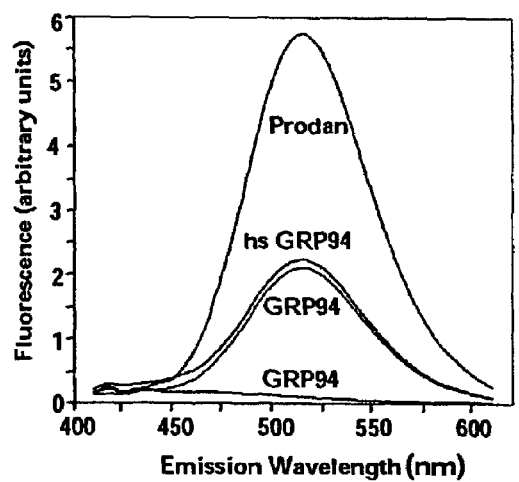
FIG. 1A is a graph depicting Prodan binding to GRP94 independent of GRP94 structural state. Fluorescence emission wavelength scans of 0.5 μM native or heat shocked (hs) GRP94 were performed following exposure to 5 μM Prodan for 30 minutes. Values represent the maximal fluorescence relative to that occurring with an identical concentration of heat shocked GRP94. Experiments were conducted at excitation wavelengths of 360 nm (Prodan). All spectra were background corrected.

Disclosed herein is the characterization of ligand interactions of GRP94, and where applicable Hsp90, wherein ligand binding to the N-terminal nucleotide binding domain of GRP94, and in some instances, Hsp90, elicits a conformational change that converts GRP94, and in some instances, Hsp90, from an inactive to an active conformation, and wherein the chaperone and peptide binding activities of GRP94, and where applicable, Hsp90, are markedly stimulated. Also disclosed herein is the characterization of ligand interactions of GRP94, and where applicable Hsp90, wherein ligand binding to the N-terminal nucleotide binding domain of GRP94, and in some instances, Hsp90, inhibits a conformational change that converts GRP94, and in some instances, Hsp90, from an inactive to an active conformation, and wherein the activities of GRP94, and where applicable, Hsp90, are markedly inhibited. Also disclosed herein are ligands, and methods of screening for such ligands, that bind to the N-terminal nucleotide binding domain and inhibit protein activity and/or protein conformational activation in a manner similar and/or related to that observed with geldanamycin and radicicol. Such ligands can function as potential anti-tumor therapeutics. Also disclosed herein are purification, screening, and therapeutic methods pertaining to the biological activity of GRP94, and in some instances Hsp90, based upon the characterization of ligand interactions of GRP94, and in some instances Hsp90.

A. Definitions

While the following terms are believed to have well defined meanings in the art, the following definitions are set forth to facilitate explanation of the invention.

"Antigenic molecule" as used herein refers to the peptides with which GRP94 or HSP90 endogenously associates in vivo (e.g., in infected cells or precancerous or cancerous tissue) as well as exogenous antigens/immunogens (i.e., not complexed with GRP94 or HSP90 in vivo) or antigenic/immunogenic fragments and derivatives thereof.

The term "biological activity" is meant to refer to a molecule having a biological or physiological effect in a subject. Adjuvant activity is an example of a biological activity. Activating or inducing production of other biological molecules having adjuvant activity is also a contemplated biological activity.

The term "adjuvant activity" is meant to refer to a molecule having the ability to enhance or otherwise modulate the response of a vertebrate subject's immune system to an antigen.

The term "immune system" includes all the cells, tissues, systems, structures and processes, including non-specific and specific categories, that provide a defense against antigenic molecules, including potential pathogens, in a vertebrate subject. As is well known in the art, the non-specific immune system includes phagocytic cells such as neutrophils, monocytes, tissue macrophages, Kupffer cells, alveolar macrophages, dendritic cells and microglia. The specific immune system refers to the cells and other structures that impart specific immunity within a host. Included among these cells are the lymphocytes, particularly the B cell lymphocytes and the T cell lymphocytes. These cells also include natural killer (NK) cells. Additionally, antibody-producing cells, like B lymphocytes, and the antibodies produced by the antibody-producing cells are also included within the term "immune system".

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

The term "systemic immune response" is meant to refer to an immune response in the lymph node-, spleen-, or gut-associated lymphoid tissues wherein cells, such as B lymphocytes, of the immune system are developed. For example, a systemic immune response can comprise the production of serum IgG's. Further, systemic immune response refers to antigen-specific antibodies circulating in the blood stream and antigen-specific cells in lymphoid tissue in systemic compartments such as the spleen and lymph nodes.

The terms "humoral immunity" or "humoral immune response" are meant to refer to the form of acquired immunity in which antibody molecules are secreted in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response also comprises lymphocyte proliferation. When "lymphocyte proliferation" is measured, the ability of lymphocytes to proliferate in response to specific antigen is measured. Lymphocyte proliferation is meant to refer to B cell, T-helper cell or CTL cell proliferation.

The term "CTL response" is meant to refer to the ability of an antigen-specific cell to lyse and kill a cell expressing the specific antigen. As described herein below, standard, art-recognized CTL assays are performed to measure CTL activity.

"Adoptive immunotherapy" as used herein refers to a therapeutic approach with particular applicability to cancer whereby immune cells with an antitumor reactivity are administered to a tumor-bearing host, with the aim that the cells mediate either directly or indirectly, the regression of an established tumor.

An "immunogenic composition" is meant to refer to a composition that can elicit an immune response. A vaccine is contemplated to fall within the meaning of the term "immunogenic composition", in accordance with the present invention.

The term "a biological response modifier" is meant to refer to a molecule having the ability to enhance or otherwise modulate a subject's response to a particular stimulus, such as presentation of an antigen.

As used herein, the terms "candidate substance" and "candidate compound" are used interchangeably and refer to a substance that is believed to interact with another moiety as a biological response modifier. For example, a representative candidate compound is believed to interact with a complete, Hsp90 protein, or fragment thereof, and which can be subsequently evaluated for such an interaction. Exemplary candidate compounds that can be investigated using the methods of the present invention include, but are not restricted to, agonists and antagonists of a Hsp90 protein, viral epitopes, peptides, enzymes, enzyme substrates, co-factors, lectins, sugars, oligonucleotides or nucleic acids, oligosaccharides, proteins, chemical compounds small molecules, and monoclonal antibodies.

As used herein, the term "modulate" means an increase, decrease, or other alteration of any or all chemical and biological activities or properties of a wild-type or mutant Hsp90 protein, preferably a wild-type or mutant GRP94 or HSP90 polypeptide. The term "modulation" as used herein refers to both upregulation (i.e., activation or stimulation) and downregulation (i.e. inhibition or suppression) of a response.

As used herein, the term "agonist" means an agent that supplements or potentiates the biological activity of a functional Hsp90 protein.

As used herein, the term "antagonist" means an agent that decreases or inhibits the biological activity of a functional Hsp90 protein, or that supplements or potentiates the biological activity of a naturally occurring or engineered non-functional Hsp90 protein.

B. General Considerations

As used herein the term "Hsp90 protein" is meant to refer to any of the Hsp90 class of molecular chaperones that are among the most abundant proteins in eukaryotic cells, and to biologically active fragments of such proteins. The term "HSP90 protein" refers to an individual member of this class, exemplified by canine HSP90 (GenBank Accession No. U01153) and mouse HSP90 (SwissProt Accession No. P08113), and to biologically active fragments thereof. Hsp90 family members are phylogenetically ubiquitous whereas the endoplasmic reticulum paralog of HSP90, GRP94 (gp96, ERp99, endoplasmin) is found only in higher plants and metazoans (Nicchitta (1998) *Curr Opin Immunol* 10:103-109). The Hsp90 family of proteins are involved in directing the proper folding and trafficking of newly synthesized proteins and in conferring protection to the cell during conditions of heat shock, oxidative stress, hypoxic/anoxic conditions, nutrient deprivation, other physiological stresses, and disorders or traumas that promote such stress conditions such as, for example, stroke and myocardial infarction.

As used herein, the terms "binding pocket of the Hsp90 protein", "Hsp90 binding pocket", "GRP94 binding pocket", and "HSP90 binding pocket" are used interchangeably and mean that region of a Hsp90 protein, preferably a GRP94 polypeptide or a HSP90 polypeptide, where a ligand binds.

Even more preferably, the GRP94 binding pocket comprises amino acid residues 22-337 of GRP94.

As noted above, GRP94 (gp96, ERp99, endoplasmin) is the endoplasmic reticulum paralog of cytosolic HSP90, and as such, is an abundant resident ER lumenal protein that by virtue of its association with nascent polypeptides performs a chaperone function. The term "GRP94" and/or "GRP94 protein" also refers to biologically active fragments of a GRP94 protein. Consistent with this role, GRP94 expression is upregulated by stress conditions that promote protein misfolding or unfolding, such as glucose starvation, oxidative stress, and heavy metal poisoning. In addition to its role in the regulation of protein folding in the ER, GRP94 can function in the intercellular trafficking of peptides from the extracellular space to the major histocompatability complex (MHC) class I antigen processing pathway of professional antigen presenting cells. Thus, in addition to a homeostatic role in protein folding and assembly, GRP94 functions as a component of the MHC class I antigen processing and presentation pathways of mammalian cells.

GRP94 also contributes to the folding and assembly of immunoglobulins, MHC class II molecules, HSV-1 glycoproteins, thyroglobulin, collagen, and p185erbB2. (Melnick et al. (1992) *J Biol Chem* 267:21303-21306; Melnick et al. (1994) *Nature* 370:373-375; Schaiff et al. (1992) *J Exp Med* 176: 657-666; Navarro et al. (1991) *Virology* 184:253-264; Kuznetsov et al. (1994) *J Biol Chem* 269:22990-22995; Ferreira et al. (1994) *J Cell Biochem* 56:518-26; Chavany et al. (1996) *J Biol Chem* 273:4974-4977). In addition to interactions with polypeptide folding substrates, GRP94 binds peptides, a subset of which is suitable for assembly on nascent MHC class I molecules. (Srivastava et al. (1986) *Proc Natl Acad Sci USA* 83:3407-3411; Nieland et al. (1996) *Proc Natl Acad Sci USA* 93:6135-6139; Wearsch & Nicchitta (1997) *J Biol Chem* 272: 5152-5156; Ishii et al. (1999) *J Immunol* 162:1303-1309; Srivastava et al. (1998) *Immunity* 8:657-665; Sastry & Linderoth (1999) *J Biol Chem* 274:12023-12035). The peptide binding activity of GRP94 plays a role in its ability to elicit $CD8^+$ T cell immune responses. (Udono et al. (1994) *Proc Natl Acad Sci USA*, 91:3077-30781; Suto & Srivastava (1995) *Science* 269:1585-1588; Arnold et al. (1995) *J Exp Med* 182: 885-889; Nair et al. (1999) *J Immunol* 162:6426-6432; Blachere et al. (1997) *J Exp Med* 186:465-472; Heike et al. (1996) *J Leukoc Biol* 139:613-623; Srivastava et al. (1998) *Immunity* 8:657-665). Peptide binding activity is not, however, alone sufficient to impart immunogenic activity to a protein and thus GRP94 is among a limited subset of molecular chaperones that can function in the essential immunological process of cross-presentation. (Srivastava et al. (1998) *Immunity* 8:657-665; Nair et al. (1999) *J Immunol* 162:6426-6432; Basu and Srivastava (1999) *J Exp Med* 189:797-802; Schild et al. (1999) *Curr Opin Immunol* 11:109-113).

HSP90 has adenosine nucleotide-dependent modes of regulation. Additionally, amino acid side chains that participate in water-mediated hydrogen bonds with the N7 group of the purine ring of adenosine (N51 in human HSP90=N86 in GRP94) and the N1 group of the purine ring of adenosine (G97 in human HSP90=G130 of GRP94) are conserved between HSP90 and GRP94. The N6 group of the purine ring of adenosine (L48 in human HSP90=L83 in GRP94) that mediates direct nucleotide binding is also conserved between HSP90 and GRP94. In ATP binding with HSP90, the N6 group of the adenine purine is the sole direct hydrogen bond between the nucleotide and the nucleotide binding pocket (Prodromou et al. (1997) *Cell* 90:65-75; Obermann et al. (1998) *J Cell Biol* 143:901-910), and N6 substituted adenosine analogs do not bind to GRP94. (Hutchison & Fox (1989)

J Biol Chem 264:19898-903; Hutchison et al. (1990) *Biochemistry* 29:5138-5144). Thus, although ATP/ADP binding and hydrolysis are generally accepted as biological properties of HSP90, it is not known whether ATP/ADP serve an identical function(s) in the regulation of GRP94 activity. ATP and ADP bind with very low affinity to GRP94 and thus experimental limitations require that ATP/ADP interactions at the GRP94 nucleotide binding pocket be analyzed by indirect methods, including but not limited to ligand displacement assays. (Wearsch et al. (1998) *Biochemistry* 37(16):5709-5719; Csermely et al. (1995) *J Biol Chem* 270:6381-6388; Li & Srivastava (1993) *EMBO J* 12:3143-3151).

The peptide binding activity of GRP94 plays a role in its ability to elicit $CD8^+$ T cell immune responses. Peptide binding activity is not, however, alone sufficient to impart immunogenic activity to a protein and thus GRP94 is among a limited subset of molecular chaperones that can function in the essential immunological process of cross-presentation. Until the disclosure of the present invention, a GRP94 ligand-interaction that modulates activity of GRP94 with respect to both polypeptide and peptide substrates remained to be determined.

HSP90 and GRP94 have been proposed as possible targets of several antitumor agents, principally radicicol and geldanamycin. Scheibel & Buckner (1998) *Biochem Pharm* 56:675-82. These compounds are believed to act by inhibiting the ability of the Hsp90 proteins to assist proto-oncogenic kinases, hormone receptors, and other signaling proteins assume their active folded states and appropriate subcellular location. Pratt (1998) *Proc Soc Exp Biol Med* 217:420-434.

GRP94 has also been found to elicit cytotoxic T cell responses, a reflection of its peptide binding activity (Nicchitta (1998) *Curr Opin Immunol* 10:103-109; Srivastava et al. (1998) *Immunity* 8:657-665). It is now established that GRP94-peptide complexes can be processed by professional antigen presenting cells, with the GRP94-bound peptides exchanged onto MHC class I molecules of the antigen presenting cell. The antigen presenting cells can then interact with naive $CD8^+$ T cell responses against tissue(s) displaying peptide epitopes present in complex with GRP94 (Srivastava et al. (1998) *Immunity* 8:657-665).

A potential yet heretofore uncharacterized protective role of grp94 in inschemia is supported by the observation that expression of GRP94 is enhanced in hippocampus after transient forebrain ischemia of a duration known to result in neuronal death (Yagita et al. (1999) *J Neurochem* 72:1544-1551). grp94 is similarly induced following acute kidney ischemia (Kuznetsov (1996) *Proc Natl Acad Sci USA* 93:8584-8589). Heat-shock proteins, including HSP90, are overexpressed during the oxidative stress of reperfusion that generally follows ischemia (Sciandra et al. (1984) *Proc Natl Acad Sci USA* 81:4843-4847). HSP90 might also play a role in ischemic signaling by binding to the hypoxia-inducible factor 1-a (Gradin et al. (1996) *Mol Cell Biol* 16:5221-5231).

Summarily, in accordance with the present invention, GRP94 and HSP90 represent rational targets for chemotherapeutics, immunotherapeutics and vaccines relevant to the treatment of infections disease and cancer. In view of their function as molecular chaperones, GRP94 and HSP90 further represent rational targets for the development of therapeutics for tissue injury and stress, such as may occur in ischemic injuries including, but not limited to, organ (kidney, heart, lung, liver) transplantation, cerebral stroke, and myocardial infarct. Furthermore, Hsp90 and GRP94 represent rational targets for anti-tumor drug design.

C. Ligand Compositions

In one embodiment the present invention pertains to a composition of matter that acts as a ligand for GRP94. The ligand can comprise a purified and isolated natural ligand for GRP94, or can comprise a synthetic compound, such as are identified by the screening and rational drug design techniques disclosed herein. Preferably, the ligand is a small molecule mimetic. More preferably, the ligand has activity in the modulation of GRP94 biological activity. Thus, ligands having such activity are also referred to herein as "modulators". Representative ligand compositions are preferably about 500-1000 daltons, polycyclic molecules that can show structural resemblance to radicicol, geldanamycin, or adenosine derivatives. Optionally, a ligand is hydrophobic.

A representative ligand or modulator composition of matter comprises an adenosine moiety or structural mimetic thereof having any of a variety of substitutions at the 2', 3', and 5' positions, in the case of adenosine, as deemed appropriate by high resolution structural analyses of ligand-GRP94 interactions. Optionally, 5' position alkyl extensions can be included, preferably as a carboxamido linkage to the parent adenosine and, to facilitate stable chemical linkage to a solid support for the purposes of affinity-based purification, terminating in any of a subset of chemically reactive groups including, but not limited to vinyl, maleimide and/or succinimide esters, or substituents suitable for chemical coupling to solid phase supports, such as amino or sulphydryl groups. The composition acts as a ligand for GRP94 and has application in the purification, screening and therapeutic methods disclosed herein.

Additional ligands can be identified through combinatorial chemistry of a parent precursor molecule bearing a hydrogen bond mimetic, preferably corresponding to the ribose of adenosine, and a benzimidazole or structurally related scaffold, corresponding to the adenine base of adenosine.

A representative ligand or modulator composition comprises a compound of the formula (I):

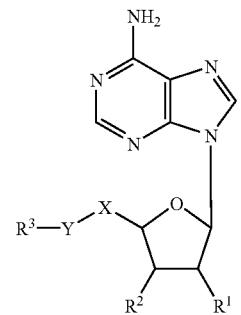

where:

X and Y are the same or different and X and Y=C, N, O or S; and X and Y can be substituted with hydrogen, hydroxyl, or oxygen, including double-bonded oxygen;

$R^1$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arlyester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^1$ is halo where halo is chloro, fluoro, bromo, or iodo;

$R^2$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^2$ is halo where halo is chloro, fluoro, bromo, or iodo; and $R^3$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^3$ is halo where halo is chloro, fluoro, bromo, or iodo.

Where the ligand composition further comprises a compound of the formula (II):

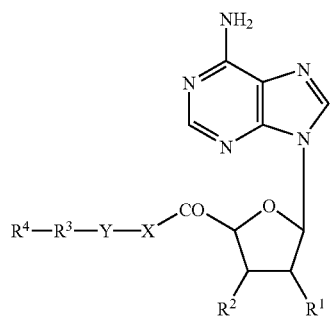

where:

X and Y are the same or different and X and Y=C, N, O or S; and X and Y can be substituted with hydrogen, hydroxyl, or oxygen, including double-bonded oxygen;

$R^1$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^1$ is halo where halo is chloro, fluoro, bromo, or iodo;

$R^2$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^2$ is halo where halo is chloro, fluoro, bromo, or iodo;

$R^3$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^3$ is halo where halo is chloro, fluoro, bromo, or iodo; and $R^4$=$C_1$ to $C_6$ alkyl, $C_1$ to $C_6$ branched alkyl, $C_4$ to $C_8$ cycloalkyl with or without O, N or S in the ring, $C_1$ to $C_6$ alkenyl, branched $C_1$ to $C_6$ alkenyl, $C_4$ to $C_8$ cycloalkenyl with or without O, N or S in the ring, $C_4$ to $C_8$ aroyl, $C_4$ to $C_8$ aryl, $C_4$ to $C_{12}$ heterocyclic or heteropolycyclic alkyl or aryl with O, N or S in the ring, $C_4$ to $C_8$ aryl-substituted $C_1$ to $C_6$ alkyl, alkyl-substituted or aryl-substituted $C_4$ to $C_{12}$ heterocyclic or heteropolycyclic alkyl or aryl with O, N or S in the ring, alkyl-substituted $C_4$ to $C_8$ aroyl, or alkyl-substituted $C_4$ to $C_8$ aryl; or hydroxyl-, amino-, or halo-substituted versions thereof where halo is chloro, bromo, fluoro or iodo.

D. Purification Methods

In accordance with the present invention, a method for purifying a complex comprising GRP94, or in some instances HSP90, by affinity chromatography is provided. The complex preferably comprises GRP94 bound to an antigenic molecule. More preferably, the complex comprises GRP94 non-covalently bound to an antigenic molecule. In one embodiment, the method comprises contacting a sample comprising a GRP94 complex with a binding agent that preferentially binds GRP94, the binding agent immobilized to a solid phase support, to immobilize the complex to the solid phase support; collecting the remaining sample; and eluting the GRP94 complex from the solid phase support to give purified GRP94 complex in the eluate. By the phrase "a binding agent that preferentially binds GRP94" it is meant an agent that preferentially binds GRP94 as compared to other molecular entities, including but not limited to other heat shock proteins.

The binding agent preferably comprises an adenosine moiety or structural mimetic thereof having any of a variety of substitutions at the 2', 3', and 5' positions, in the case of adenosine, as deemed appropriate by high resolution structural analyses of ligand-GRP94 interactions. Optionally, 5' position alkyl extensions can be included, preferably as a carboxamido linkage to the parent adenosine and, to facilitate stable chemical linkage to a solid support for the purposes of affinity-based purification, terminating in any of a subset of chemically reactive groups including, but not limited to vinyl, maleimide and/or succinimide esters, or substituents suitable for chemical coupling to solid phase supports, such as amino or sulphydryl groups. More preferably, the binding agent is free of ATP or ADP. A representative binding agent comprises a compound of the formula (I) or a compound of formula (II). Another representative binding agent comprises N-ethylcarboxamidoadenosine (NECA). Additional ligands can be identified through combinatorial chemistry of a parent precursor molecule bearing a hydrogen bond mimetic, preferably corresponding to the ribose of adenosine, and a benzimidazole or structurally related scaffold, corresponding to the adenine base of adenosine.

Optionally, the complex bound to the immobilized binding agent is eluted by washing the solid phase support with a buffer comprising a physiological salts solution containing appropriate concentrations of the parent ligand (i.e., the binding agent) to give complex in the eluate. Hence, a complex further comprising the binding agent or eluting ligand is also provided in accordance with the present invention. The eluting ligand will then be removed from the eluate solution by dialysis in buffers appropriate for GMP production including, but not limited to, physiological salts and volatile salts.

The affinity methods disclosed herein above can be used to isolate GRP94-peptide complexes or GRP94 alone, or in some instances, HSP90-peptide complexes, or the HSP90 protein alone, from any eukaryotic cell. For example, tissues, isolated cells, or immortalized eukaryote cell lines infected with a preselected intracellular pathogen, tumor cells or tumor cell lines can be used. The complex can also be obtained from a vertebrate subject, such as a warm-blooded vertebrate, including mammals and bird. Optionally, the mammal includes, but is not limited to, human, mouse, pig, rat, ape, monkey, cat, guinea pig, cow, goat and horse.

In one embodiment, the complex is "autologous" to the vertebrate subject; that is, the complex is isolated from either from the infected cells or the cancer cells or precancerous cells of the vertebrate subject (e.g., preferably prepared from infected tissues or tumor biopsies of a vertebrate subject).

Alternatively, the complex is produced in vitro (e.g., wherein a complex with an exogenous antigenic molecule is desired). Alternatively, GRP94 and/or the antigenic molecule can be isolated from a particular vertebrate subject, or from others, or by recombinant production methods using a cloned GRP94 originally derived from a particular vertebrate subject or from others. Exogenous antigens and fragments and derivatives (both peptide and non-peptide) thereof for use in complexing with GRP94 (or in some instances HSP90), can be selected from among those known in the art, as well as those readily identified by standard immunoassays know in the art by the ability to bind antibody or MHC molecules (antigenicity) or generate immune response (immunogenicity). Complexes of GRP94 and antigenic molecules can be isolated from cancer or precancerous tissue of a subject, or from a cancer cell line, or can be produced in vitro (as is necessary in the embodiment in which an exogenous antigen is used as the antigenic molecule).

D.1. Isolation of Antigenic/Immunogenic Components

A method for isolating or purifying an antigenic molecule associated with a complex comprising GRP94, or in some instances HSP90, is also provided in accordance with the present invention. In one embodiment, the method comprises: contacting a sample comprising a complex comprising an antigenic molecule and GRP94 with a binding agent that preferentially binds GRP94, the binding agent immobilized to a solid phase support, to immobilize the complex to the solid phase support; collecting the remaining sample; eluting the complex from the solid phase support to give purified complex in the eluate; and isolating the antigenic molecule from the eluate.

The binding agent preferably comprises an adenosine moiety or structural mimetic thereof having any of a variety of substitutions at the 2', 3', and 5' positions, in the case of adenosine, as deemed appropriate by high resolution structural analyses of ligand-GRP94 interactions. Optionally, 5' position alkyl extensions can be included, preferably as a carboxamido linkage to the parent adenosine and, to facilitate stable chemical linkage to a solid support for the purposes of affinity-based purification, terminating in any of a subset of chemically reactive groups including, but not limited to vinyl, maleimide and/or succinimide esters, or substituents suitable for chemical coupling to solid phase supports, such as amino or sulphydryl groups. More preferably, the binding agent is free of ATP or ADP. A representative binding agent comprises a compound of formula (I) or a compound of formula (II). Another representative binding agent comprises N-ethylcarboxamidoadenosine (NECA). Additional ligands can be identified through combinatorial chemistry of a parent precursor molecule bearing a hydrogen bond mimetic, preferably corresponding to the ribose of adenosine, and a benzimidazole or structurally related scaffold, corresponding to the adenine base of adenosine.

Optionally, the complex bound to the immobilized binding agent is eluted by washing the solid phase support with a buffer comprising a physiological salts solution containing appropriate concentrations of the parent ligand (i.e. the binding agent) to give complex in the eluate. Hence, a complex further comprising the binding agent or eluting ligand is also provided in accordance with the present invention. The eluting ligand will then be removed from the eluate solution by dialysis in buffers appropriate for GMP production including, but not limited to, physiological salts and volatile salts.

It has been found that antigenic peptides and/or components can be eluted from GRP94-complexes under low pH conditions. These experimental conditions can be used to isolate peptides and/or antigenic components from cells which can contain potentially useful antigenic determinants. Once isolated, the amino acid sequence of each antigenic peptide can be determined using conventional amino acid sequencing methodologies. Such antigenic molecules can then be produced by chemical synthesis or recombinant methods; purified; and complexed to GRP94, or alternatively HSP90, in vitro. Additionally, antigenic peptide sequences can be obtained by mass spectrometry using, but not limited to, electrospray and MALDI-TOF instrumentation, coupled with quadrapole detection and CAD-based sequencing.

D.2. Elution of Peptides From GRP94-Peptide Complexes

Several methods can be used to elute a peptide from a GRP94-peptide complex or from a HSP90-peptide complex. The approaches involve incubating the complex in a low pH buffer and/or in guanidinium/HCl (3-6 M), 0.1-1% TFA or acetic acid. Briefly, the complex of interest is centrifuged through a CENTRICON®10 assembly (Amicon of Beverly, Mass.) to remove any low molecular weight material loosely associated with the complex. The large molecular weight fraction can be removed and analyzed by SDS-PAGE while the low molecular weight material is fractionated by capillary and/or nanoscale HPLC, with a flow rate of 0.5 mL/min, with monitoring at 210/220 nm.

In the low pH protocol, acetic acid or trifluoroacetic acid (TFA) is added to the complex to give a final concentration of 10% (vol/vol) and the mixture incubated at room temperature or other suitable temperature, for 10 minutes (Van Bleek et al. (1990) *Nature* 348:213-216; Li et al. (1993) *EMBO J* 12:3143-3151).

The resulting samples are centrifuged through a CENTRICON®10 assembly as mentioned previously. The high and low molecular weight fractions are recovered. The remaining large molecular weight complexes can be reincubated with guanidinium or low pH to remove any remaining peptides. The resulting lower molecular weight fractions are pooled, concentrated by evaporation and dissolved in 0.1% trifluoroacetic acid (TFA). The dissolved material is fractionated by microbore HPLC, with a flow rate of 0.5 ml/min. The elution of the peptides can be monitored by OD210/220nm and the fractions containing the peptides collected.

D.3. Sequencing and Synthesis of Peptides

The amino acid sequences of the eluted peptides can be determined either by manual or automated amino acid sequencing techniques well known in the art. Once the amino acid sequence of a potentially protective peptide has been determined the peptide can be synthesized in any desired amount using conventional peptide synthesis or other protocols well known in the art.

A subject peptide can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. Many techniques for peptide synthesis are available and can be found in Steward et al. (1969) *Solid Phase Peptide Synthesis*, W. H. Freeman Co., San Francisco, Calif.; Bodanszky, et al. (1976) *Peptide Synthesis*, John Wiley & Sons, Second Edition; Meienhofer (1983) *Hormonal Proteins and Peptides*, Vol. 2, p. 46, Academic Press, New York, N.Y.; Merrifield (1969) *Adv Enzymol* 32:221-296; Fields et al. (1990) *Int J Peptide Protein Res* 35:161-214; and U.S. Pat. No. 4,244,946 for solid phase peptide synthesis; and Schroder et al. (1965) *The Peptides*, Vol. 1, Academic Press, New York, N.Y. for classical solution synthesis, each of which is incorporated herein by reference. Appropriate protective groups usable in such synthesis are described in the above texts and in McOmie (1973) *Protective Groups in Organic Chemistry*, Plenum Press, New York, N.Y., which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above can be reacted to form their corresponding cyclic peptides. An exemplary method for cyclizing peptides is described by Zimmer et al. (1993) *Peptides*, pp. 393-394, ESCOM Science Publishers, B. V. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

Purification of the resulting peptides is accomplished using conventional procedures, such as preparative HPLC using gel permeation, partition and/or ion exchange chromatography. The choice of appropriate matrices and buffers are well known in the art and so are not described in detail herein.

D.4. Detection Methods

A method for detecting a complex comprising GRP94, or in some instances HSP90, in a sample suspected of containing such a complex is also provided in accordance with the present invention. In one embodiment, the method comprises: contacting the sample with a binding substance that preferentially binds GRP94 under conditions favorable to binding a complex comprising GRP94 to the binding substance to form a second complex there between; and detecting the second complex via a label conjugated to the binding substance or via a labeled reagent that specifically binds to the second complex subsequent to its formation.

The binding substance preferably comprises an adenosine moiety or structural mimetic thereof having any of a variety of substitutions at the 2', 3', and 5' positions, in the case of adenosine, as deemed appropriate by high resolution structural analyses of ligand-GRP94 interactions. Optionally, 5' position alkyl extensions can be included, preferably as a carboxamido linkage to the parent adenosine and, to facilitate stable chemical linkage to a solid support for the purposes of affinity-based purification, terminating in any of a subset of chemically reactive groups including, but not limited to vinyl, maleimide and/or succinimide esters, or substituents suitable for chemical coupling to solid phase supports, such as amino or sulphydryl groups. More preferably, the binding substance is free of ATP or ADP. A representative binding substance comprises a compound of formula (I) or a compound of formula (II). Another representative binding substance comprises N-ethylcarboxamidoadenosine (NECA). Additional ligands can be identified through combinatorial chemistry of a parent precursor molecule bearing a hydrogen bond mimetic, preferably corresponding to the ribose of adenosine, and a benzimidazole or structurally related scaffold, corresponding to the adenine base of adenosine.

Optionally, the complex bound to the immobilized binding agent is eluted by washing the solid phase support with a buffer comprising a physiological salts solution containing appropriate concentrations of the parent ligand (i.e. the binding substance or agent) to give complex in the eluate. Hence, a complex further comprising the binding agent or eluting ligand is also provided in accordance with the present invention. The eluting ligand will then be removed from the eluate solution by dialysis in buffers appropriate for GMP production including, but not limited to, physiological salts and volatile salts.

The binding substance can be conjugated with a detectable label and in this case, the detecting step comprises: separating the complex from unbound labeled binding substance; and detecting the detectable label which is present in the complex or which is unbound.

D.5. Kits for Purification or Detection

In another aspect, the present invention pertains to a kit for isolating or purifying a peptide complex, preferably a GRP94 complex, and an antigenic molecule. In one embodiment, the kit comprises a binding agent that preferentially binds GRP94, the binding agent contained in a first container. The binding agent preferably comprises an adenosine moiety or structural mimetic thereof having any of a variety of substitutions at the 2', 3', and 5' positions, in the case of adenosine, as deemed appropriate by high resolution structural analyses of ligand-GRP94 interactions. Optionally, 5' position alkyl extensions can be included, preferably as a carboxamido linkage to the parent adenosine and, to facilitate stable chemical linkage to a solid support for the purposes of affinity-based purification, terminating in any of a subset of chemically reactive groups including, but not limited to vinyl, maleimide and/or succinimide esters, or substituents suitable for chemical coupling to solid phase supports, such as amino or sulphydryl groups. More preferably, the binding agent is free of ATP or ADP.

A representative binding agent comprises a compound of formula (I) or a compound of formula (II). Another representative binding agent comprises N-ethylcarboxamidoadenosine (NECA). Additional ligands can be identified through combinatorial chemistry of a parent precursor molecule bearing a hydrogen bond mimetic, preferably corresponding to the ribose of adenosine, and a benzimidazole or structurally related scaffold, corresponding to the adenine base of adenosine. Optionally, the binding agent can be immobilized to a solid phase support, or the kit can also comprise a solid phase support contained in a second container.

The kit can further comprise an elution buffer for use in eluting a complex from the binding agent, the elution buffer contained in a third container. Optionally, the elution buffer comprises a physiological salts solution containing appropriate concentrations of the parent ligand to give complex in the eluate. The kit can further comprise dialysis buffers appropriate for GMP production including, but not limited to, physiological salts and volatile salts. The kit can also further comprise an elution buffer for use in eluting an antigenic molecule from a complex, the elution buffer contained in a fourth container. Suitable elution buffers are disclosed herein above.

In the case of a kit used for detecting a complex comprising GRP94, or alternatively a complex comprising the kit can further comprise a reagent or indicator that comprises a detectable label, the indicator containing in a fifth container. Alternatively, the binding agent can comprise a detectable label or indicator. The indicator can comprise a radioactive label or an enzyme, or other indicator as disclosed herein.

D.6. Determination of Immunogenicity of GRP94-Peptide Complexes

Purified GRP94-antigenic molecule complexes can be assayed for immunogenicity using the mixed lymphocyte tumor culture assay (MLTC) well known in the art. By way of example but not limitation, the following procedure can be used. Briefly, mice are injected subcutaneously with the candidate GRP94-antigenic molecule complexes. Other mice are injected with either other GRP94-antigenic molecule complexes or whole infected cells which act as positive controls for the assay. The mice are injected twice, 7-10 days apart. Ten days after the last immunization, the spleens are removed and the lymphocytes released. The released lymphocytes can be re-stimulated subsequently in vitro by the addition of dead cells that expressed the complex of interest.

For example, $8 \times 10^6$ immune spleen cells can be stimulated with $4 \times 10^4$ mitomycin C treated or γ-irradiated (5-10,000 rads) infected cells (or cells transfected with an appropriate gene, as the case can be) in 3 ml RPMI medium containing 10% fetal calf serum. In certain cases 33% secondary mixed lymphocyte culture supernatant can be included in the culture medium as a source of T cell growth factors, such as is described by Glasebrook et al. (1980) *J Exp Med* 151:876. To test the primary cytotoxic T cell response after immunization, spleen cells can be cultured without stimulation. In some experiments spleen cells of the immunized mice can also be re-stimulated with antigenically distinct cells, to determine the specificity of the cytotoxic T cell response.

Six days later the cultures are tested for cytotoxicity in a 4 hour $^{51}$Cr-release assay as is described by Palladino et al. (1987) *Cancer Res* 47:5074-5079 and Blachere et al. (1993) *J Immunotherapy* 14:352-356. In this assay, the mixed lymphocyte culture is added to a target cell suspension to give different effector:target (E:T) ratios (usually 1:1 to 40:1). The target cells are prelabeled by incubating $1 \times 10^6$ target cells in culture medium containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5%.

E. Screening Methods

Disclosed herein is the molecular basis, as well as a high throughput screen, for chemical compounds that elicit or inhibit conformational changes in the molecular chaperone GRP94, or in some instances HSP90, thereby regulating the chaperone and peptide binding activities of these proteins.

Also disclosed herein are several new and unique aspects of the regulation of GRP94 structure and function that can be readily exploited for purposes of identifying agonists and antagonists ("modulators") of GRP94 function. GRP94 expression is upregulated by cellular stresses such as nutrient deprivation, oxidative stress, heavy metal posioning, hypoxia/anoxia, and other conditions related to ischemia. However, until the disclosure of the present invention, the molecular mechanism underlying this activity remained unknown. Thus, disclosed herein is a functional correlation to heat shock in the observation that heat shock stimulates the peptide binding and chaperone activity of GRP94. The heat shock response of GRP94, which is responsible for its increased peptide binding and chaperone activity, is a result of a change in the conformational state of the protein from a closed form to an open, active form.

The heat shock induced conformational change can be blocked by the antitumor drugs geldanamycin and radicicol, thus providing a mechanism of their antitumor activity, namely that geldanamycin and radicicol block GRP94 conformational transitions, and hence chaperone activity. The functional consequence of such inhibition is that oncogenic signaling proteins, such as growth factor receptor kinases are not processed properly and thus, the cell does not receive the proliferative signals necessary for transformation. Thus, a chemical compound that modulates the conformation of GRP94 can be used to treat a disease state, such as cancer, wherein a therapeutic benefit can be provided by inhibiting or blocking the egress of proteins (e.g., growth factors) from the endoplasmic reticulum.

The present invention provides the theoretical and structural basis for the identification of low molecular weight molecules that bind to a recently crystallized conserved N-terminal domain of HSP90, which previously was identified as the binding site for the anti-tumor drug geldanamycin, and elicit a conformation change that yields a dramatic and substantial increase in (poly)peptide binding activity of GRP94, and in some cases, HSP90. In an alternative embodiment, the identified molecules inhibit conformational activation of GRP94, and in some cases HSP90, similar to the observed modulation of GRP94 and HSP90 by geldanamycin and/or radicicol.

The present invention is markedly distinguished from current perception in the art as to the mechanism of regulation of GRP94 and HSP90 function. In current views, the Hsp90 family of molecular chaperones are thought to be regulated by cycles of ATP binding and hydrolysis (Prodromou et al. (1997) *Cell* 90:65-75). This view of Hsp90 function is based on the observations that the highly conserved N-terminal domain of the protein contains a binding site for ATP and ADP and that X-ray crystallographic structures of the domain in complex with ATP and/or ADP can be obtained.

In accordance with the present invention, data are provided demonstrating that the related and relevant domain of the HSP90 paralog GRP94 does not display a specific structural preference for ATP or ADP. In a series of function-directed studies, applicants have further determined that ATP, ADP, geldanamycin and radicicol block or inhibit the ability of GRP94 to assume a conformation necessary for chaperone activity and/or peptide binding. Thus, ATP and ADP, rather than being physiological ligands agonising the activity of GRP94, act as inhibitory agents for this chaperone.

The identified conformational change in GRP94 is a component of the regulatory cycle of GRP94, as demonstrated in the Examples wherein bis-ANS, which bears structural similarities to adenosine nucleotides, was demonstrated to elicit a tertiary conformational change in GRP94 that was accompanied by an activation of molecular chaperone and peptide binding activity.

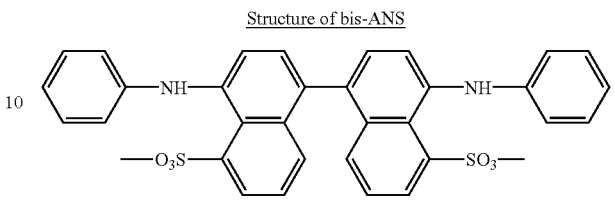

Structure of bis-ANS

In accordance with the present invention, also disclosed herein are the primary structural determinants that define low molecular weight compounds that bind to the conserved N-terminal domain of GRP94 and either A) elicit a conformational change in GRP94 that is accompanied by an activation of either peptide binding and/or molecular chaperone activity, or B) block or inhibit the ability of GRP94 to access or acquire the described conformation. In the present invention, and as would be apparent to one of ordinary skill in the art of the regulation of protein structure/function after reviewing the disclosure presented herein, cells and tissues originating from higher eukaryotes contain a native ligand compound bearing structural similarities to adenosine, yet may bear substituents at the 2' and 5' positions, but lack substituents at the N6 adenine.

Thus, a native ligand, as well an embodiment of mimetic thereof, bears an adenosine moiety or moieties and the adenosine moiety(s) function in the binding of the ligand to the conserved N-terminal domain of GRP94 previously identified as an ATP/ADP binding pocket. Representative ligand compositions are disclosed herein above as formulas (I) and (II). Additional ligands can be identified through combinatorial chemistry of a parent precursor molecule bearing a hydrogen bond mimetic, preferably corresponding to the ribose of adenosine, and a benzimidazole or structurally related scaffold, corresponding to the adenine base of adenosine.

The binding of a ligand elicits the conformational change that is accompanied by an activation of chaperone and peptide binding activity. Furthermore, synthesis of the native ligand is likely stimulated by conditions that elicit a disruption in the efficiency of protein folding and assembly in the ER. These conditions include, but are not limited to, heat shock, oxidative stress, nutrient deprivation, disruptions in oligosaccharide synthesis and covalent assembly on to nascent glycoproteins, and the presence of excessive levels of heavy metals.

Coincident with the discovery of the functional role for GRP94 structural transitions in determining the chaperone activity and the mechanism of geldanamycin and radicicol action, a simple and rapid method for assaying the conformational state of GRP94 (or alternatively, HSP90) is disclosed herein. A preferred embodiment of this method is based on the preferential binding of the small synthetic fluorescent probe, bis-ANS, to the open, or active, conformation of GRP94. bis-ANS binding yields a dramatic increase in probe fluorescence intensity. bis-ANS is identified herein as a highly sensitive indicator of the heat shock induced conformational change of GRP94. Furthermore, bis-ANS itself can elicit the conformational change in GRP94 necessary for the activation of peptide binding and chaperone function. Thus, bis-ANS is both an agonist for GRP94 activation as well as an indicator for the relative state of activation. bis-ANS induces these changes on a slow time scale, thereby enabling it to be used both as an inducer for a heat shock-like conformational change as well as a probe for conformational changes induced by other compounds. Conversely, and as disclosed in the Examples, bis-ANS can be used to identify compounds that block the heat shock-induced conformational changes. Indeed, the screening system of the present invention showed that radicicol and geldanamycin, two anti-tumor agents known to act through GRP94/HSP90, block the conversion of these proteins to the conformation necessary for function.

Another preferred embodiment of this method employs a related synthetic fluorescent probe, 8-ANS. 8-ANS also displays preferential binding to the active conformation of GRP94. However, unlike bis-ANS, 8-ANS functions solely as an indicator and lacks agonist activity. 8-ANS is also useful in screening assays for discovery of GRP94 modulators.

Therefore, in accordance with the present invention, a method of screening candidate compounds for an ability to modulate the biological activity is provided. The screening methods are also used to identify a native or endogenous ligand or ligands for GRP94.

In one embodiment, a candidate substance is a substance which potentially can modulate the biological activity of GRP94 by binding or other intermolecular interaction with GRP94. By "modulate" is intended an increase, decrease, or other alteration of any or all biological activities or properties of GRP94. Thus, a native or endogenous ligand or ligands of GRP94 is also a "candidate substance". A biological sample suspected of containing a native or endogenous ligand or ligands is also a "candidate substance". Small molecules and combinatorial libraries of small molecules are also candidate "substances". A candidate substance identified according to a screening assay described herein has the ability to modulate GRP94 biological activity. Such a candidate substance has utility in the treatment of disorders and conditions wherein modulation of the biological activity of GRP94 is desirable, as well as in the purification and screening methods disclosed herein.

The present invention thus pertains to the molecular basis for as well as a high throughput screen for chemical compounds that elicit or inhibit conformational changes in the molecular chaperone GRP94, or in some instances HSP90, thereby regulating the chaperone and peptide binding activities of these proteins.

E.1. General Screening Methods

A method of screening candidate substances for an ability to modulate GRP94 and/or HSP90 biological activity is thus provided in accordance with the present invention. In one embodiment, the method comprises (a) establishing a test sample comprising GRP94 and a ligand for GRP94; (b) administering a candidate substance or a sample suspected of containing a candidate substance to the test sample; and (c) measuring an effect on binding of GRP94 and the ligand for GRP94 in the test sample to thereby determine the ability of the candidate substance to modulate GRP94 biological activity.

The test sample can further comprise an indicator. The term "indicator" is meant to refer to a chemical species or compound that is readily detectable using a standard detection technique, such as dark versus light detection, fluorescence or chemiluminescence spectrophotometry, scintillation spectroscopy, chromatography, liquid chromatography/mass spectroscopy (LC/MS), colorimetry, and the like. Representative indicator compounds thus include, but are not limited to, fluorogenic or fluorescent compounds, chemiluminescent compounds, calorimetric compounds, UV/VIS absorbing compounds, radionucleotides and combinations thereof. In a preferred embodiment, the ligand further comprises an indicator. In a more preferred embodiment, the ligand/indicator comprises 1,8-anilinonapthalenesulfonate (8-ANS).

The ability of the candidate substance to modulate GRP94 and/or HSP90 biological activity can determined in any suitable manner. For example, the ability of the candidate substance to modulate GRP94 and/or HSP90 biological activity can determined by: (i) detecting a signal produced by the indicator upon an effect of the candidate substance on binding of GRP94 and/or HSP90 and the ligand for GRP94 and/or HSP90; and (ii) identifying the candidate substance as a modulator of GRP94 and/or HSP90 biological activity based upon an amount of signal produced as compared to a control sample.

In a preferred embodiment, a simple and effective fluorescence based screening methodology is provided to identify inhibitors and activators of the conformational transitions of GRP94 which are responsible for its activity. The method is readily amenable to both robotic and very high throughput systems.

Thus, in one embodiment, a screening method of the present invention pertains to a method for a identifying a candidate substance as an activator of the biological activity of an Hsp90 protein. In a preferred embodiment, the Hsp90 protein is GRP94 or HSP90. The method comprises establishing a test sample comprising an Hsp90 protein and a candidate substance; administering 8-ANS to the test sample; and detecting a fluorescence signal produced by the 8-ANS; and identifying the candidate substance as an activator of the biological activity of the Hsp90 protein based upon an amount of fluorescence signal produced by the 8-ANS as compared to a control sample.

The method can further comprise incubating the Hsp90 protein with the candidate substance at 37° C for about one hour prior to adding the 8-ANS. Optionally, the 8-ANS can be added in an approximately equimolar amount to the Hsp90 protein. Additionally, the candidate substance is identified as an activator of the biological activity of an Hsp90 protein by detection of an increased 8-ANS fluorescence signal as compared to a control sample.

In another embodiment, a screening method of the present invention pertains to a method for a identifying a candidate substance as an inhibitor of the biological activity of a Hsp90 protein. The method comprises establishing a test sample comprising an Hsp90 protein and a candidate substance; heat-shocking the test sample to induce a conformational change to the Hsp90 protein; administering 8-ANS to the test sample; detecting a fluorescence signal produced by the 8-ANS; and identifying the candidate substance as an inhibitor of the biological activity of an Hsp90 protein based upon an amount of fluorescence signal produced by the 8-ANS as compared to a control sample. In a preferred embodiment, the Hsp90 protein is GRP94 or HSP90.

Optionally, the method can further comprise incubating the test sample at 37° C. for about one hour prior to heat-shocking the test sample. The heat-shocking can be carried out at 50° C. for about 15 minutes. Preferably, the 8-ANS is added in an approximately equimolar amount to the Hsp90 protein. The candidate substance can also be identified as an inhibitor of the biological activity of an Hsp90 protein by detection of a decreased 8-ANS fluorescence signal as compared to a control sample.

E.2. Cell Based Screening Assays

A screening assay of the present invention may also involve determining the ability of a candidate substance to modulate, i.e. inhibit or promote the biological activity of an Hsp90 protein such as GRP94 and preferably, to thereby modulate the biological activity of an Hsp90 protein such as GRP94 in target cells. Target cells can be either naturally occurring cells known to contain a polypeptide of the present invention or transformed cells produced in accordance with a process of transformation set forth herein above. The test samples can further comprise a cell or cell line that expresses an Hsp90 polypeptide; the present invention also contemplates a recombinant cell line suitable for use in the exemplary method. Such cell lines may be mammalian, or human, or they may from another organism, including but not limited to yeast.

Representative assays including genetic screening assays and molecular biology screens such as a yeast two-hybrid screen that will effectively identify Hsp90-interacting genes important for Hsp90 or other Hsp90-mediated cellular process, including a native Hsp90 ligand or ligands. One version of the yeast two-hybrid system has been described (Chien et al. (1991) *Proc Natl Acad Sci USA* 88:9578-9582) and is commercially available from Clontech (Palo Alto, Calif.). Thus, in accordance with one embodiment of a screening assay of the present invention, the candidate substance is further characterized as a candidate polypeptide, and the screening method can further comprise the step of purifying and isolating a nucleic acid molecule encoding the candidate polypeptide.

Thus, enzymes in the cells of higher eukaryotes that mediate the steady state and stress-elicited production of a GRP94 and/or HSP90 ligand can also be modulated in accordance with the present invention. Such catabolic enzymes also represent appropriate and rational targets for the design of compounds that elicit an increase in the steady state levels of a native Hsp90 ligand (e.g., a native GRP94 or HSP90 ligand) and thereby lead to the elicitation of the structural and functional activation of chaperone and peptide binding activity of an Hsp90 protein, preferably GRP94, disclosed herein.

A screening assay can provide a cell under conditions suitable for testing the modulation of biological activity of an Hsp90 protein such as GRP94. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. A polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell. U.S. Pat. Nos. 5,837,479; 5,645,999; 5,786,152; 5,739,278; and 5,352,660 also describe exemplary screening assays, and the entire contents of each are herein incorporated by reference.

E.3. High Throughput Screening

In another embodiment of the screening method of the present invention, an Hsp90 polypeptide (e.g., human GRP94) or active fragment or oligopeptide thereof, can be used for screening libraries of compounds in any of a variety of high throughput drug screening techniques. The fragment employed in such screening may be free in solution, affixed to a solid support, borne on a cell surface, or located intracellularly. The formation of binding complexes, between the Hsp90 polypeptide, preferably a GRP94 polypeptide, and the candidate substance being tested, can be measured as described herein.

E.4. Rational Drug Design

A method of identifying modulators of an Hsp90 protein by rational drug design is also provided in accordance with the present invention. The method comprises designing a potential modulator for an Hsp90 protein that will form non-covalent bonds with amino acids in the substrate binding site based upon the structure of an Hsp90 protein preferably GRP94; synthesizing the modulator; and determining whether the potential modulator modulates the activity of an Hsp90 protein. Modulators may be synthesized using techniques known in the art. The determination of whether the modulator modulates the biological activity of an Hsp90 protein is made in accordance with the screening methods disclosed herein, or by other screening methods known in the art. This is the method of "rational" drug design.

Additional representative rational drug design techniques are described in U.S. Pat. Nos. 5,834,228 and 5,872,011, the entire contents of which are herein incorporated by reference.

Thus, a method of identifying modulators of an Hsp90 protein by rational drug design is provided in accordance with the present invention. The method comprises designing a potential modulator for an Hsp90 protein that will form non-covalent bonds with amino acids in the Hsp90 protein substrate binding site based upon a crystal structure of an Hsp90 protein; synthesizing the modulator; and determining whether the potential modulator modulates the activity of an Hsp90 protein. Modulators are synthesized using techniques disclosed herein and as are known in the art. The determination of whether the modulator modulates the biological activity of an Hsp90 protein is made in accordance with the screening methods disclosed herein above. In a preferred embodiment, the Hsp90 protein is GRP94.

F. Modulation of Hsp90 Biological Activity

Because Hsp90 proteins are found in essentially every cell of the human body and are involved in the processing of many different cellular proteins as well as the presentation of tumor and foreign antigens to the immune system, compounds identified through the screening method of the present invention and disclosed herein (referred to as "ligand compositions" or "modulators") have wide ranging value as therapeutics and in vaccine development. Representative ligand compositions or modulators are described herein above as formula (I). Modulators that do not structurally resemble adenosine are also provided, and include those designed and/or identified by the rational drug design and combinatorial screening methods disclosed hereinabove.

In a preferred embodiment, the Hsp90 modulator elicits a conformational change in an Hsp90 protein. Even more preferably, the Hsp90 protein activity modulator is identified according to a screening assay described herein. A modulator can modulate the biological activity of an Hsp90 protein such as GRP94. Relevant to the antigen-presenting activity of GRP94 and HSP90, activators thereof can be applied in vitro to assist in peptide loading onto these proteins for the production of vaccines directed against the tissues or invasive organisms possessing those specific peptide epitopes. Activators of GRP94/HSP90 biological activity can be applied to tumor cells excised from cancer patients to increase the antigenicity of the tumor cells prior to lethal inactivation of the cells and their re-injection into the body as immunostimulatory agents. Activators of GRP94/HSP90 biological activity can be administered directly into the body of a vertebrate for increasing the antigenicity of tumors in situ. Activators of GRP94/HSP90 biological activity can also have antibiotic action against bacteria, viruses, or internal parasites by increasing the antigenicity of the bacteria, virus, or parasites and recognition of same by the adaptive immune system. Activators of GRP94/HSP90 biological activity can be used in further screens to identify peptides from combinatorial libraries which represent specific anti-tumor, anti-viral, or anti-bacterial epitopes. Relevant to the chaperone activity of GRP94 and HSP90, activators thereof can also ameliorate or prevent cellular damage resulting from ischemic conditions.

Inhibitors of GRP94/HSP90 function can possess antitumor activity. Inhibitors of GRP94/HSP90 function can also interfere with the processing of viral or bacterial proteins in infectious states and slow the progress of these infections. Inhibitors of GRP94/HSP90 function can also be administered to a vertebrate subject to decrease the antigenicity of tissues to alleviate transplanted tissue rejection or even slow the progression of autoimmune diseases such as rheumatoid arthritis and systemic lupus erythramatosis. Inhibitors of GRP94 activity can also be used for treatment of diseases, such as cancer, by inhibiting or blocking the egress of proteins (e.g., growth factors) from the endoplasmic reticulum.

A biological activity of a Hsp90 protein such as GRP94 that is modulated in accordance with the present invention can include, but is not limited to, loading activity in the formation of a complex with antigenic molecules, eliciting an immune response in a subject; treating or preventing a type of cancer in a subject; treating or preventing an infectious disease in a subject; sensitizing antigen presenting cells (APC), particularly with respect to a type of cancer or an infectious disease; and enhancing protein transport along the endoplasmic reticulum.

Another modulatable biological activity of a Hsp90 protein comprises preventing or ameliorating cellular damage arising from conditions of ischemia/reperfusion including but not limited to cardiac arrest, asystole and sustained ventricular arrythmias, cardiac surgery, cardiopulmonary bypass surgery, organ transplantation, spinal cord injury, head trauma, stroke, thromboembolic stroke, hemorrhagic stroke, cerebral vasospasm, hypotension, hypoglycemia, status epilepticus, an epileptic seizure, anxiety, schizophrenia, a neurodegenerative disorder, Alzheimer's disease, Huntington's disease, amyotrophic lateral sclerosis (ALS), or neonatal stress. In this case, a ligand can modulate an endogenous Hsp90 protein by promoting conformational activation of the Hsp90 protein. Preferably, the ligand was identified according to a screening or rational drug design method disclosed herein and is relevant for the modulation of GRP94 or HSP90.

F.1. In vitro Production of GRP94-Antigenic Molecule Complexes

In accordance with the present invention, complexes of an Hsp90 protein, such as GRP94, to antigenic molecules are produced in vitro using an Hsp90 protein activity modulator. As will be appreciated by those skilled in the art, the peptides either isolated by procedures disclosed herein, chemically synthesized or recombinantly produced, can be reconstituted with a variety of naturally purified or recombinant Hsp90 proteins in vitro to generate, for example, immunogenic non-covalent GRP94-antigenic molecule complexes. Alternatively, exogenous antigens or antigenic/immunogenic fragments or derivatives thereof can be non-covalently complexed to an Hsp90 protein for use in the immunotherapeutic or prophylactic vaccines of the invention. The complexes can then be purified using any suitable method, and are preferably purified via the affinity purification methods of the present invention disclosed herein above.

In a representative approach, antigenic molecules (1 µg) and GRP94 (9 µg) are admixed to give an approximately 5 antigenic molecule:1 GRP94 molar ratio. Then, the mixture is incubated for 15 minutes to 3 hours at 4° C. to 45° C. with bis-ANS in a quantity equimolar to GRP94 in a suitable binding buffer such as one containing 20 mM sodium phosphate, pH 7.2, 350 mM NaCl, 3 mM $MgCl_2$ and 1 mM phenyl methyl sulfonyl fluoride (PMSF). The preparations are centrifuged through CENTRICON®10 assembly (Amicon of Beverly, Mass.) to remove any unbound peptide. The association of the peptides with GRP94 can be assayed by SDS-PAGE. Additional representative approaches are disclosed in the Examples.

Following complexing, the immunogenic GRP94-antigenic molecule complexes can optionally be assayed in vitro using, for example, the mixed lymphocyte tumor cell assay (MLTC) described herein. Once immunogenic complexes have been isolated they can be optionally characterized further in animal models using the preferred administration protocols and excipients discussed herein.

F.1.1. Exogenous Antigenic Molecules

Antigens or antigenic portions thereof can be selected for use as antigenic molecules, for complexing to an Hsp90 protein, such as GRP94, from among those known in the art or determined by immunoassay to be able to bind to antibody or MHC molecules (antigenicity) or generate immune response (immunogenicity). To determine immunogenicity or antigenicity by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immuno-electrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods and techniques are known in the art for detecting binding in an immunoassay and can be used. In one embodiment for detecting immunogenicity, T cell-mediated responses can be assayed by standard methods, e.g., in vitro cytotoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby (1985) "Summary" in *Vaccines* 85, Lerner et al. (eds.), pp. 388-389, Cold Spring Harbor Press, Cold Spring Harbor, N.Y.), type or group specificity, recognition by subjects antisera or immune cells, and/ or the demonstration of protective effects of antisera or immune cells specific for the antigen. In addition, where it is desired to treat or prevent a disease caused by a pathogen, the antigen's encoded epitope should preferably display a small or no degree of antigenic variation in time or amongst different isolates of the same pathogen.

Preferably, where it is desired to treat or prevent cancer, known tumor-specific antigens or fragments or derivatives thereof are used. For example, such tumor specific or tumor-associated antigens include but are not limited to KS ¼ pan-carcinoma antigen (Perez & Walker (1990) *J Immunol* 142: 3662-3667; Bumal (1988) *Hybridoma* 7(4):407-415); ovarian carcinoma antigen (CA125) (Yu et al. (1991) *Cancer Res* 51(2):468-475); prostatic acid phosphate (Tailer et al. (1990) *Nuc Acids Res* 18(16):4928); prostate specific antigen (Henttu & Vihko (1989) *Biochem Biophys Res Comm* 160(2):

903-910; Israeli et al. (1993) *Cancer Res* 53:227-230); melanoma-associated antigen p97 (Estin et al. (1989) *J Natl Cancer Inst* 81(6):445-446); melanoma antigen gp75 (Vijayasardahl et al. (1990) *J Exp Med* 171(4):1375-1380); high molecular weight melanoma antigen (Natali et al. (1987) *Cancer* 59:55-63) and prostate specific membrane antigen. In a specific embodiment, an antigen or fragment or derivative thereof specific to a certain tumor is selected for complexing to an Hsp90 protein, such as GRP94, and subsequent administration to a subject having that tumor.

Preferably, where it is desired to treat or prevent viral diseases, molecules comprising epitopes of known viruses are used. For example, such antigenic epitopes can be prepared from viruses including, but not limited to, hepatitis type A hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus (RSV), papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II). Preferably, where it is desired to treat or prevent bacterial infections, molecules comprising epitopes of known bacteria are used. For example, such antigenic epitopes can be prepared from bacteria including, but not limited to, Mycobacteria, Mycoplasma, Neisseria, and Legionella.

Preferably, where it is desired to treat or prevent protozoal infectious, molecules comprising epitopes of known protozoa are used. For example, such antigenic epitopes can be prepared from protozoa including, but not limited to, Leishmania, Kokzidioa, and Trypanosoma. Preferably, where it is desired to treat or prevent parasitic infectious, molecules comprising epitopes of known parasites are used. For example, such antigenic epitopes can be from parasites including, but not limited to, Chlamydia and Rickettsia.

F.1.2. Peptides from MHC Complexes

Candidate immunogenic or antigenic peptides can be isolated from either endogenous Hsp90-peptide complexes as described above or from endogenous MHC-peptide complexes for use subsequently as antigenic molecules, by complexing in vitro to an Hsp90 protein, such as GRP94. The isolation of potentially immunogenic peptides from MHC molecules is well known in the art and so is not described in detail herein. See Falk et al. (1990) *Nature* 348:248-251; Rotzsche et al. (1990) *Nature* 348:252-254; Elliott et al. (1990) *Nature* 348:191-197; Falk et al. (1991) *Nature* 351:290-296; Demotz et al. (1989) *Nature* 343:682-684; Rotzsche et al. (1990) *Science* 249:283-287, the disclosures of which are incorporated herein by reference. Briefly, MHC-peptide complexes can be isolated by a conventional immuno-affinity procedure. The peptides can then be eluted from the MHC-peptide complex by incubating the complexes in the presence of about 0.1% TFA in acetonitrile. The eluted peptides can be fractionated and purified by HPLC as described herein.

F.2. Therapeutic Methods for Modulating Hsp90 Biological Activity

A therapeutic method according to the present invention comprises administering to a subject in need thereof a substance that modulates, i.e., inhibits or promotes, biological activity of an Hsp90 protein, such as GRP94. Representative substances, also referred to as "ligand compositions" or "modulators" are disclosed herein (e.g., compounds of formula (I)) and can also be identified according to any of the screening assays set forth herein. The method comprises treating a subject suffering from a disorder wherein modulation of the biological activity of an Hsp90 protein is desirable by administering to the subject an effective amount of an Hsp90 modulator. Preferably, the Hsp90 protein is GRP94. More preferably, the modulator elicits a conformational change in an Hsp90 protein. Even more preferably, the modulator is identified according to a screening assay described herein.

By the term "modulating", it is meant that the substance can either promote or inhibit the biological activity of an Hsp90 protein, depending on the disorder to be treated, and can affect one or several of the Hsp90 proteins, including GRP94. Administration can provide treatment of disorders which can be exacerbated by GRP94/HSP90-mediated mechanisms, including but not limited to, cancer, infectious diseases, and ischemic conditions.

The subject treated in the present invention in its many embodiments is desirably a human subject, although it is to be understood that the principles of the invention indicate that the invention is effective with respect to invertebrate and to all vertebrate species, including mammals, which are intended to be included in the term "subject". This is particularly the case in view of the phylogenetically ubiquitous nature of Hsp90 proteins. Moreover, a mammal is understood to include any mammalian species in which treatment or prevention of cancer or infectious diseases is desirable, particularly agricultural and domestic mammalian species.

The methods of the present invention are particularly useful in the treatment of warm-blooded vertebrates. Therefore, the invention concerns mammals and birds.

More particularly, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

In one embodiment, a ligand composition or modulator is administered in conjunction with a complex comprising an Hsp90 protein (preferably GRP94 or HSP90) and an antigenic molecule. Preferably, the complex is "autologous" to the subject; that is, the complex is isolated from either from the infected cells or the cancer cells or precancerous cells of the subject (e.g., preferably prepared from infected tissues or tumor biopsies of a subject). More preferably, the complex is purified in accordance with a purification method of the present invention disclosed herein above.

Alternatively, the complex is produced in vitro (e.g., wherein a complex with an exogenous antigenic molecule is desired). Alternatively, the Hsp90 protein (preferably GRP94 or HSP90) and/or the antigenic molecule can be isolated from a particular subject or from others or by recombinant production methods using a cloned Hsp90 protein (preferably GRP94 or HSP90) originally derived from a particular subject or from others. Exogenous antigens and fragments and derivatives (both peptide and non-peptide) thereof for use in complexing with an Hsp90 protein, can be selected from among those known in the art, as well as those readily identified by standard immunoassays know in the art by the ability to bind antibody or MHC molecules (antigenicity) or generate immune response (immunogenicity). Complexes of an Hsp90 protein (preferably GRP94 or HSP90) and antigenic molecules can be isolated from cancer or precancerous tissue of a subject, or from a cancer cell line, or can be produced in vitro (as is necessary in the embodiment in which an exogenous antigen is used as the antigenic molecule). Preferably, the complex is purified in accordance with a purification method of the present invention disclosed herein above.

The invention also provides a method for measuring tumor rejection in vivo in a subject, preferably a human subject, comprising measuring the generation by the subject of MHC Class I-restricted $CD8^+$ cytotoxic T lymphocytes specific to the tumor after administering a complex comprising GRP94 and antigenic molecules specific to the tumor in conjunction with an GRP94 biological activity modulator. Preferably, GRP94 comprises human GRP94. The immunogenic GRP94-peptide complexes of the invention can include any complex containing a GRP94 and a peptide that is capable of inducing an immune response in a subject. The peptides are preferably non-covalently associated with the GRP94.

Although the Hsp90 protein can be allogenic to the subject (e.g., isolated from cancerous tissue from a second vertebrate subject that is the same type as a cancerous tissue present in a first vertebrate subject to be treated), in a preferred embodiment, the Hsp90 protein is autologous to (derived from) the subject to whom they are administered. The Hsp90 protein and/or antigenic molecules can be purified from natural sources, chemically synthesized, or recombinantly produced. Preferably, the complex and/or antigenic molecule is purified in accordance with a purification method of the present invention disclosed herein above. The invention provides methods for determining doses for human cancer immunotherapy by evaluating the optimal dose of an Hsp90 protein non-covalently bound to peptide complexes in experimental tumor models and extrapolating the data. Specifically, a scaling factor not exceeding a fifty-fold increase over the effective dose estimated in animals, is used as the optimal prescription method for cancer immunotherapy or vaccination in human subjects. Preferably, the Hsp90 protein is GRP94.

The invention provides combinations of compositions which enhance the immunocompetence of the host individual and elicit specific immunity against infectious agents or specific immunity against preneoplastic and neoplastic cells. The therapeutic regimens and pharmaceutical compositions of the invention are described below. These compositions have the capacity to prevent the onset and progression of infectious diseases and prevent the development of tumor cells and to inhibit the growth and progression of tumor cells, indicating that such compositions can induce specific immunity in infectious diseases and cancer immunotherapy. For example, Hsp90-antigenic molecule complexes can be administered in combination with other complexes, such as calreticulin, and antigenic molecules in accordance with the methods of the present invention.

Accordingly, the invention provides methods of preventing and treating cancer in a subject. A representative method comprises administering a therapeutically effective amount of an Hsp90 modulator (preferably a GRP94 modulator) to a subject in need thereof. Such a subject can include but is not limited to a subject suffering from cancer or at risk to develop cancer. Representative modulators that can be employed in the method comprise ligands that inhibit GRP94 (Hsp90) function. Such ligands are designed and identifed using the screening methods disclosed herein and are thus employed as anti-tumor drugs, and/or anti-neoplastic agents. Characterization of these activities can be accomplished via techniques disclosed herein and known in the art.

In another embodiment, the method comprises administering a complex comprising an Hsp90 protein and pertinent antigenic molecule in conjunction with a modulator which stimulates the immunocompetence of the host individual and elicits specific immunity against the preneoplastic and/or neoplastic cells. Preferably, the Hsp90 protein is GRP94.

As used herein, "preneoplastic" cell refers to a cell which is in transition from a normal to a neoplastic form; and morphological evidence, increasingly supported by molecular biologic studies, indicates that preneoplasia progresses through multiple steps. Non-neoplastic cell growth commonly consists of hyperplasia, metaplasia, or most particularly, dysplasia (for review of such abnormal growth conditions. See Robbins & Angell (1976) *Basic Pathology,* 2d Ed., pp. 68-79, W. B. Saunders Co., Philadelphia, Pa.).

Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. Although preneoplastic lesions can progress to neoplasia, they can also remain stable for long periods and can even regress, particularly if the inciting agent is removed or if the lesion succumbs to an immunological attack by its host.

The therapeutic regimens and pharmaceutical compositions of the invention can be used with additional adjuvants or biological response modifiers including, but not limited to, the cytokines IFN-α, IFN-γ, IL-2, IL-4, IL-6, TNF, or other cytokine affecting immune cells. In accordance with this aspect of the invention, a complex of an Hsp90 protein and an antigenic molecule along with a modulator are administered in combination therapy with one or more of these cytokines. Preferably, the Hsp90 protein is GRP94.

The invention also pertains to administration of a complex of an Hsp90 protein and an antigenic molecule and a modulator to individuals at enhanced risk of cancer due to familial history or environmental risk factors. Preferably, the Hsp90 protein is GRP94.

Enzymes in the cells of higher eukaryotes that mediate the steady state and stress-elicited production of a native GRP94 ligand can also be modulated in accordance with the present invention. Particularly, such catabolic enzymes represent appropriate and rational targets for modulation to elicit an increase in the steady state levels of a native GRP94 ligand and thereby lead to the elicitation of the structural and functional activation of chaperone and peptide binding activity of GRP94 disclosed herein.

Protein misfolding disorders are a common component of numerous genetic disease states including, but not limited to, cystic fibrosis, familial hypercholesterolemia, retinitis pigmentosa and α1-antitrypsin misfolding. Compounds that modulate the activity of the Hsp90 family of molecular chaperones can thus be used in accordance with a therapeutic method of the present invention for reversing the protein folding defects that identify the disease state or for enhancing protein transport from the endoplasmic reticulum of a cell. Thus, a compound that modulates the conformation of GRP94 can be used to treat a disease state resulting from defects in protein transport into or from the endoplasmic reticulum. Compounds that abrogate GRP94 activity can be used for the treatment of a disease state, such as cancer, wherein a therapeutic benefit can be provided by blocking the egress of proteins (e.g., growth factors) from the endoplasmic reticulum. conversely, compounds that promote GRP94 activity can be used to treat a disease wherein a therapeutic benefit can be provided by enhancing protein export from the endoplasmic reticulum.

The present invention also pertains to administration of compounds for the prevention or amelioration of cellular damage arising from conditions of ischemia/reperfusion including but not limited to cardiac arrest, asystole and sustained ventricular arrythmias, cardiac surgery, cardiopulmonary bypass surgery, organ transplantation, spinal cord injury, head trauma, stroke, thromboembolic stroke, hemorrhagic stroke, cerebral vasospasm, hypotension, hypoglycemia, status epilepticus, an epileptic seizure, anxiety, schizophrenia, a neurodegenerative disorder, Alzheimer's disease, Hunting-ton's disease, amyotrophic lateral sclerosis (ALS), or neonatal stress. In one embodiment, a composition comprising a Hsp90 ligand is administered to promote conformational activation of a Hsp90 protein, thereby promoting its cellular protective function relevant to recovery following a injury or onset of a disease state associated with ischemia. In another embodiment, administration of a composition comprising a Hsp90 ligand can alter a subsequent cellular response to an ischemic condition at a tissue location in a subject. Cells at the tissue location are contacted with a Hsp90 protein ligand, whereby Hsp90 activity in the cells is enhanced to a degree effective to alter a subsequent cellular response to an ischemic condition. Preferably, the therapeutic composition comprises a ligand identified according to a screening or rational drug design method disclosed herein. Also preferably, the therapeutic composition modulates the activity of GRP94 or HSP90.

F.3. Dosage Regimens

Actual dosage levels of active ingredients in the pharmaceutical compositions of this invention may be varied so as to administer an amount of the active compound(s) that is effective to achieve the desired therapeutic response for a particular subject. The selected dosage level will depend upon the activity of the particular compound, the route of administration, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular subject will depend upon a variety of factors including the body weight, general health, diet, time and route of administration, combination with other drugs and the severity of the particular disease being treated.

The dosage ranges for the administration of a modulator depend upon the form of the modulator, and its potency, as described further herein, and are amounts large enough to produce the desired effect. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

The therapeutic compositions can be administered as a unit dose. The term "unit dose" when used in reference to a therapeutic composition employed in the method of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies can also be administered.

A therapeutically effective amount is an amount of a modulator sufficient to produce a measurable modulation of Hsp9o protein (preferably GRP94) biological activity in a subject being treated, i.e., an Hsp90 protein biological activity-modulating amount. Modulation of Hsp90 protein biological activity can be measured using the screening methods disclosed herein, via the method disclosed in the Examples, or by other methods known to one skilled in the art.

The potency of a modulator can vary, and therefore a "therapeutically effective" amount can vary. However, as shown by the present assay methods, one skilled in the art can readily assess the potency and efficacy of a candidate modulator of this invention and adjust the therapeutic regimen accordingly. A modulator of Hsp90 protein (preferably GRP94) biological activity can be evaluated by a variety of methods and techniques including the screening assays disclosed herein.

A preferred modulator has the ability to substantially bind an Hsp90 protein in solution at modulator concentrations of less than one (1) micromolar (μM), preferably less than 0.1 μM, and more preferably less than 0.01 μM. By "substantially" is meant that at least a 50 percent reduction in biological activity is observed by modulation in the presence of the modulator, and at 50% reduction is referred to herein as an "IC50 value".

In one embodiment, the therapeutically effective amount of a modulator can respectively range from about 0.01 mg to about 10,000 mg per day. Alternatively, the therapeutically effective amount of a modulator can respectively range from about 0.1 mg to about 1,000 mg per day. Alternatively, the therapeutically effective amount of a modulator can respectively range from about 1 mg to about 300 mg per day. In a preferred embodiment, the therapeutically effective amount of a modulator can respectively range from about 15 mg per kg body weight per day to about 35 mg per kg body weight per day.

It was established in experimental tumor models (Blachere et al., 1993) that the lowest dose of heat shock proteins non-covalently bound to peptide complexes which produced tumor regression in mice was between 10 and 25 microgram/mouse weighing 20-25 g which is equal to 25 mg/25 g=1 mg/kg. Conventional methods extrapolate to human dosages based on body weight and surface area. For example, conventional methods of extrapolating human dosage based on body weight can be carried out as follows: since the conversion factor for converting the mouse dosage to human dosage is Dose Human per kg=Dose Mouse per kg×12 (Freireich et al. (1966) *Cancer Chemotherap Rep* 50:219-244), the effective dose of Hsp90-peptide complexes in humans weighing 70 kg should be 1 mg/kg÷12×70, i.e., about 6 mg (5.8 mg).

Drug doses are also given in milligrams per square meter of body surface area because this method rather than body weight achieves a good correlation to certain metabolic and excretionary functions (Shirkey (1965) *JAMA* 193:443). Moreover, body surface area can be used as a common denominator for drug dosage in adults and children as well as in different animal species as described by Freireich et al. (1966) *Cancer Chemotherap Rep* 50:219-244. Briefly, to express a mg/kg dose in any given species as the equivalent mg/sq m dose, multiply the dose by the appropriate km factor. In adult human, 100 mg/kg is equivalent to 100 mg/kg×37 kg/sq m=3700 mg/sq m.

International Publication Nos. WO 95/24923, WO 97/10000, WO 97/10002, and WO 98/34641, as well as U.S. Pat. Nos. 5,750,119, 5,830,464, and 5,837,251, each provide dosages of the purified complexes of heat shock proteins and antigenic molecules, and the entire contents of each of these documents are herein incorporated by reference. Briefly, and as applied to the present invention, an amount of Hsp90 protein (preferably GRP94)-antigenic molecule complexes is administered that is in the range of about 10 microgram to about 600 micrograms for a human subject, the preferred human dosage being the same as used in a 25 g mouse, i.e., in the range of 10-100 micrograms. The dosage for Hsp90 protein (preferably GRP94)-peptide complexes in a human subject provided by the present invention is in the range of about 50 to 5,000 micrograms, the preferred dosage being 100 micrograms.

In a series of preferred and more preferred embodiments, the Hsp90-peptide complex is administered in an amount of less than about 50 micrograms. In this case, the Hsp90 protein (preferably GRP94)-peptide complex is preferably administered in an amount of ranging from about 5 to about 49 micrograms. In a preferred embodiment, a GRP94-peptide complex is administered in an amount of less than about 10 micrograms. In this case, the GRP94-peptide complex is preferably administered in an amount ranging from about 0.1 to about 9.0 micrograms. More preferably, the GRP94-peptide complexes is administered in an amount ranging from about 0.5 to about 2.0 micrograms. In accordance with one aspect of the present invention, administration of a lower dosage of complex is facilitated and preferred when a modulator is also administered.

The doses recited above are preferably given once weekly for a period of about 4-6 weeks, and the mode or site of administration is preferably varied with each administration. In a preferred example, subcutaneous administrations are given, with each site of administration varied sequentially. For example, half the dose can be given in one site and the other half on an other site on the same day.

Alternatively, the mode of administration is sequentially varied. For example, weekly injections are given in sequence subcutaneously, intramuscularly, intravenously or intraperitoneally. After 4-6 weeks, further injections are preferably given at two-week intervals over a period of time of one month. Later injections can be given monthly. The pace of later injections can be modified, depending upon the subject's clinical progress and responsiveness to the immunotherapy.

F.4. Therapeutic Compositions for Immune Responses to Cancer

Compositions comprising an Hsp90 protein bound (e.g., GRP94-preferably non-covalently bound) to antigenic molecules are administered to elicit an effective specific immune response to the complexed antigenic molecules (and preferably not to the HSP90 protein). In a preferred embodiment, non-covalent complexes of the Hsp90 protein with peptides are prepared and purified postoperatively from tumor cells obtained from the cancer patient that have also been treated with an Hsp90 protein biological activity modulator in accordance with the present invention. A preferred Hsp90 protein is GRP94. In a more preferred embodiment, the complexes are purified using an affinity purification method of the present invention, as disclosed herein above.

In accordance with the methods described herein, immunogenic or antigenic peptides that are endogenously complexed to Hsp90 (e.g. GRP94) or MHC antigens can be used as antigenic molecules. For example, such peptides can be prepared that stimulate cytotoxic T cell responses against different tumor antigens (e.g., tyrosinase, gp100, melan-A, gp75, mucins, etc.) and viral proteins including, but not limited to, proteins of immunodeficiency virus type I (HIV-I), human immunodeficiency virus type II (HIV-II), hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus (RSV), papilloma virus, papova virus, cytomegalovirus, echinovirus, arbovirus, huntavirus, coxsackie virus, mumps virus, measles virus, rubella virus and polio virus. In the embodiment wherein the antigenic molecules are peptides noncovalently complexed to GRP94 in vivo, the complexes can be isolated from cells, or alternatively, produced in vitro from purified preparations each of GRP94 and antigenic molecules. The complexes can be further purified using an affinity purification method of the present invention, as disclosed herein above.

In another specific embodiment, antigens of cancers (e.g., tumors) or infectious agents (e.g., viral antigen, bacterial antigens, etc.) can be obtained by purification from natural sources, by chemical synthesis, or recombinantly, and, through in vitro procedures such as those described herein, complexed to GRP94. The complexes can also be further purified using an affinity purification method of the present invention, as disclosed herein above.

F.5. Formulation

In accordance with the present invention, modulators as well as antigenic molecule complexes can be formulated into pharmaceutical preparations for administration to a subject for treatment or prevention of cancer or infectious diseases. Compositions comprising a complex prepared in accordance with the present invention are formulated in a compatible pharmaceutical carrier can be prepared, packaged, and labeled for treatment of the indicated disorder (e.g. cancer or infectious disease).

If the modulator or complex is water-soluble, then it can be formulated in an appropriate buffer, for example, phosphate buffered saline or other physiologically compatible solutions. Alternatively, if a modulator or a resulting complex has poor solubility in aqueous solvents, then it can be formulated with a non-ionic surfactant, such as TWEEN™, or polyethylene glycol. Thus, the compounds and their physiologically acceptable solvates can be formulated for administration by inhalation or insufflation (either through the mouth or the nose) or oral, buccal, parenteral, rectal administration or, in the case of tumors, directly injected into a solid tumor.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art. Preparations for oral administration can be suitably formulated to give controlled release of the active compound.

For buccal administration, the compositions can take the form of tablets or lozenges formulated in conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, for example, gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, for example, in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

The invention also provides kits for carrying out the therapeutic regimens of the invention. Such kits comprise in one or more containers therapeutically or prophylactically effective amounts of a modulator and/or a antigenic molecule complex in pharmaceutically acceptable form. The modulator and the antigenic molecule complex in a vial of a kit of the invention can be in the form of a pharmaceutically acceptable solution, e.g., in combination with sterile saline, dextrose solution, or buffered solution, or other pharmaceutically acceptable sterile fluid. Alternatively, the modulator or complex can be lyophilized or desiccated; in this instance, the kit optionally further comprises in a container a pharmaceutically acceptable solution (e.g., saline, dextrose solution, etc.), preferably sterile, to reconstitute the modulator complex to form a solution for injection purposes.

In another embodiment, a kit of the invention further comprises needles or syringes, preferably packaged in sterile form, for injecting the modulator and complex, and/or a packaged alcohol pad. Instructions are optionally included for administration of antigenic molecule complexes by a clinician or by the subject.

G. Target Infectious Diseases

Infectious diseases that can be treated or prevented by the methods of the present invention are caused by infectious agents including, but not limited to, viruses, bacteria, fungi, protozoa and parasites. In one embodiment of the present invention wherein it is desired to treat a subject having an infectious disease, the above-described affinity purification methods are used to isolate GRP94-peptide complexes from cells infected with an infectious organism, e.g., of a cell line or from a subject.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus (RSV), papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, Mycobacteria, Mycoplasma, Neisseria, and Legionella.

Protozoal diseases that can be treated or prevented by the methods of the present invention are caused by protozoa including, but not limited to, Leishmania, Kokzidioa, and Trypanosoma. Parasitic diseases that can be treated or prevented by the methods of the present invention are caused by parasites including, but not limited to, Chlamydia and Rickettsia.

H. Target Cancers

Cancers that can be treated or prevented by the methods of the present invention include, but not limited to human sarcomas and carcinomas, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenströom's macroglobulinemia, and heavy chain disease.

In a specific embodiment the cancer is metastatic. In another specific embodiment, the subject having a cancer is immunosuppressed by reason of having undergone anti-cancer therapy (e.g., chemotherapy radiation) prior to administration of the GRP94-antigenic molecule complexes and a GRP94 modulator in accordance with the present invention.

I. Combination With Adoptive Immunotherapy

Adoptive immunotherapy refers to a therapeutic approach for treating cancer or infectious diseases in which immune cells are administered to a host with the aim that the cells mediate either directly or indirectly specific immunity to tumor cells and/or antigenic components or regression of the tumor or treatment of infectious diseases, as the case can be. In accordance with the methods described herein, APC are sensitized with GRP94 preferably noncovalently complexed with antigenic (or immunogenic) molecules in conjunction with a GRP94 biological activity modulator and used in adoptive immunotherapy.

According to one embodiment of the present invention, therapy by administration of GRP94-peptide complexes and a GRP94 biological activity modulator, using any desired route of administration, is combined with adoptive immunotherapy using APC sensitized with GRP94-antigenic molecule complexes and a modulator. The sensitized APC can be administered concurrently with GRP94-peptide complexes and the modulator, or before or after administration of GRP94-peptide complexes and the modulator. Furthermore, the mode of administration can be varied, including but not limited to, e.g., subcutaneously, intravenously, intraperitoneally, intramuscularly, intradermally or mucosally.

I.1. Obtaining Macrophages and Antigen-Presenting Cells

The antigen-presenting cells, including but not limited to macrophages, dendritic cells and B-cells, are preferably obtained by production in vitro from stem and progenitor cells from human peripheral blood or bone marrow as described by Inaba (1992) *J Exp Med* 176:1693-1702.

APC can be obtained by any of various methods known in the art. In a preferred aspect human macrophages are used, obtained from human blood cells. By way of example but not limitation, macrophages can be obtained as follows: mononuclear cells are isolated from peripheral blood of a subject (preferably the subject to be treated), by Ficoll-Hypaque gradient centrifugation and are seeded on tissue culture dishes which are pre-coated with the subject's own serum or with other AB+ human serum. The cells are incubated at 37° C. for 1 hr, then non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages can be obtained by incubating at 37° C. with macrophage-colony stimulating factor (M-CSF); increased numbers of dendritic cells can be obtained by incubating with granulocyte-macrophage-colony stimulating factor (GM-CSF) as described in detail by Inaba, et al. (1992).

I.2. Sensitization of Macrophages and Antigen Presenting Cells With GRP94-Peptide Complexes APC are sensitized with GRP94 (preferably noncovalently) bound to antigenic molecules by incubating the cells in vitro with the complexes and a modulator. The APC are sensitized with complexes of GRP94 and antigenic molecules preferably by incubating in vitro with the GRP94-complex and a modulator at 37° C. for 15 minutes to 24 hours. By way of example but not limitation, $4 \times 10^7$ macrophages can be incubated with 10 microgram GRP94-peptide complexes per ml or 100 microgram GRP94-peptide complexes per mL and a modulator in an equimolar amount with respect to the GRP94-peptide complex at 37° C. for 15 minutes-24 hours in 1 mL plain RPMI medium. The cells are washed three times and resuspended in a physiological medium preferably sterile, at a convenient concentration (e.g., $1 \times 10^7$ /ml) for injection in a subject. Preferably, the subject into which the sensitized APCs are injected is the subject from which the APC were originally isolated (autologous embodiment).

Optionally, the ability of sensitized APC to stimulate, for example, the antigen-specific, class I-restricted cytotoxic T-lymphocytes (CTL) can be monitored by their ability to stimulate CTLs to release tumor necrosis factor, and by their ability to act as targets of such CTLs.

I.3. Reinfusion of Sensitized APC

The sensitized APC are reinfused into the subject systemically, preferably intravenously, by conventional clinical procedures. These activated cells are reinfused, preferentially by systemic administration into the autologous subject. Subjects generally receive from about $10^6$ to about $10^{12}$ sensitized macrophages, depending on the condition of the subject. In some regimens, subjects can optionally receive in addition a suitable dosage of a biological response modifier including but not limited to the cytokines IFN-α, IFN-γ, IL-2, IL-4, IL-6, TNF or other cytokine growth factor.

J. Autologous Embodiment

The specific immunogenicity of an Hsp90 protein derives not from Hsp90 protein per se, but from the peptides bound to them. In a preferred embodiment of the invention directed to the use of autologous complexes of GRP94-peptides as cancer vaccines wherein the immunogenicity has been enhanced with a modulator in accordance with the present invention, two of the most intractable hurdles to cancer immunotherapy are circumvented. First is the possibility that human cancers, like cancers of experimental animals, are antigenically distinct. Thus, in an embodiment of the present invention, GRP94 chaperones antigenic peptides of the cancer cells from which they are derived and circumvent this hurdle.

Second, most current approaches to cancer immunotherapy focus on determining the CTL-recognized epitopes of cancer cell lines. This approach requires the availability of cell lines and CTLs against cancers. These reagents are unavailable for an overwhelming proportion of human cancers. Thus, in an embodiment of the present invention directed to autologous complexes of GRP94 and peptides, preferably wherein the immunogenicity has been enhanced with a modulator of the present invention, cancer immunotherapy does not depend on the availability of cell lines or CTLs nor does it require definition of the antigenic epitopes of cancer cells. These advantages make autologous Hsp90 proteins (e.g., GRP94) noncovalently bound to peptide complexes attractive and novel immunogens against cancer.

K. Prevention and Treatment of Primary and Metastatic Neoplastic Diseases

There are many reasons why immunotherapy as provided by the present invention is desired for use in cancer patients. First, if cancer patients are immunosuppressed and surgery, with anesthesia, and subsequent chemotherapy, can worsen the immunosuppression, then with appropriate immunotherapy in the preoperative period, this immunosuppression can be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

The preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication.

L. Monitoring of Effects During Cancer Prevention and Immunotherapy with Hsp90 Protein-Antigenic Molecule Complexes The effect of immunotherapy with GRP94-antigenic molecule complexes on development and progression of neoplastic diseases can be monitored by any methods known to one skilled in the art, including but not limited to measuring: 1) delayed hypersensitivity as an assessment of cellular immunity; 2) activity of cytolytic T-lymphocytes in vitro; 3) levels of tumor specific antigens, e.g., carcinoembryonic (CEA) antigens; 4) changes in the morphology of tumors using techniques such as a computed tomographic (CT) scan; 5) changes in levels of putative biomarkers of risk for a particular cancer in individuals at high risk, and 6) changes in the morphology of tumors using a sonogram.

Delayed Hypersensitivity Skin Test. Delayed hypersensitivity skin tests are of great value in the overall immunocompetence and cellular immunity to an antigen. Inability to react to a battery of common skin antigens is termed anergy (Sato et al. (1995) *Clin Immunol Pathol* 74:35-43). Proper technique of skin testing requires that the antigens be stored sterile at 4° C., protected from light and reconstituted shortly before use. A 25- or 27-gauge needle ensures intradermal, rather than subcutaneous, administration of antigen. Twenty-four and forty-eight hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate concentration.

Activity of Cytolytic T-lymphocytes In vitro. $8\times10^6$ peripheral blood derived T lymphocytes isolated by the Ficoll-Hypaque centrifugation gradient technique, are restimulated with $4\times10^4$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxicity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of about 12.5% (Heike et al. (1994) *J Immunotherapy* 15:165-174).

Levels of Tumor Specific Antigens. Although it can not be possible to detect unique tumor antigens on all tumors, many tumors display antigens that distinguish them from normal cells. Monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut an human colon cancer cells, but not on normal adult colon cells. Since CEA is shed from colon carcinoma cells and found in the serum, it was originally thought that the presence of this antigen in the serum could be used to screen subjects for colon cancer. However, subjects with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of subjects with liver and germinal cell tumors and can be used as a matter of disease status.

Computed Tomographic (CT) Scan. CT remains the choice of techniques for the accurate staging of cancers. CT has proved more sensitive and specific than any other imaging techniques for the detection of metastases.

Measurement of Putative Biomarkers. The levels of a putative biomarker for risk of a specific cancer are measured to monitor the effect of GRP94 noncovalently bound to peptide complexes. For example, in individuals at enhanced risk for prostate cancer, serum prostate-specific antigen (PSA) is measured by the procedure described by Brawer et al. (1992) *J Urol* 147:841-845 and Catalona et al. (1993) *JAMA* 270: 948-958; or in individuals at risk for colorectal cancer CEA is measured as described above; and in individuals at enhanced risk for breast cancer, 16-α-hydroxylation of estradiol is measured by the procedure described by Schneider et al. (1982) *Proc Natl Acad Sci USA* 79:3047-3051. The references cited above are incorporated by reference herein in their entirety.

Sonogram. A Sonogram remains an alternative choice of technique for the accurate staging of cancers.

M. Target Disorders/Traumas Associated with Ischemia

The present invention provides methods for treating and preventing ischemia-induced damage comprising administering a Hsp90 protein modulator to a subject wherein Hsp90 activity modulation is desired. The term "ischemia", as used herein, is a loss of blood flow to a tissue. Blood loss is characterized by deprivation of both oxygen and glucose, and leads to ischemic necrosis or infarction. Thus, the term "ischemia" refers to both conditions of oxygen deprivation and of nutrient deprivation. Loss of blood flow to a particular vascular region is described as "focal ischemia". Loss of blood flow to an entire tissue or body is referred to as "global ischemia".

The present invention provides therapeutic compositions and methods to ameliorate cellular damage arising from conditions of ischemia/reperfusion including but not limited to cardiac arrest, asystole and sustained ventricular arrythmias, cardiac surgery, cardiopulmonary bypass surgery, organ transplantation, spinal cord injury, head trauma, stroke, thromboembolic stroke, hemorrhagic stroke, cerebral vasospasm, hypotension, hypoglycemia, status epilepticus, an epileptic seizure, anxiety, schizophrenia, a neurodegenerative disorder, Alzheimer's disease, Huntington's disease, amyotrophic lateral sclerosis (ALS), neonatal stress, and any condition in which a neuroprotectant composition that prevents or ameliorates ischemic cerebral damage is indicated, useful, recommended, or prescribed.

The destructive effects of ischemia/reperfusion are manifest as a cascade of deleterious events that lead to cell death and ultimately organ failure. The metabolic events underlying ischemia-induced cell death include energy failure through ATP depletion, cellular acidosis, glutamate release, calcium ion influx, stimulation of membrane phospholipid degradation and subsequent free-fatty-acid accumulation, and free radical degeneration. Further, in contrast to apoptotic cell death, ischemia-induced cell death is characterized by degeneration of the most distal cell regions, and subsequent progressive degeneration of the cell soma and nucleus (Yamamoto et al. (1986) *Brain Res* 384:1-10; Yamamoto et al. (1990) *Acta Neuropathol* 80:487-492). Consistent with this degeneration profile, cells that bear extended processes, such as neuronal cells, are particularly sensitive to ischemic damage. Although not intended to be limited according to any particular theory, these observations suggest that intracellular transport and protein availability are essential components of cellular response to stress, and further implicate molecular components of such function, including Hsp90 proteins, as targets for ischemic response.

Thus, in one embodiment, the present invention pertains to the treatment of central nervous system ischemia. Examples of central nervous system ischemia include cerebral ischemic and spinal column ischemia. "Cerebral ischemia" is the interruption or reduction of blood flow in the arteries in or leading to the brain, usually as a result of a blood clot (thrombus) or other matter (embolus) occluding the artery.

A therapeutic composition of the present invention for the prevention or amelioration of ischemia-induced damage comprises a Hsp90 protein ligand. Preferably, such modulators promote or stabilize an active structural conformation of an endogenous Hsp90 protein. Also preferably, the Hsp90 ligand modulates the activity of GRP94 or HSP90. Desired properties of a composition having a cellular protectant effect include the following: (1) easy administration by oral or injectable routes (e.g., not significantly degraded in the stomach, intestine, or vascular system such that it reaches the tissues to be treated in a therapeutically effective amount), (2) therapeutic activity (e.g., efficacy) when administered following an ischemic insult, and (3) minimal or no side effects including impairment of cognition, disruption of motor performance, sedation, hyperexcitability, neuronal vacuolization, and impaired cardiovascular activity.

Compositions comprising Hsp90 protein ligands can be administered immediately following a trauma or other event that induces an ischemic condition. Alternatively, such a composition may be administered continuously or intermittently following detection of a progressive disorder, including but not limited to neurodegenerative diseases. In still another embodiment, such a composition may be administered to prevent or improve recovery from a subsequent ischemic condition. In each case, effective dose and administration profiles can be determined using standard experiments directed at such determination in animal models of ischemic conditions as disclosed in, for example, Tacchini et al. (1997) *Hepatology* 26(1):186-191 and U.S. Pat. Nos. 4,968,671, 5,504,090, and 5,733,916. Exemplary animal models are described herein below.

In another embodiment, the present invention pertains to treatment of tissue prior to transplantation. Such tissue is entirely devascularized following removal from the donor body. A therapeutic composition comprising a Hsp90 protein ligand can promote recovery and health of the transplanted tissue. Several methods for providing such a compound to donor or transplanted tissue are known in the art, including but not limited to administering the therapeutic compound that promotes organ preservation and health to a donor subject prior to procurance of the organ, perfusing an isolated organ with the therapeutic composition, and administering the composition to a transplant recipient prior, concurrent, or following tissue transplantation. See Mizoe et al. (1997) *J Surg Res* 73(2):160-165 and U.S. Pat. Nos. 5,066,578; 5,756,492; and 6,080,730.

In still another embodiment, a composition comprising a Hsp90 protein modulator can be repititiously provided to a subject in the absence of an ischemic condition, whereby the ability of the subject to tolerate a subsequent ischemic condition is enhanced. Therapeutic compositions comprising a Hsp90 ligand of the present invention can provide such a cellular protectant effect. Preferably, a dose of the therapeutic composition intended to induce ischemic tolerance would effect a mild ischemic condition as disclosed, for example, in Chen et al. (1996) *J Cereb Blood Flow Metab* 16:566-577 and U.S. Pat. Nos. 5,504,090 and 5,733,916.

M.1. In vivo Models of Ischemia

Numerous models of ischemic injury and disease are available for evaluating the therapeutic capacity of compositions comprising Hsp90 protein modulators. In addition to animal models described herein below, see also Massa et al. (1996) "The Stress Gene Response in Brain" in *Cerebrovascular and Brain Metabolism Reviews*, pp. 95-158, Lippincott-Raven Publishers, Philadelphia, Pa. and references cited therein. One skilled in the art will appreciate that alternative models can be used as disclosed. To assess therapeutic capacity, candidate compounds can be administered, for example, as a single dose given intraperitoneally immediately or 30 minutes after reinstating blood flow.

Transient Global Cerebral Ischemia. U.S. Pat. No. 5,571,840 discloses a dog model of cardiac arrest. According to this model, adult dogs are anesthetised and mechanically ventilated to maintain surgical anesthesia and suppression of corneal reflexes. Expired $CO_2$ tension and esophageal temperature are stably maintained before arrest and for at least one hour after resuscitation. Two venous catheters are inserted; one passed by way of the left external jugular vein to the right atrium for administration of resuscitation drugs, and the other into a muscular branch of the left femoral vein for fluid administration. Arterial blood pressure is measured through a catheter placed in a muscular branch of the left femoral vein for fluid administration. Arterial blood pressure is measured through a catheter placed in a muscular branch of the left femoral artery. Subcutaneous disk electrodes are placed to monitor an electrocardiogram (ECG).

Each animal is intravenously hydrated before arrest and during recovery. All catheters and electrical leads are passed subcutaneously to exit the skin in the dorsal midscapular region for later attachment to a dog jacket and hydraulic/electric swivel. Pulsatile and mean arterial blood pressure (MAP), ECG, and end-expiratory $CO_2$ can be continuously recorded on a six-channel oscillograph. At the conclusion of surgical instrumentation, anesthesia is discontinued and ventilation proceeds with room air. When corneal reflexes are apparent, the heart is fibrillated by delivering a 10-15 second, 60 Hz, 2 msec square-wave stimulus to the left ventricular epicardium. Ventilation is discontinued and circulatory arrest is confirmed by ECG, MAP, and direct observation of the heart. After 9 minutes of normothermic ventricular fibrillation, ventilation is restored and direct cardiac massage is maintained MAP above 75 mmHg. Mechanical ventilation is continued until spontaneous ventilation ensues, but for not longer than 6 hours (typically only 30 minutes).

Conditions of stroke can be approximated by occlusion of the primary arteries to the brain. In one model, a bilateral common carotid artery occlusion is performed in the gerbil as further disclosed in Karpiak et al. (1989) *Ann Rev Pharmacol Toxicol* 29:403, Ginsberg & Busto (1989) *Stroke* 20:1627, and U.S. Pat. No. 6,017,965. Briefly, blood flow to the brain is interrupted for 7 minutes by clamping the carotid arteries. During the course of these experiments, the core body temperature of the animals is maintained at 37° C. to prevent a hypothermic reaction.

Permanent Focal Cerebral Ischemia. In another model of cerebral ischemia, the middle cerebral artery is occluded in rat as disclosed in Karpiak et al. (1989) *Ann Rev Pharmacol Toxicol* 29:403, Ginsberg & Busto (1989) *Stroke* 20:1627, Chen et al. (1996) *Mol Endocrinol* 10:682-693, and U.S. Pat. No. 6,017,965. According to this model, the middle cerebral artery is permanently occluded by passing a small piece of suture thread through the carotid artery to the region of the middle cerebral artery. Core body temperature is maintained at 37° C. This model is different from the bilateral common carotid artery occlusion in gerbil in eliciting a more restricted brain infarct, and thereby approximating a different kind of stroke (focal thrombotic stroke).

Transient Focal Cerebral Ischemia. In another model of focal cerebral ischemia in the rat, the middle cerebral artery is temporarily occluded by passing a small piece of suture thread through the carotid artery to the region of the middle cerebral artery. The suture thread is withdrawn after an ischemic period of 2 hours. Core body temperature is maintained at 37° C.

Additional models of focal ischemia include, but are not limited to, photochemically induced focal cerebral thrombosis, blood clot embolization, microsphere embolization and related methods. See McAuley (1995) *Cerebrovasc Brain Metab Review* 7:153-180.

Renal Ischemia. Adult male rats are anesthetized with phenobarbital (50 mg/kg) and the body temperature of rats is maintained between 36-37° C. Renal ischemia is induced by clamping the left renal artery for 15 minutes (mild ischemia) or 45 minutes (severe ischemia), followed by reperfusion for 5 hours, as disclosed in Kuznetsov (1996) *Proc Natl Acad Sci USA* 93:8584-8589.

M.2. In vitro Models of Ischemia

Cell Culture Model of Epithelial Ischemia. Canine kidney (MDCK) cells are grown in Dulbecco's minimal essential medium supplemented with 5% fetal bovine serum. Rat thyroid (PCC13) cells are grown in Coon's modified Ham's F-12 medium (Sigma of St. Louis, Mo.) supplemented with 5% bovine calf serum and a hormone mixture as described in Grollman et al. (1993) *J Biol Chem* 268:3604-3609. Cultured MDCK or PCC13 cells are subjected to inhibition of oxidative metabolism by treatment with antimycin A, a specific inhibitor of mitochondrial oxidative phosphorylation as disclosed in Ramachandran & Gottlieb (1961) *Biochim Biophys Acta* 53:396-402. Alternatively, or in addition, the cells can be treated with 2-deoxyglucose, a nonhydrolyzble analog of glucose, to inhibit glycolytic metabolism. See Bacalloa et al. (1994) *J Cell Sci* 107:3301-3313, Mandel et al. (1994) *J Cell Sci* 107:3315-224, and Kuznetsov (1996) *Proc Natl Acad Sci USA* 93:8584-8589.

Cell Culture Model of Oxygen and Glucose Deprivation. Chinese hamster ovary (CHO) cells are grown in Ham's F-10 medium containing 15% newborn calf serum (GibcoBRL of Gaithersburg, Md.). Cells (5 ml) are seeded at a density of 150,000 cells per ml to T25 flasks (Corning of Acton, Mass.) and are used for experiments in a subconfluent state approximately 48 hours later. To achieve glucose deprivation, 15% serum is added to F-10 medium prepared without glucose, resulting in a partially glucose deficient broth. During incubation, cells use the remaining glucose after about 20 hours, as can be determined using a Sigma glucose colorimetric assay kit. Glucose-deprived cells are harvested after an additional 24 hours of incubation.

To achieve anoxia, cultures in fell medium (or in full medium containing 50% additional glucose) were placed in a sealed Brewer jar (Baltimore Biological Laboratory, Microbiology Systems of Baltimore, Md.) and anaerobiosis was initiated by using a hydrogen generator in a 4-7% carbon dioxide atmosphere as described previously by Anderson & Matovcik (1977) *Science* 197:1371-1374 and Seip & Evans (1980) *J Clin Microbiol* 11:226-233. The oxygen concentration in the jar is decreased to <0.4% in 100 minutes, and the concentration of oxygen at cell depth in a nonagitated solution is calculated to be within 1% of the environmental value within 30 minutes. Such a calculation can be made according to the methods described in Gerweck et al. (1979) *Cancer Res* 39:966-972. The formation of water vapor from hydrogen and oxygen causes a brief (about 15 minute) temperature increase to about 38.6° C. in the culture medium soon after initiation of anaerobiosis. This increase is insufficient to elicit a heat-shock response.

Anoxia can be verified using a methylene blue indicator solution. This solution becomes colorless (indicating the absence of oxygen) 5-6 hours after the initiation of anaerobiosis. A constant glucose concentration (1 g/L) can be maintained by changing the medium at 24 hours prior to and immediately prior to the initiation of anaerobiosis.

Cell Culture Model of Cerebral Ischemia. Isolated neurons can be cultured on a monolayer comprising a growth-permissive substrate, such as an immobilized monolayer of a purified, growth-promoting factor, such a monolayer comprising collagen, fibronectin, of the L1 glycoprotein. As an exemplary procedure, neurons (post-natal days 2-7) are dissociated by trypsinization essentially as described, for example, in U.S. Pat. No. 5,932,542. Neurons are added to a well coated with a growth-promoting factor, followed by addition of either a single concentration or increasing concentrations of the candidate composition. Neurons are cultured overnight (about 16 hours) at 37° C., and then neurite outgrowth is measured. Hypoxia/anoxia can be achieved as described herein above. Neurite outgrowth of cells subjected to ischemic conditions and to which a candidate therapeutic composition was administered can then be compared to neurite outgrowth on control cells also subjected to ischemic conditions without administration of a therapeutic composition.

Cell Culture Model of Glutamate-induced Oxidative Toxicity in Hippocampus. Glutamate is the major excitatory transmitter in the brain, and is proposed to play a role in epileptic pathogenesis and seizure activity. Numerous in vivo models involving different kinds of seizures and behavioral effects that are relevant for clinically distinct forms of epilepsy are known. In vitro models of glutamate-induced oxidative toxicity are also known, an exemplary procedure described herein. The mouse hippocampal cell line (Davis & Maher (1994) *Brain Res* 652(1):169-173) is maintained in Dulbecco's modified Eagles' medium (GibcoBRL of Gaithersburg, Md.) with 10% fetal bovine serum (Atlanta Biologicals of Atlanta, Ga.). HT22 cells are seeded onto 96-well plates at 20,000 cells per well and cultured overnight at 37° C. in normal growth medium. Glutamate-induced oxidative toxicity is elicited by administration of 2-10 mM glutamate or NMDA. Further methods are disclosed in Su et al. (1998) *J Mol Cell Cardiol* 30(3):587-598; Xiao et al. (1999) *J Neurochem* 72:95-101, and U.S. Pat. No. 6,017,965.

M.3. Assays for Recovery Following Ischemia or Other Stress Conditions

The effects of therapeutic compositions disclosed herein, may be examined to determine potential therapeutic strategies for mitigating and/or reversing cellular damage in these animal models. Exemplary, although not limiting, measures to assess therapeutic efficacy as disclosed herein below.

Neurological Assessment Assay. Neurological deficit and recovery can be monitored using standardized scores that represent careful observation of consciousness, respiration, cranial nerve activity, spinal nerve activity, and motor function, as disclosed in U.S. Pat. No. 5,571,840. Interobserver variability can be resolved by consultation of the detailed description of each neurological function. Additional assays of cognitive, sensory, and motor impairment are disclosed in U.S. Pat. No. 6,017,965.

Infarct Size Assay. The efficacy of candidate compounds disclosed herein can also be evaluated by determination of infarct size following administration of the composition to an animal subjected to ischemic conditions. At a selected timepoint(s) following initiation of ischemic conditions, such an animal is sacrificed and processed for routine histology suitable for the tissue of interest and according to methods well-known in the art Image processing software (e.g. Bio Scan OPTIMAS of Edmonds, Wash.) can be utilized to facilitate accurate calculation of infarct volume.

Detection of Molecular Markers for Cell Degeneration. In another embodiment, damaged tissue can be identified in brain sections by immunolabeling with antibodies that recognize antigens such as Alz-50, tau, A2B5, neurofilaments, neuron-specific enolase, and others that are characteristic of neurodegeneration as disclosed in U.S. Pat. No. 6,046,381. Immunolabeled cells can be quantified using computer-aided semiquantitative analysis of confocal images.

Cell Viability Assay. When in vitro models of ischemia are employed, cell viability can be assessed by measuring cell ability to metabolize 3-(4,5-dimethyidiazol-2-yl)-2,5-dipehnyltetrazolium bromide (MTT) as described in Hansen et al. (1989) *Electrophoresis* 10:645-652. Briefly 10 μl of MUT solution (5 mg/ml) is added to cell cultures is 96-well plates and the cells are maintained in normal growth medium for 4 hours at 37° C. Solubilization solution (100 μl; 50% dimethylformamide and 20% sodium dodecyl sulfate, pH 4.8) is then added directly to each culture in individual wells of the 96-well plate. After an overnight incubation at room temperature, absorbance is measured.

Alternatively, cell viability can be assessed by measuring the release of lactate dehydrogenase, a cytoplasmic enzyme that is released from dying cells as disclosed in Choi et al. (1987) *J Neurosci* 7:357 and U.S. Pat. No. 6,017,965.

Neuronal Growth Assays. A cell culture model of neural ischemia as described herein above can be evaluated by visual examination of labeled neuronal processes, and quantitation of the length, density, and dynamicism of neuronal processes (e.g. dendrites and spines) as disclosed in Horch et al. (1999) *Neuron* 23:353-364 and McAllister et al. (1997) *Neuron* 18:767-778.

In another embodiment, molecular markers can be used to evaluate neurite growth in fixed brain tissue section. For example, brain sections derived from an animal model of ischemia can labeled using antibodies that recognize MAP-2 (a marker of neuronal cell bodies and dendrites) and for synaptophysin (a marker of presynaptic terminals). Labeled sections can be viewed on a confocal microscope and documented using computer-aided semiquantitative analysis of confocal images. The area of the neuropil occupied by MAP-2-immunolabeled dendrites or by synaptophysin-immunolabeled terminals can be quantified and expressed as a percentage of the total image area. See Masliah et al. (1992) *Exp Neurol* 136:107-122 and Toggas et al. (1994) *Nature* 367: 188-193.

Additional methods for assaying neuronal growth are disclosed in Doherty et al. (1995) *Neuron* 14:57-66, Schnell et al. (1990) *Nature* 343:269-272, U.S. Pat. Nos. 5,250,414 and 5,898,066, and International PCT Publication WO 99/61585.

N. Disorders of Protein Transport

Protein misfolding disorders are a common component of numerous genetic disease states including, but not limited to, cystic fibrosis, familial hypercholesterolemia, retinitis pigmentosa and α1-antitrypsin misfolding. Compounds that modulate the activity of the Hsp90 family of molecular chaperones can thus be used in accordance with a therapeutic method of the present invention for reversing the protein folding defects that identify the disease state or for enhancing protein transport from the endoplasmic reticulum of a cell. Thus, a compound that modulates the conformation of GRP94 can be used to treat a disease state resulting from defects in protein transport into or from the endoplasmic reticulum. Compounds that abrogate GRP94 activity can be used for the treatment of a disease state, such as cancer, wherein a therapeutic benefit can be provided by blocking the egress of proteins (e.g., growth factors) from the endoplasmic reticulum. conversely, compounds that promote GRP94 activity can be used to treat a disease wherein a therapeutic benefit can be provided by enhancing protein export from the endoplasmic reticulum.

To assess misregulation of protein transport, a model system that measures epidermal growth factor receptor (EGF-R) levels and/or intracellular localization can be employed (Supino-Rosin et al. (2000) *J Biol Chem* 275(29):21850-21855). For example, the benzoquinone ansamaycin geldanamycin targets two Hsp90 molecular chaperones (Hsp90 and GRP94) and by inhibiting their activities, blocks and promotes its subsequent proteolytic degradation. In response to geldanamycin treatment, EGF-R is unable to traffic to the plasma membrane and the cell becomes refractory to stimulation by EGF.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Examples 1-8

Ligand-Mediated Activation of GRP94 Molecular Chaperone Activity

The amino terminal domain of Hsp90 chaperones contains an adenosine nucleotide binding pocket that binds the Hsp90 inhibitors geldanamycin and radicicol. The following Examples 1-8 demonstrate that bis-ANS (1-1' bis(4-anilino-5-napthalenesulfonic acid)), an environment-sensitive fluorophore that interacts with nucleotide binding sites, binds to the adenosine nucleotide binding domain of GRP94 and activates its peptide binding and molecular chaperone activities. Bis-ANS, like heat shock, elicits a tertiary conformational change in GRP94 which activates GRP94 function and is inhibited by radicicol. Confirmation of the N-terminal nucleotide-binding domain as the bis-ANS binding site was obtained by sequencing of bis-ANS-labeled GRP94 protease digestion products. These data identify a ligand-dependent, allosteric regulation of GRP94 and suggest a model for ligand-mediated regulation of GRP94 function.

Materials and Methods for Examples 1-8

Materials. Fluorescent probes were obtained from Molecular Probes (Eugene, Oreg.). Bis-ANS concentration was determined by absorbance at 385 nm ($\epsilon_{385}$=16,790 cm$^{-1}$ M$^{-1}$ in water). Citrate synthase (E.C. 4.1.3.7) was purchased from Boehringer Mannheim (Mannheim, Germany). Radicicol was obtained from Dr. Len Neckers, National Cancer Institute, Frederick, Md. Peptide VSV8 (RGYVYQGL—SEQ ID NO: 1) was synthesized by the University of North Carolina at Chapel Hill Peptide Synthesis Facility (Chapel Hill, N.C.). Na [$^{125}$I] was purchased from Amersham Pharmacia (Piscataway, N.J.). All other reagents were obtained from Sigma Chemical Co. (St. Louis, Mo.) unless otherwise indicated. GRP94 was purified from porcine pancreas as described by Wearsch & Nicchitta (1996b) *Biochemistry* 35:16760-16769. The concentration of GRP94 was determined by absorbance at 280 nm (1 mg/ml=1.18A$_{280}$).

Fluorophore Binding Reactions. All binding reactions, with the exception of the indicated circular dichroism and citrate synthase aggregation experiments, were conducted in buffer A (110 mM KOAc, 20 mM NaCl, 2 mM Mg(OAc)$_2$, 25 mM K-HEPES pH 7.2, 100 µM CaCl$_2$). Fluorescent probe and radicicol stocks were prepared in dimethyl formamide at 5 mM final concentration. For all assays, control reactions at solvent dilutions identical to experimental conditions were performed to correct for any solvent effects. Where indicated, GRP94 was heat shocked by incubation in a 50° C. water bath for 15 minutes followed by cooling to 37° C.

Fluorescence Measurements. Emission spectra were obtained in a FLUOROMAX™ spectrofluorometer (SPEX Industries Inc. of Edison, N.J.) operating in photon counting mode. Spectra were recorded and processed with DM3000 f operating software, version 2.1 (SPEX Industries Inc. of Edison, N.J.). For emission scans, slit width was set at 1 nm. Excitation wavelengths were as follows: Prodan, 360 nm; ANS, 372 nm; bis-ANS, 393 nm; tryptophan, 295 nm. All spectra were background corrected.

Circular Dichroism Measurements. Far-UV CD spectrometry was performed on an AVIV Associates 62DS™ circular dichroism spectrometer (AVIV Associates of Lakewood, N.J.). Samples were analyzed in a 1 mm path length quartz cuvette at 37° C. GRP94 samples (1 µM) were prepared in standard phosphate buffered saline solution as buffer A produced unacceptable dynode voltages in the relevant region of the spectrum. GRP94 was incubated with 10 µM bis-ANS for 2 hours at 37° C. prior to obtaining spectra. Spectra were recorded from 300 to 195 nm. The α-helical content of GRP94 was calculated from the molar ellipticity at 222 nm. See Myers & Jakoby (1975) *J Biol Chem* 250:3785-3789.

Conformational Analysis by Proteolysis. The conformational state of GRP94 was assessed by tryptic digestion of the protein and subsequent SDS-PAGE analysis. For simple proteolysis experiments, 10 µl of a 0.5 mg/ml GRP94 stock, with or without prior heat shock, was combined with 1 µl bis-ANS and/or radicicol stock solutions and incubated for the indicated times at 37° C. Samples were then combined with 0.1% trypsin and digested for 30 minutes at 37° C. An equal volume of SDS-PAGE sample buffer was added and the samples were snap frozen in liquid nitrogen. Immediately prior to gel analysis, samples were thawed and boiled for 5 minutes. Samples were then separated on 12.5% SDS-polyacrylamide gels. Gels were fixed and stained with Coomassie Blue. For time course experiments, excess free bis-ANS was removed immediately prior to trypsinization by gel filtration on 0.5 ml G-25 SEPHADEX® spin columns.

Identification of the bis-ANS binding site. The bis-ANS binding region of GRP94 was identified by covalent incorporation of bis-ANS into GRP94 following bis-ANS photolysis procedures described by Sharma et al. (1998) *J Biol Chem* 273(25):15474-78 and Seale et al. (1998) *Methods Enzymol* 290:318-323. Briefly, 50 µg of GRP94 was combined with 50 µM bis-ANS in a final volume of 100 µl and photocrosslinked for 15 minutes on ice with a 366 nm hand-held UV lamp (Ultra-violet Products, Inc. of San Gabriel, Calif.). Following photocrosslinking, GRP94-bis-ANS complexes were digested with trypsin for one hour at 37° C. The trypsin-derived limit digestion products were then separated by C-18 reverse phase HPLC using a continuous acetonitrile/water gradient in 20 mM ammonium bicarbonate, with sequential detection by UV absorbance (220 nm) and fluorescence emission (excitation 418 nm; emission 498 nm). The major resultant fluorescent peak was collected and the corresponding peptide sequenced by Edman degradation on an Applied Biosystems PROCISE™ model 492 automated protein sequencer.

Native Blue Electrophoresis. The oligomeric state of GRP94 was assayed by blue native polyacrylamide gel electrophoresis (BN-PAGE) as described by Schagger et al. (1994) *Anal Biochem* 217:220-230. GRP94 was either heat shocked or exposed to a 10-fold molar excess of bis-ANS for the indicated times. Samples were then dissolved in 15% glycerol and loaded onto 5-18% gradient gels with 0.02%

Coomassie Brilliant Blue in the cathode buffer. Gels were run at 4° C., stained with Coomassie Blue, destained and dried.

Citrate Synthase Aggregation Assays. The effects of GRP94 on the thermal aggregation of citrate synthase were assayed by the methods described by Buchner et al. (1998) *Methods Enzymol* 290:323-338. Samples containing no protein, or GRP94 (1 µM), were incubated in 40 mM HEPES pH 7.5 for two hours at 37° C. with either 0.2% DMF or 10 µM bis-ANS. The samples were then warmed to 43° C. for five minutes and placed in a spectrofluorometer thermostatted at 43° C. Citrate synthase was then added to 0.15 µM final concentration and the thermal aggregation of the enzyme followed by light scattering. Excitation and emission wavelengths were both 500 nm with 2 nm slit width. The time course of citrate synthase aggregation was followed for 1000 seconds.

Peptide Binding to GRP94. Iodination of VSV8 was performed by the IODOBEADS™ procedure (Pierce Chemical Co. of Chicago, Ill.), and unincorporated [$^{125}$I] was removed by fractionation on a SEP-PAK™ C18 reverse-phase cartridge. Iodinated peptide was mixed with unlabeled peptide to yield a final specific activity of 6.0 µCi/mg. GRP94 (4.7 µg, final concentration 0.5 µM) was incubated with an equimolar quantity of bis-ANS in 0.1% DMF in 100 µL buffer A for 3.5 hr at 37° C. Samples were then incubated for an additional 30 min at 37° C., or heat shocked for 15 min at 50° C. and allowed to recover for 15 min at 37° C. A ten-fold molar excess of [$^{125}$I]VSV8 was added (final concentration 5 µM) and the mixture incubated for 30 min at 37° C. All incubations were performed in the dark to prevent bis-ANS degradation. Samples were then eluted on 1.2-mL SEPHADEX® G-75 spin columns pre-blocked with 75 µg BSA, and [$^{125}$I] was quantitated by gamma counting.

Example 1

Binding of Polarity-Sensitive Fluorescent Probes to GRP94

Recent studies on the conformational regulation of GRP94 have identified a tertiary structural change that occurs in response to heat shock and is associated with an activation of peptide binding activity. See Wearsch et al. (1998) *Biochemistry* 37(16):5709-16, Sastry & Linderoth (1999) *J Biol Chem* 274:12023-12035. Coincident with the heat shock-elicited conformational change, GRP94 displays enhanced binding of environment sensitive fluorescent probes such as Nile Red, which preferentially bind to hydrophobic domains (Wearsch et al., 1998). GRP94 contains two domains of significant hydrophobicity, a C-terminal assembly domain and a highly conserved N-terminal region, which corresponds to the Hsp90 geldanamycin and adenosine nucleotide binding site. See Stebbins et al. (1997) *Cell* 89:239-250; and Prodromou et al. (1997) *Cell* 90:65-75.

To characterize the structural basis for the heat shock dependent activation of GRP94 activity, the interaction of polarity-sensitive fluorophores with native and heat shocked GRP94 was examined. The three probes tested, Prodan (6-propionyl-2-(dimethylamino)naphthalene), 8-ANS (1,8-anilinonaphthalenesulfonate) and bis-ANS (bis(1,8-anilino-naphthalenesulfonate) are structurally related probes that bind to hydrophobic sites on proteins and undergo substantial fluorescence spectrum changes upon introduction into non-polar environments, as discussed by Rosen & Weber (1969) *Biochemistry* 8:3915-3920; Weber & Farris (1979) *Biochemistry* 18:3075-3078; Takashi et al. (1977) *Proc Natl Acad Sci USA* 74:2334-2338; Shi et al. (1994) *Biochemistry* 33:7536-7546. The following experimental protocol was utilized. GRP94 was warmed to 37° C. and either maintained at 37° C. or heat shocked for 15 minutes at 50° C., followed by incubation at 37° C. Subsequently, probe stocks were added to the GRP94 stocks and emission spectra recorded after 30 min at 37° C.

Figure 1B:
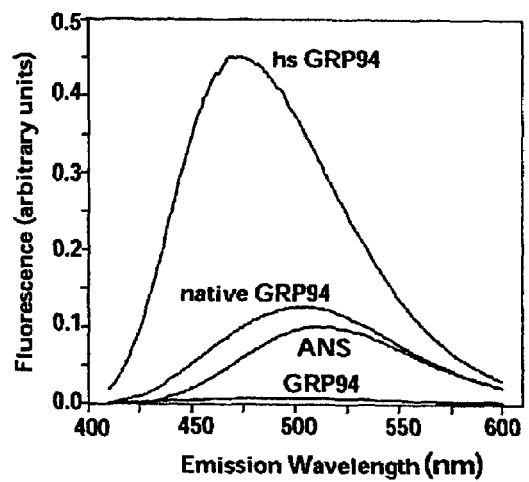
FIG. 1B is a graph depicting 8-ANS binding to GRP94, and dependence of such binding on GRP94 structural state. Fluorescence emission wavelength scans of 0.5 μM native or heat shocked (hs) GRP94 were performed following exposure to 5 μM 8-ANS for 30 minutes. Values represent the maximal fluorescence relative to that occurring with an identical concentration of heat shocked GRP94. Experiments were conducted at excitation wavelengths of 372 nm (8-ANS). All spectra were background corrected.

As depicted in FIG. 1A, the emission maxima of Prodan in the presence of native or heat shocked GRP94 were essentially identical, indicating that Prodan does not interact with the hydrophobic binding pocket(s) displayed by heat shocked GRP94. In contrast, the structurally related probe, 8-ANS, displays weak interactions with native GRP94, yet binds avidly following heat shock (FIG. 1B).

Figure 1C:
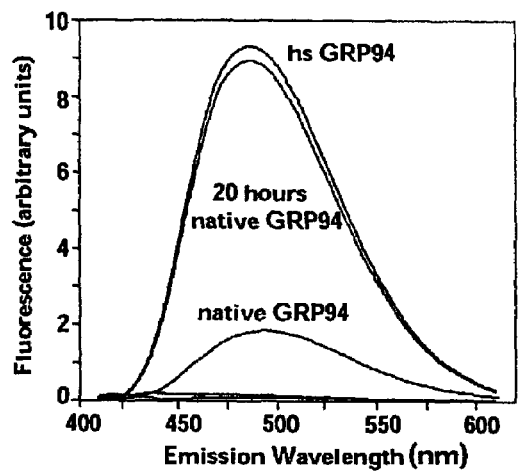
FIG. 1C is a graph depicting bis-ANS binding to GRP94, and dependence of such binding on GRP94 structural state. Fluorescence emission wavelength scans of 0.5 μM native or heat shocked (hs) GRP94 were performed following exposure to 5 μM bis-ANS for 20 hours. Values represent the maximal fluorescence relative to that occurring with an identical concentration of heat shocked GRP94. Experiments were conducted at excitation wavelengths of 393 nm (bis-ANS). All spectra were background corrected.
Figure 1D:
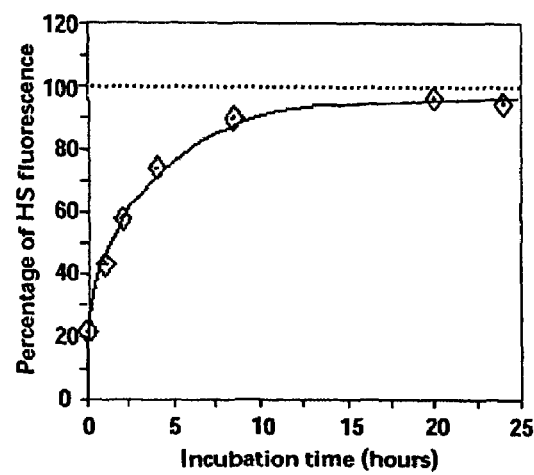
FIG. 1D is a graph depicting a time course of bis-ANS binding to GRP94. Values represent the maximal fluorescence relative to that occurring with an identical concentration of heat shocked GRP94. Experiments were conducted at excitation wavelengths of 393 nm (bis-ANS). All spectra were background corrected.

The interaction of bis-ANS with GRP94 was complex, and displayed a clear time dependence. As depicted in FIGS. 1C and 1D, the initial bis-ANS binding to native GRP94 was bi-phasic and following extended incubations in the presence of bis-ANS, a level of fluorophore binding similar to that seen with heat shocked GRP94 was observed. These data suggest that maximal bis-ANS binding to GRP94 required a slow structural transition. This transition further suggests a bis-ANS elicited conformational change in GRP94 and/or the bis-ANS dependent stabilization of a conformation state accessed at low frequency by the native protein.

Example 2

Analysis of bis-ANS Binding to Heat Shocked GRP94

Figure 2A:
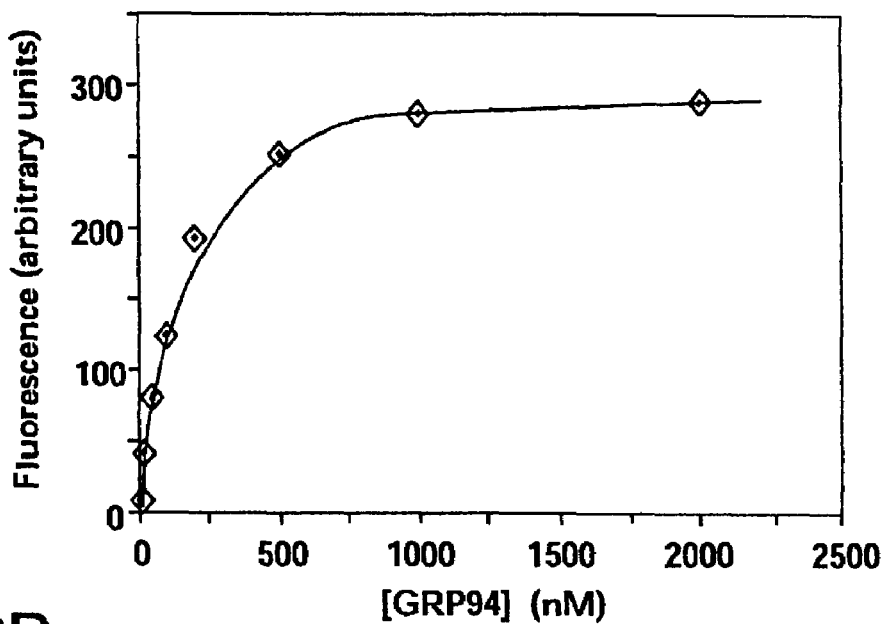
FIG. 2A is a graph depicting kinetic analysis of bis-ANS interactions with heat shocked GRP94. The concentration dependence of bis-ANS binding to heat shocked GRP94 was conducted under experimental conditions of fixed bis-ANS concentration (50 nM) and increasing GRP94 concentration, as indicated.
Figure 2B:
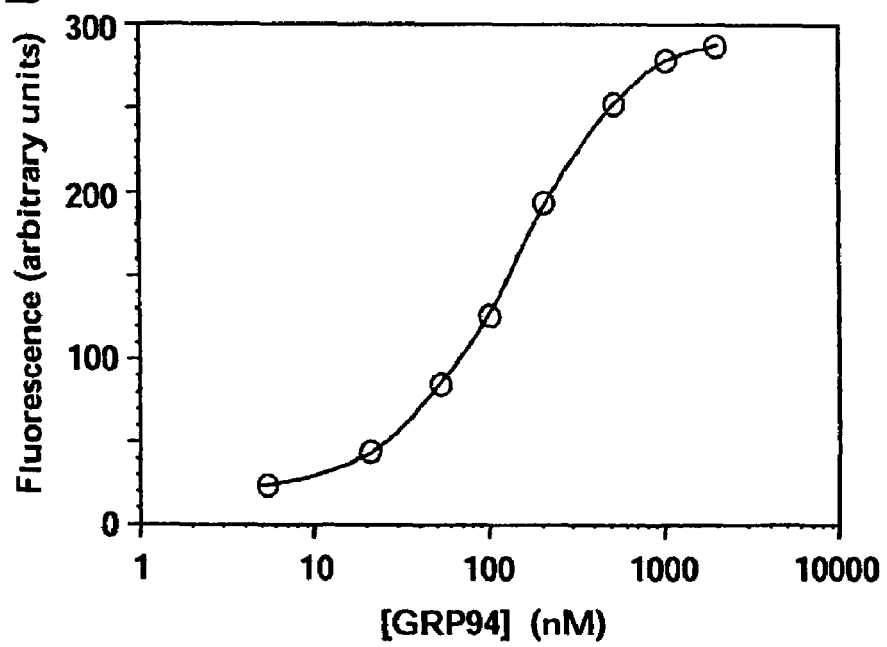
FIG. 2B is a Klotz plot representation of bis-ANS/GRP94 binding data. Half maximal binding occurs at 110 nM GRP94. Excitation wavelenth, 393 nm. Emission wavelength, 475 nm.

To determine the affinity of bis-ANS for GRP94, bis-ANS was added to increasing concentrations of heat shocked GRP94, the fluorescence spectrum was determined, and the emission intensity at 475 nm plotted as a function of GRP94 concentration (FIGS. 2A and 2B). Under the experimental conditions used in this series of experiments, bis-ANS binding to GRP94 was near maximal at a 20-fold molar excess of GRP94 monomer over bis-ANS, with half maximal binding observed at 110 nM GRP94 (FIG. 2B). Importantly, these data indicate that bis-ANS binds in a saturable manner to heat shocked GRP94 and that the site(s) of bis-ANS binding to GRP94 displayed similar relative affinities for bis-ANS.

Example 3

Structural Consequences of bis-ANS Binding to GRP94

Following an extended incubation period, the emission spectra of bis-ANS bound to native GRP94 bears substantial similarity to that emission spectra of bis-ANS bound to heat shocked GRP94. Because heat shock is known to elicit a stable tertiary conformational change in GRP94 (Wearsch et al. (1998) *Biochemistry* 37(16):5709-16) these data suggest that the binding of bis-ANS to GRP94 induces, or stabilizes, a conformational change similar to that occurring in response to heat shock. To determine whether the GRP94 conformation seen upon addition of bis-ANS is similar to that observed following heat shock, a series of structural studies on the bis-ANS/GRP94 complex was performed.

Figure 3:
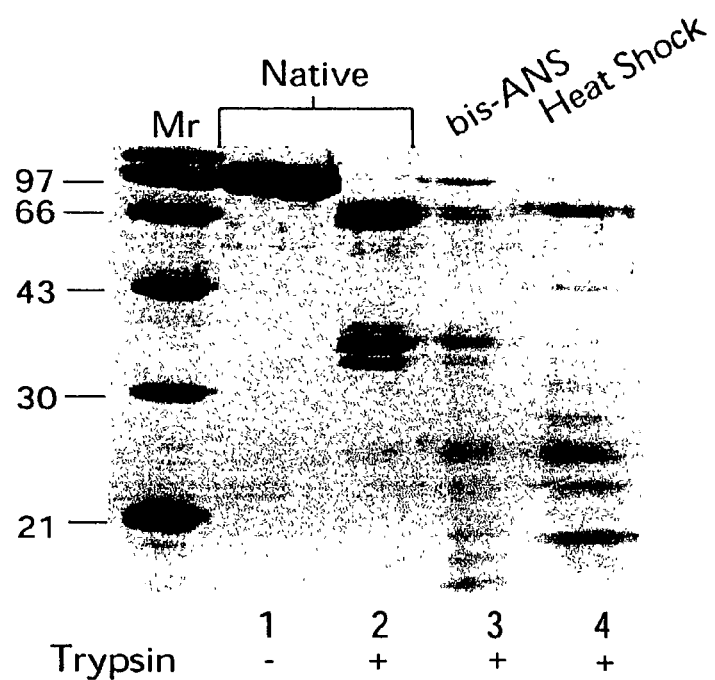
FIG. 3 is a digital image of a Coomassie Blue stained gel depicting that bis-ANS and heat shock increase GRP94 proteolysis sensitivity. GRP94 (5 µg, 5 µM) was incubated with 50 µM bis-ANS for one hour at 37° C. or heat shocked for 15 minutes at 50° C. Samples were then digested with 0.1% trypsin for 30 minutes at 37° C. and analyzed on 12.5% SDS-PAGE gels. Lane 1, 5 µg of undigested GRP94; lane 2, control native GRP94 incubated with trypsin; lane 3, bis-ANS treated GRP94 digested with trypsin; lane 4, GRP94 heat shocked then digested with trypsin.

In one series of experiments, the proteolysis patterns of native, heat shocked and bis-ANS treated GRP94 were examined. As shown in FIG. 3A, lanes 2 and 3, incubation of native GRP94 with low levels of trypsin yields two prominent proteolysis products, representing known structural domains of the protein, as described by Stebbins et al. (1997); Prodromou et al. (1997) *Cell* 90:65-75; Wearsch & Nicchitta (1996b)

Biochemistry 35:16760-16769. In contrast, proteolysis of either bis-ANS treated or heat shocked GRP94 yields a substantially reduced recovery of the prominent proteolysis products, with the concomitant appearance of a diverse array of proteolytic fragments of higher SDS-PAGE mobility. Essentially identical proteolysis patterns were observed following either heat shock or bis-ANS treatment of HSP90.

These data provide evidence that bis-ANS binding to GRP94 elicits or stabilizes GRP94 in a conformation similar to that occurring in response to heat shock, suggesting that there exists a GRP94 conformation state that can be readily accessed and/or stabilized by either heat shock or ligand (bis-ANS) binding.

Example 4

Effects of bis-ANS Binding on GRP94 Quaternary and Secondary Structure

Figure 4:
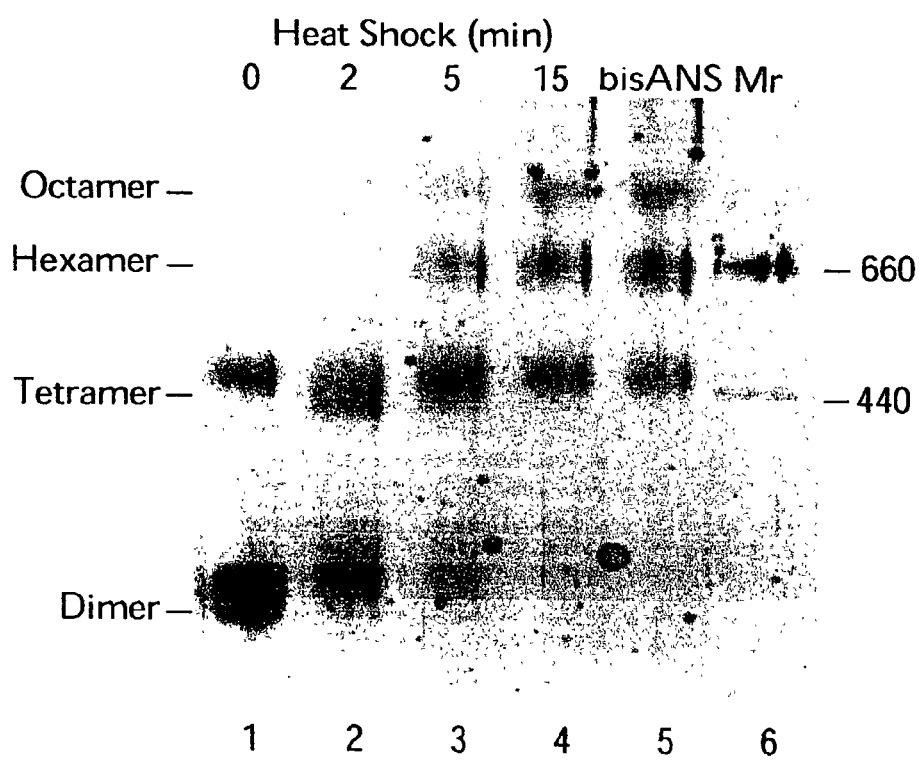
FIG. 4 is a digital image of a Coomassie Blue stained gel depicting that bis-ANS and heat shock induce GRP94 multimerization. GRP94 was heat shocked at 50° C. for 0-15 minutes or incubated with 10-fold molar excess of bis-ANS and the structural state of the protein analyzed on 5-18% native blue polyacrylamide gradient gels. The mobilities of GRP94 dimers, tetramers, hexamers, and octamers are shown. Molecular weight standards are indicated to the right of FIG. 4.

When purified from tissue, GRP94 exists as a homodimer, as described by Wearsch & Nicchitta (1996a) *Prot Express Purif* 7(1):114-21; Nemoto et al. (1996) *J Biochem* 120:249-256. Following heat shock however, GRP94 forms higher molecular weight complexes, as described by Wearsch et al. (1998) *Biochemistry* 37:5709-5719. To further characterize the effects of bis-ANS on GRP94 structure, the oligomerization states of native, heat shocked and bis-ANS treated GRP94 were assayed by the blue native polyacrylamide gel electrophoresis (BN-PAGE) technique described by Schagger et al. (1994). In these experiments, GRP94 was incubated with bis-ANS or briefly heat shocked and subsequently incubated at 37° C. The samples were then analyzed by BN-PAGE. As seen in FIG. 4, in the absence of heat shock or bis-ANS treatment the majority of GRP94 exists as a dimer with an apparent molecular weight of approximately 200 kDa. However, exposure to heat shock causes a relatively rapid formation of tetramers, hexamers, and octamers (FIG. 4, lanes 2-4). Incubation of GRP94 with a ten-fold molar excess of bis-ANS induces changes in the quaternary structure of GRP94 that mimic those seen upon heat shock (FIG. 4, lanes 4, 5). These data lend further support to the hypothesis that bis-ANS induces or stabilizes a structural transition in GRP94 that is similar to that occurring in response to heat shock.

Figure 5:
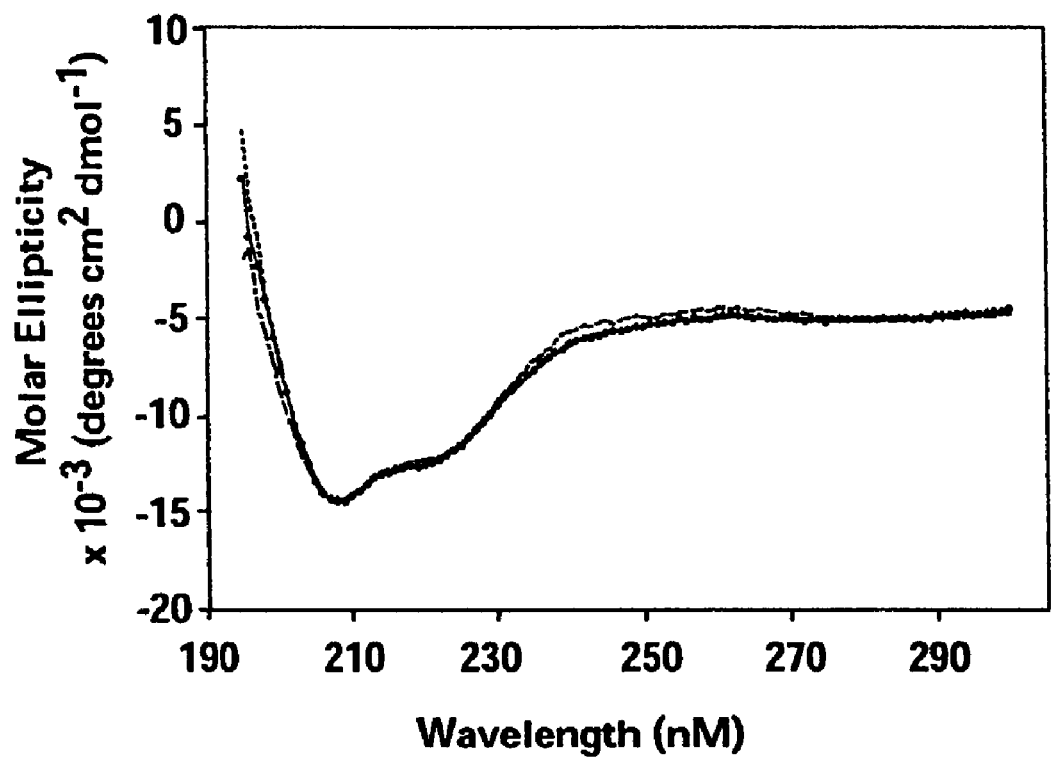
FIG. 5 is a graph depicting that circular dichroism spectra of native, heat shocked, and bis-ANS treated GRP94 are identical. Circular dichroism spectra of 1 µM GRP94 native (diamonds); heat shocked (dot and dash); and treated 2 hours with 10 µM bis-ANS (dotted) are shown. Spectra were collected as described in Examples 1-8 below.

To gain further insight into the nature of the bis-ANS dependent conformational change, GRP94 was subjected to heat shocked or treated with bis-ANS and far-UV CD spectra obtained (FIG. 5). As shown in FIG. 5, the CD spectra for native, heat shocked, and bis-ANS treated GRP94 were identical, indicating that bis-ANS binding does not alter GRP94 secondary structure.

Example 5

Radicicol Inhibits Temperature and bis-ANS Induced GRP94 Conformational Changes

Radicicol, a macrocyclic antibiotic, binds to the highly conserved N-terminal nucleotide binding pocket of HSP90 and thereby blocks HSP90 function. (Sharma et al. (1998) *Oncogene* 16(20):2639-45; Roe et al. (1999) *J Med Chem* 42:260-266). To determine if radicicol binding also influenced the structural dynamics of GRP94, the following experiments were performed. GRP94 was incubated with increasing concentrations of radicicol, heat shocked, cooled, and digested with trypsin. Subsequent SDS-PAGE analysis of the samples showed that in the presence of radicicol, GRP94 was unable to undergo the heat shock-induced structural transition, as assayed by the similarities in proteolysis patterns between native GRP94 and radicicol-treated, heat shocked GRP94. Similar inhibition of the heat shock induced structural transition of HSP90 by radicicol was also observed.

To determine if radicicol could also inhibit the bis-ANS dependent GRP94 structural transition, GRP94 was incubated with increasing concentrations of radicicol, bis-ANS was then added, and the samples were incubated for one hour. Samples were subsequently digested with trypsin and the proteolysis patterns determined by SDS-PAGE. As is depicted in FIG. 6A, radicicol, when present at a ten-fold molar excess over bis-ANS, efficiently blocked the bis-ANS-dependent GRP94 conformation change.

Figure 6A:
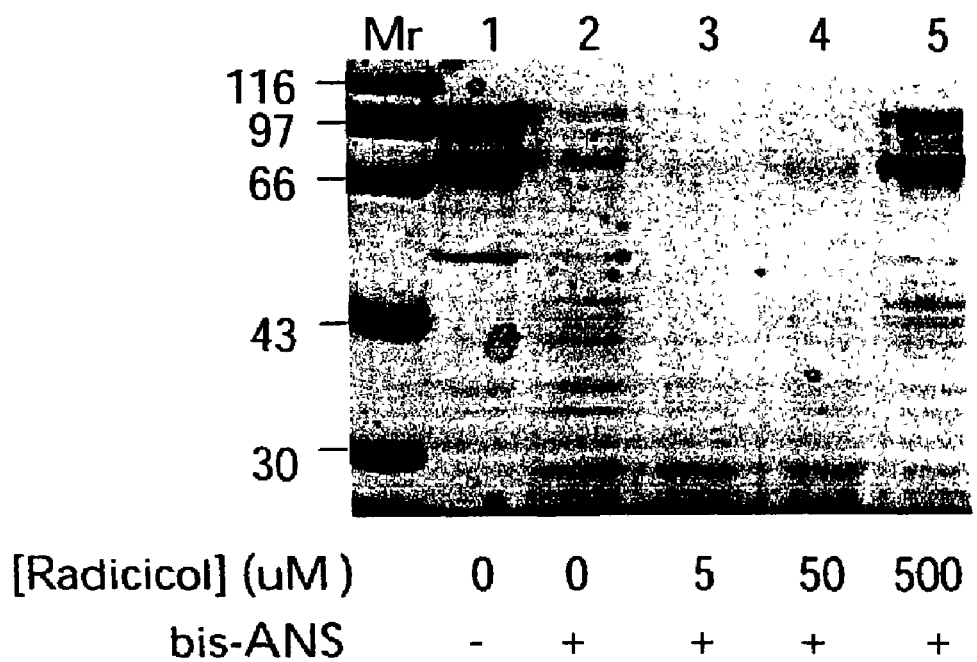
FIG. 6A is a digital image of a Coomassie Blue stained gel depicting that radicicol blocks bis-ANS structural transitions. GRP94 (5 µM) was preincubated for one hour at 37° C. with 0-500 µM radicicol and subsequently incubated for one hour at 37° C. with 50 µM bis-ANS, trypsinized, and the trypsin digestion pattern analyzed by SDS-PAGE.
Figure 6B:
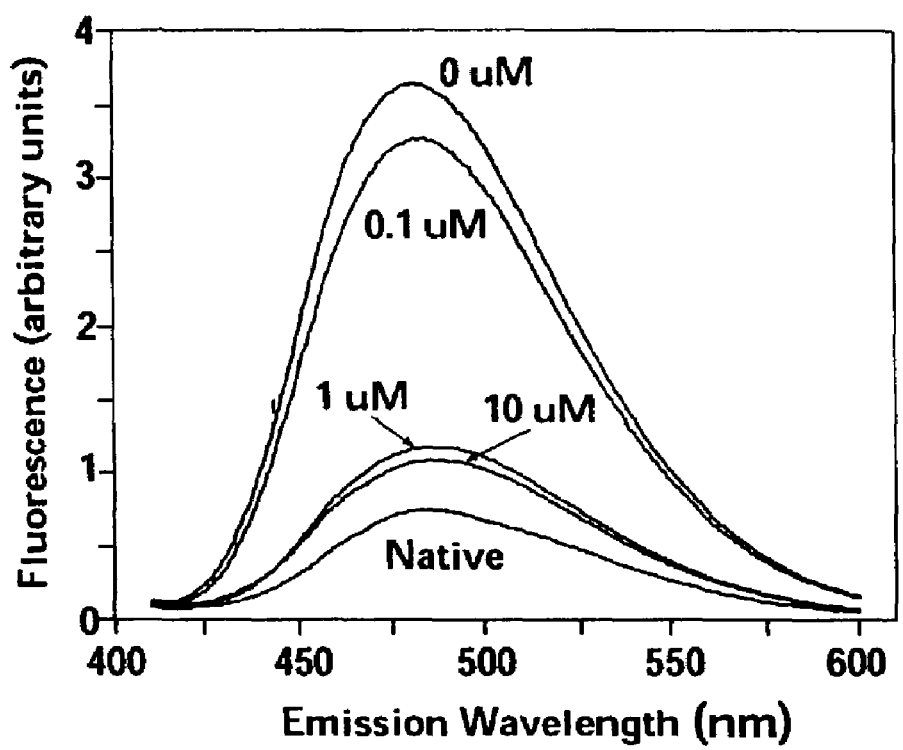
FIG. 6B is a graph depicting that radicicol blocks heat shock and bis-ANS binding. GRP94 (0.5 µM) was preincubated with 0-10 µM radicicol for one hour, heat shocked, and subsequently incubated with 1 µM bis-ANS. Bis-ANS binding was determined by spectrofluorometry with bis-ANS binding to native GRP94 in the absence of radicicol shown for comparison. Excitation 393 nm, emission 410-600 nm.

Though the experiment depicted in FIG. 6A indicated that radicicol was able to inhibit the appearance of the bis-ANS-dependent conformational state, it was necessary to determine if bis-ANS binding to GRP94 was blocked by radicicol treatment. To this end, the following experiment was performed. GRP94 was incubated in the presence of increasing concentrations of radicicol, subsequently heat treated under conditions sufficient to elicit efficient bis-ANS binding, and bis-ANS binding assayed. As shown in FIG. 6B, radicicol, in a dose-dependent manner, inhibited bis-ANS binding to heat-treated GRP94.

Because radicicol itself blocks the heat shock-induced conformation change, these data present two models of bis-ANS action. In one model, bis-ANS binds to the nucleotide binding domain and directly elicits the observed conformational change. Radicicol, by binding to the adenosine nucleotide binding pocket, would then be predicted to inhibit the bis-ANS-dependent conformational change. In an alternative model, GRP94 interconverts, in a temperature sensitive manner, between two conformational states, arbitrarily referred to as the open or the closed state. In the open state, bis-ANS bind and thereby stabilizes the open conformation whereas radicicol binding would stabilize the closed conformation. For both models, bis-ANS binding to the N-terminal adenosine nucleotide binding domain was predicted and was subsequently examined.

Example 6 bis-ANS binds to the N-terminal Adenosine Nucleotide/Radicicol/Geldanamycin Binding Domain Having determined that bis-ANS can alter the conformation of GRP94, the site of bis-ANS binding to GRP94 was targeted for identification. Irradiation of bis-ANS with UV light allows the covalent incorporation of the probe into protein binding sites, as described by Sharma et al. (1998) *J Biol Chem* 273(25):15474-78 and Seale et al. (1998) *Methods Enzymol* 290:318-323. As described in *Materials and Methods*, GRP94 was combined with an excess of bis-ANS and photo-crosslinked on ice for 15 minutes. GRP94 was subsequently digested with trypsin, the fluorescent peptides purified by HPLC, and the sequence of the labeled peptides determined by Edman sequencing. The major resultant fluorescent peptide yielded the sequence YSQFINFPIYV (SEQ ID NO: 2), which mapped to residues 271-281 of the N-terminal domain of GRP94. This segment is homologous to the human HSP90 sequence HSQFIGYPITLFV (SEQ ID NO: 3) from amino acids 210-222, and overlaps with the C-terminal region of the adenosine nucleotide/geldanamycin/radicicol binding domain (Stebbins et al. (1997) *Cell* 89:239-250; Prodromou et al. (1997) *Cell* 90:65-75).

Example 7

Bis-ANS Activates GRP94 Chaperone Activity

To determine if the bis-ANS-dependent conformational changes in GRP94 were of functional significance, the molecular chaperone activities of native, heat shocked and bis-ANS treated GRP94 were evaluated in a thermal aggregation assay, as described by Jakob et al. (1995) *J Biol Chem* 270:7288-7294 and Buchner et al. (1998) *Methods Enzymol* 290:323-338. In these experiments, citrate synthase aggregation was assayed in the presence of buffer, native GRP94, heat shocked GRP94 or GRP94 that had been previously exposed to bis-ANS for two hours. Following experimental treatment of the GRP94, reactions were equilibrated at 43° C., citrate synthase then added and aggregation, as represented by light scattering, was measured.

Figure 7A:
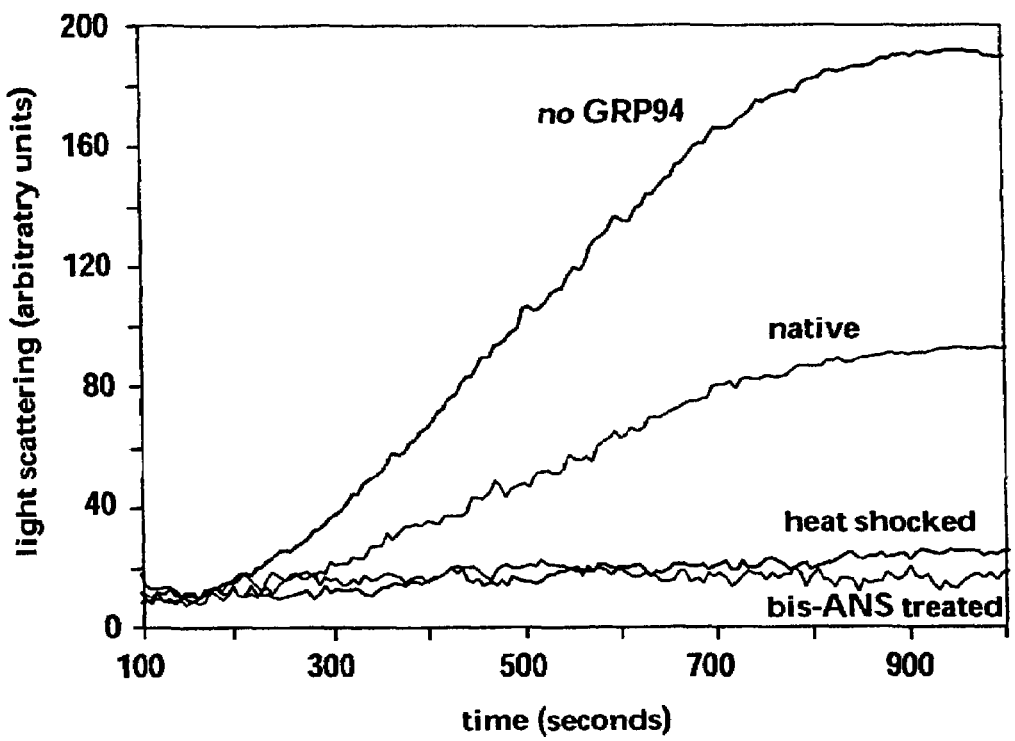
FIG. 7A is a graph depicting that bis-ANS and heat shock stimulate GRP94 chaperone activity. Citrate synthase enzyme was diluted to 0.15 µM into buffer containing no GRP94, 1 µM native GRP94, heat shocked GRP94, or GRP94 which had been preincubated for two hours with 10 µM bis-ANS, and citrate synthase aggregation at 43° C. was monitored by light scattering at 500 nm in a thermostatted spectrofluorometer.

In the absence of GRP94, citrate synthase undergoes rapid thermal aggregation and under the experimental conditions depicted in FIG. 7A, reaches a plateau level within 15 min. In the presence of native GRP94, the degree of aggregation is reduced, suggesting that at least a fraction of the population of native GRP94 molecules are in an active conformation. Under these experimental conditions, approximately 50% of the citrate synthase aggregated. At the concentration of GRP94 used in these experiments, and assuming a stoichiometric interaction, these results indicate that roughly 8% of the native GRP94 is in the active conformation. In the presence of heat shocked or bis-ANS treated GRP94, no thermal aggregation of citrate synthase was detectable (FIG. 7A). These data indicate that the ability of GRP94 to bind to substrate proteins is enhanced by prior heat shock or bis-ANS treatment and suggest that the GRP94 conformation elicited by heat shock or bis-ANS binding represents an active state of the molecule.

Example 8 bis-ANS Activates Peptide Binding Activity to GRP94

Figure 7B:
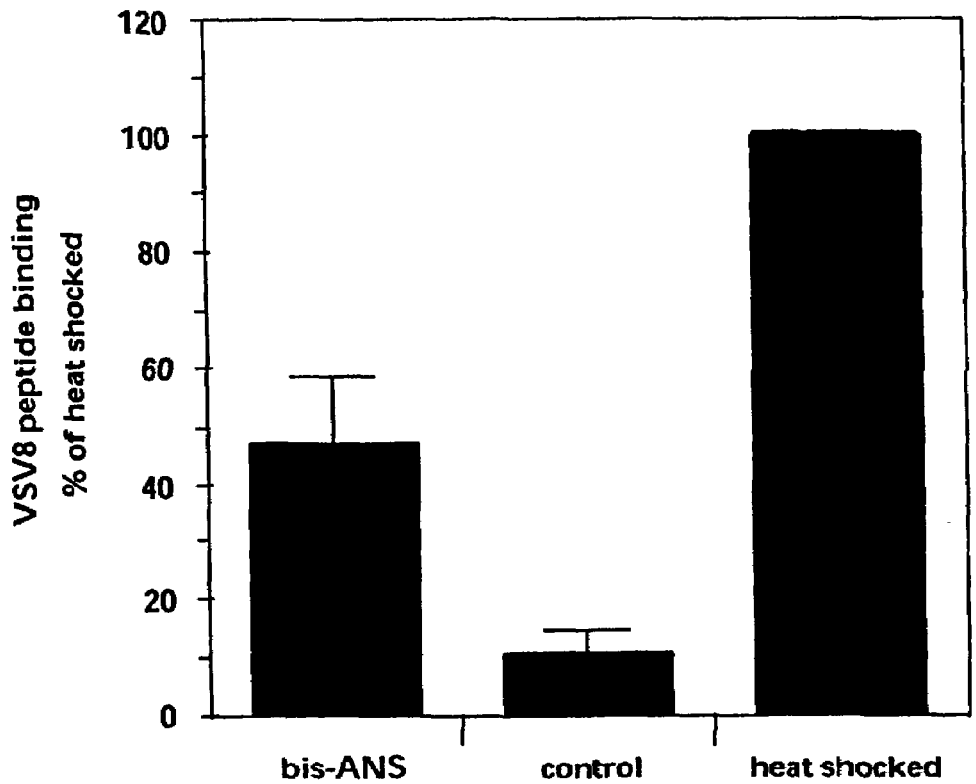
FIG. 7B is a bar graph depicting that bis-ANS and heat shock stimulate GRP94 peptide binding activity. Native, heat shocked, or bis-ANS treated GRP94 were incubated with a 10-fold molar excess of $^{125}$I-VSV8 peptide for 30 minutes at 37° C. Free peptide was removed by spin column chromatography and bound radioactive peptide quantitated by gamma counting.

To assess the effects of bis-ANS treatment on the peptide binding activity of GRP94, GRP94 was either treated with bis-ANS, or briefly heat shocked. A ten-fold molar excess of [$^{125}$I]-VSV8 was then added and the mixture incubated for 30 min at 37° C. Free peptide was separated from bound peptide by SEPHADEX® 75 spin column chromatography and the bound peptide was quantitated by gamma counting. As shown in FIG. 7B, treatment of GRP94 with bis-ANS significantly enhanced the peptide binding activity of GRP94, yielding approximately a four to five-fold stimulation over native protein. Under similar conditions, heat shocked GRP94 displayed approximately a ten-fold stimulation of binding. From the data presented in FIGS. 7A and 7B, it is apparent that bis-ANS elicits or stabilizes a GRP94 conformation that displays markedly enhanced molecular chaperone and peptide binding activities.

Summary of Examples 1-8

Examples 1-8 demonstrate that bis-ANS binds to the conserved, N-terminal adenosine nucleotide binding domain of GRP94 and elicits a tertiary conformational change yielding markedly enhanced molecular chaperone and peptide binding activities. The binding of bis-ANS to GRP94 is bi-phasic, with an initial rapid binding phase followed by a slow, extended binding phase. In accord with these data, bis-ANS binds to and stabilizes a low abundance GRP94 conformation, referred to as the open state. In this model, GRP94 molecular chaperone and peptide binding activity is intimately coupled to such a conformation change. While it is not applicants' desire to be bound by any particularly theory or act, in the absence of regulatory ligands, access to this conformation is believed to occur in a time and temperature-dependent manner through intrinsic structural fluctuations. Inhibitory ligands, such as geldanamycin and radicicol, function by binding to and stabilizing GRP94 in a closed, or inactive, conformation.

Summarily, Examples 1-8 disclose the identification of a ligand elicited conformational change in GRP94 that is accompanied by a marked activation of molecular chaperone and peptide binding activities. The similarities between the conformations of GRP94 following heat shock activation and bis-ANS binding support the conclusion that GRP94 conformation and activity can be regulated by ligand binding to the N-terminal adenosine nucleotide binding domain and that the conformation of the protein in the bis-ANS liganded state is physiologically relevant.

Examples 9-13

Allosteric Ligand Interactions in the Adenosine Nucleotide Binding Domain of the Hsp90 Chaperone, GRP94

Examples 9-13 disclose that GRP94 and HSP90 differ in their interactions with adenosine-based ligands. GRP94 displayed high affinity saturable binding of the adenosine derivative N-ethylcarboxamido-adenosine (NECA), whereas HSP90 did not. In NECA displacement assays, GRP94 exhibited weak binding affinities for ATP, ADP, AMP, adenosine and cAMP. GRP94 ATPase activity, though present, was non-saturable with respect to ATP concentration and thus could not be characterized by traditional enzymatic criteria. Radioligand and calorimetric studies of NECA binding to GRP94 revealed that ligand binding to the nucleotide binding domain is under allosteric regulation. GRP94 is thus regulated through a ligand-based allosteric mechanism and through regulatory adenosine-based ligand(s) other than ATP.

Materials and Methods for Examples 9-13

Purification of GRP94, BiP and Hsp90. GRP94 was purified from porcine pancreas rough microsomes as described by Wearsch & Nicchitta (1996a) *Prot Express Purif* 7:114-121 with the following modifications. Rough microsomes were washed after the initial isolation by 10-fold dilution in 0.25M sucrose, 20 mM KOAc, 25 mM K-Hepes, pH 7.2, 5 mM Mg(OAc)$_2$ and subsequent re-isolation by centrifugation (30 min, 40K rpm, 4° C., Ti50.2 rotor). To release the lumenal contents from the isolated rough microsomes, the microsomes were permeabilized by addition of 5 mM CHAPS and the lumenal contents were subsequently isolated by centrifugation for 2 hours at 45,000 RPM (4° C., Ti50.2 rotor).

BiP was purified by the following procedure. A lumenal protein fraction obtained from porcine pancreas rough microsomes was cycled overnight through a 1 ml ADP-agarose and a 1 ml ATP-agarose (Sigma Chemical Co. of St. Louis, Mo.) column coupled in series. The columns were then washed with 2×5 ml of a buffer containing 350 mM NaCl, 25 mM Tris, pH 7.8, 5 mM Mg$^{2+}$ and the BiP was eluted from the nucleotide affinity columns with 3×5 ml of the identical buffer supplemented with 10 mM ATP and ADP. The BiP containing fractions were identified by SDS-PAGE, and dialyzed against 2×4 L of buffer A (110 mM KOAc, 20 mM NaCl, 25 mM K-Hepes, pH 7.2, 2 mM Mg(OAc)$_2$ 0.1 mM CaCl$_2$). The protein sample was then applied to a SUPERDEX® 26/60 column (Amersham Pharmacia Biotech of Piscataway, N.J.) equilibrated in buffer A, and the BiP containing fractions, again identified by SDS-PAGE, were pooled and concentrated by centrifugal ultrafiltration (CENTRICON-30®; Amicon of Beverly, Mass.).

Hsp90 was purified from rat liver cytosol as follows. Cytosol was adjusted to 30% ammonium sulfate and stirred for 60 min on ice. The solution was centrifuged at 20,000×g in a Sorvall SS34 rotor for 15 minutes and the supernatant collected and filtered through a 0.22 µm filter. The filtered supernatant was supplemented with protease inhibitors (1 µg/ml pepstatin, 1 µg/ml leupeptin, 20 µg/ml SBTI, and 0.5 mM PMSF) and loaded onto a phenyl-SUPEROSE™ HR10/10 column (Amersham Pharmacia Biotech of Piscataway, N.J.). After washing, the bound proteins were eluted with a gradient of 30-0% saturated ammonium sulfate in 10 mM Tris/HCl, pH 7.5, 1mM EGTA, 0.5 mM DTT and the Hsp90 containing fractions were identified by SDS-PAGE. The Hsp90 containing fractions were then pooled and dialyzed 2×3 hr against 2 L of low salt buffer (10 mM NaCl, 25 mM Tris, pH 7.8). The dialyzed sample was then filtered through a 0.22 µm filter, and injected onto a MONO-Q™ HR 10/10 column (Amersham Pharmacia Biotech of Piscataway, N.J.) equilibrated in low salt buffer. The column was eluted with a gradient of 10 mM-750 mM NaCl in 25 mM Tris, pH 7.8. The Hsp90-containing fractions were identified by SDS-PAGE and pooled.

Further purification was achieved by applying the MONO-Q™ pool to a 4 mL hydroxylapatite column (Bio-Rad HTP of Hercules, Calif.) equilibrated in buffer B (10 mM NaH$_2$PO$_4$, pH 6.8, 10 mM KCl and 90 mM NaCl). The hydroxylapatite column was eluted with a 10 mM NaH$_2$PO$_4$ to 250 mM NaH$_2$PO$_4$, gradient and the Hsp90 fractions were identified by SDS-PAGE. The Hsp90 pool, in 225 mM NaH$_2$PO$_4$, 10 mM KCl, and 90 mM NaCl, was concentrated by centrifugal ultrafiltration (CENTRICON®-30; Amicon, Beverly, Mass.) and stored at −80° C.

[$^3$H]-NECA Binding Assay. Nine pg of GRP94 was incubated with 20 nM [$^3$H]-NECA (Amersham Pharmacia Biotech of Piscataway, N.J.), and various concentrations of competitors for one hour on ice in a final volume of 250 µl of 50 mM Tris, pH 7.5. Where indicated, binding reactions were performed in either buffer C (10 mM Tris, pH 7.5, 50 mM KCl, 5 mM MgCl$_2$, 2 mM DTT, 0.01% NP-40, 20 mM Na$_2$MoO$_4$) or 50 mM Tris, pH 7.5, 10 mM Mg(OAc)$_2$. Bound versus free [$^3$H]-NECA was assayed by vacuum filtration of the binding reactions on #32 glass fiber filters (Schleicher and Schuell of Keene, N.H.), pre-treated with 0.3% polyethyleneimine (Sigma Chemical Co. of St. Louis, Mo.). Vacuum filtration was performed with an Amersham Pharmacia Biotech (Piscataway, N.J.) vacuum filtration manifold.

Filters were rapidly washed with 3×4 ml of ice cold 50 mM Tris, pH 7.5, placed in 5 ml of scintillation fluid (SAFETY-SOLVE™, RPI of Mt. Prospect, Ill.), vortexed, and counted by liquid scintillation spectrometry. In experiments in which the kinetic parameters of [$^3$H]-NECA binding to GRP94 were determined, the chemical concentration and specific activity of NECA was adjusted by addition of unlabeled NECA. All binding reactions were performed in triplicate and corrected by subtraction of background values, determined in binding reactions lacking GRP94.

ATP Binding Assay. Six µg of GRP94, BiP, and Hsp90 was incubated with 50 µM yZ[$^{32}$P] ATP (1000 µCi/µmol) (Amersham Pharmacia Biotech of Piscataway, N.J.) in buffer B on ice for 1 hour. Nitrocellulose filters (BA85) (Schleicher & Schuell of Keene, N.H.) were individually wet in buffer B before use, and bound versus free [$^{32}$P]-ATP was separated by vacuum filtration. Filters were washed with 3×2 mL of ice cold buffer B, placed in 5 mL of scintillation fluid, vortexed, and counted.

Isothermal Titration Calorimetry. Isothermal calorimetry experiments were performed at 25° C. using a MSC calorimeter (MicroCal Inc. of Northampton, Mass.). To determine the NECA binding parameters, two 5 µl injections were followed by twenty-three 10 µL injections from a 152 µM NECA stock. The reaction chamber (1.3 mL) contained 5 µM GRP94. Necessary corrections were made by subtracting the heats of dilution resulting from buffer addition to protein solution and ligand solution into buffer. The corrected data were then fit by the ORIGIN™ software (Microcal Software, 1998) to obtain the binding parameters. The radicicol binding parameters were obtained in a similar manner with 5 µM GRP94 and 115 µM radicicol.

Phosphorylation Assays. To assay for GRP94 autophosphorylation, 1 µM GRP94 was incubated with γ-[$^{32}$P]ATP (6000 cpm/pmol) (Amersham Pharmacia Biotech of Piscataway, N.J.), diluted with cold ATP to yield a final concentration of 0.15 mM ATP in a buffer containing 10 mM Mg(OAc)$_2$ and 50 mM K-Hepes, pH 7.4. For the casein kinase assay, 1 unit of casein kinase II was incubated as described above, with the addition of 4 µM casein. Competitors were added to the appropriate samples to yield final concentrations of 180 µM NECA in 3.6% DMSO, 180 µM radicicol in 3.6% DMSO, 5 µg/ml heparin, 5 mM GTP, or 3.6% DMSO. The 25 µl reaction mixtures were incubated at 37° C. for 1 hour and quenched by addition of 10% trichloroacetic acid. Samples were analyzed by 10% SDS-PAGE gels and the phosphorylated species were quantitated using a Fuji MACBAS1000™ phosphorimaging system (Fuji Medical Systems of Stamford, Conn.).

ATPase Assay. 100 µl reactions consisting of 1 µM GRP94 monomer, various concentrations of MgATP (pH 7.0), and 50 mM K-Hepes, pH 7.4, were incubated for two hours at 37° C. Samples were then spun through a CENTRICONO®-30 (Amicon of Beverly, Mass.) at 10,000 rpm, 42° C. to separate protein from nucleotide. A final concentration of 50 mM (NH$_4$)$_2$HPO$_4$, pH 7.0, and 4 µM AMP, pH 7.0, was added to dilutions of the above samples and centrifuged at 15,200 rpm for 5 minutes at 4° C. 100 µL of supernatant was then fractionated on a PARTISIL™ SAX column (Alltech of Deerfield, Ill.), using a Series 1050 Hewlett Packard HPLC system. Elution of nucleotides was performed by step gradient elution using a mobile phase of 150 mM (NH$_4$)$_2$HPO$_4$, pH 5.2, at 1.2 ml/min for the first ten minutes, followed by 300 mM (NH$_4$)$_2$HPO$_4$, pH 5.2, at a flow rate of 2 ml/min for the remainder of the elution. In this protocol, ADP and ATP were well resolved, with ADP eluting at 7 minutes and ATP at 12 minutes. Peak height values were used in calculations of percent hydrolysis and ADP formation. Spontaneous hydrolysis was determined for each ATP concentration in paired incubations lacking GRP94. The AMP was used as an internal reference standard to control for equivalent sample loading.

Tryptophan Fluorescence. Tryptophan fluorescence measurements were conducted in a FLUOROMAX™ spectrofluorometer (Spex Industries, Inc. of Edison, N.J.) with the slit widths set to 1 nm for both excitation and emission. Samples were excited at a wavelength of 295 nm and the emission spectra were recorded from 300-400 nm. All spectra were corrected by subtraction of buffer or buffer plus ligand samples. GRP94 (50 μg/ml) was incubated in buffer A supplemented with 10 mM Mg(OAc)$_2$ and the following concentrations of ligands for 1 hour at 37° C. (50 μM NECA, 50 μM geldanamycin, 2.5 mM ATP, or 2.5 mM ADP). Samples were then cooled to room temperature, transferred to a quartz cuvette, and the spectra collected. In control experiments, free tryptophan fluorescence was not significantly influenced by the presence of any of the assayed ligands.

Example 9

Hsp90 Proteins Differ in Adenosine-based Ligand Binding Properties

Figure 8:
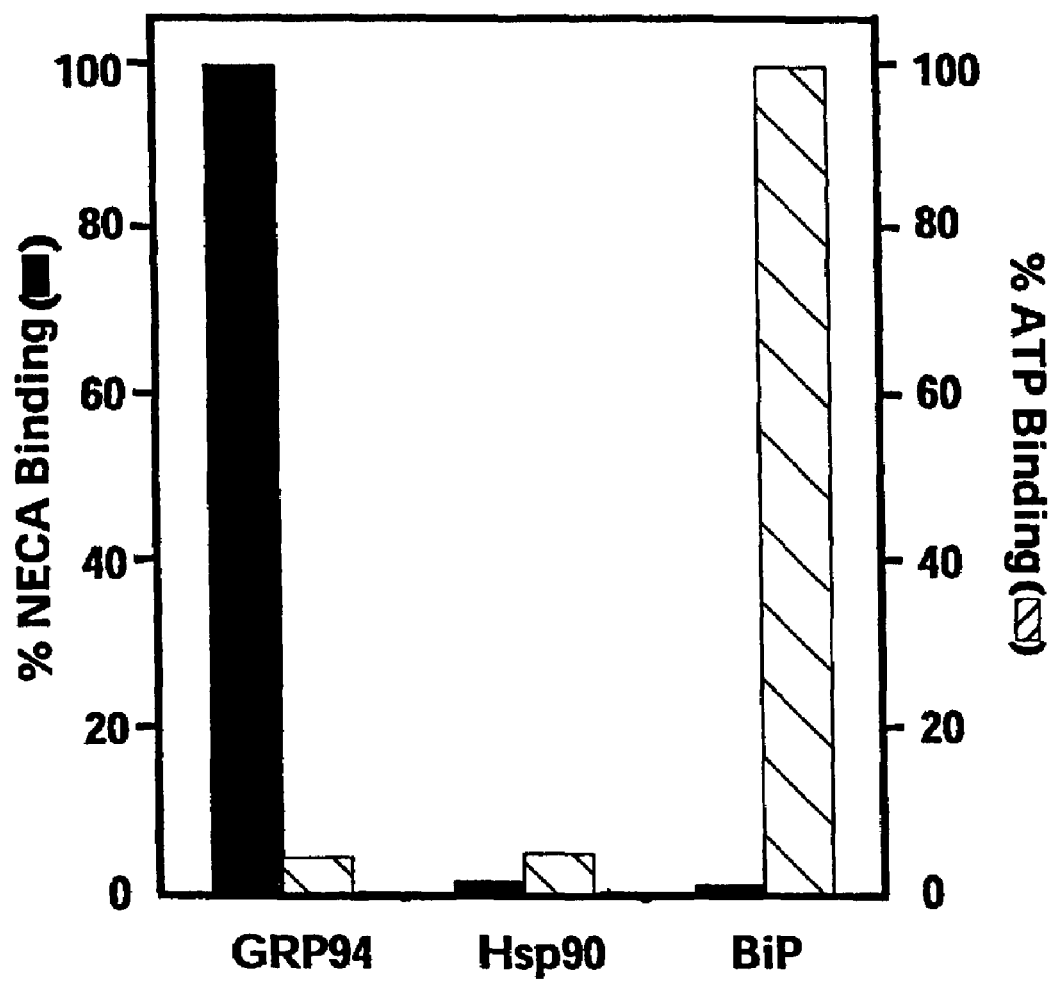
FIG. 8 is a bar graph depicting that GRP94 and Hsp90 exhibit differential ligand binding. NECA and ATP binding to GRP94 was performed in the presence of 20 nM [$^3$H]-NECA (closed bars) or 50 µM [$^{32}$P]ATP (hatched bars) for 1 hour at 4° C. Bound versus free nucleotide were separated by vacuum filtration. PEI treated glass filters (S&S #32, Schleicher and Schuell of Keene, N.H.) were used for the NECA binding assay while nitrocellulose filters (S&S BA85, Schleicher and Schuell of Keene, N.H.) were used to measure ATP binding. The data presented are averages of triplicate points and are corrected for nonspecific ligand binding.

To determine whether Hsp90 and GRP94 displayed distinct adenosine-ligand binding properties, the relative NECA and ATP binding activities of GRP94, Hsp90 and BiP, the endoplasmic reticulum Hsp70 paralog, were compared (FIG. 8). In these assays, purified GRP94, Hsp90 or BiP were incubated on ice for 60 min in the presence of 20 nM [$^3$H]-NECA and the bound versus free NECA resolved by vacuum filtration. As is evident in FIG. 8, whereas GRP94 displayed readily detectable [$^3$H]-NECA binding activity, [$^3$H]-NECA binding was not observed for Hsp90 or BiP. In similar experiments, [$^3$H]-NECA binding to Hsp90 was evaluated in the presence of molybdate and NP-40, which are known to stabilize the Hsp90 conformation associated with ATP binding, as described by Sullivan et al. (1997). Under these conditions, [$^3$H]-NECA binding to Hsp90 was again not observed.

When ATP binding was assayed, BiP displayed the expected ATP binding activity whereas no ATP binding was observed to Hsp90 or GRP94. As discussed below, the inability to detect ATP binding to Hsp90 is likely a consequence of the low affinity of Hsp90 for ATP (Prodromou et al. (1997) *Cell* 90:65-75; Scheibel et al. (1997) *J Biol Chem* 272:18608-18613). In summary, these data indicate that GRP94 and Hsp90 differ in their ability to bind the adenosine-based ligand NECA, and suggest that the ligand specificity of the adenosine nucleotide binding pocket of GRP94 differs from that of Hsp90.

Example 10

Kinetic Analysis of NECA Binding to GRP94

Figure 9A:
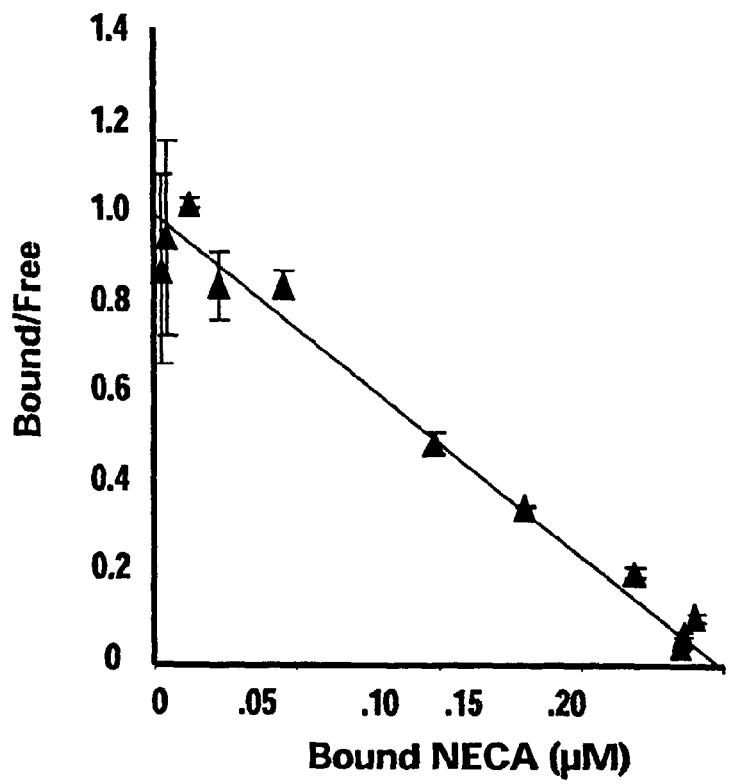
FIG. 9A is a Scatchard plot depicting characterization of NECA binding to GRP94. GRP94 was incubated with increasing concentrations of NECA for 1 hour at 4° C. as described in Materials and Methods. Bound versus free NECA were then separated by vacuum filtration with glass filters pretreated in 0.3% PEI.
Figure 9B:
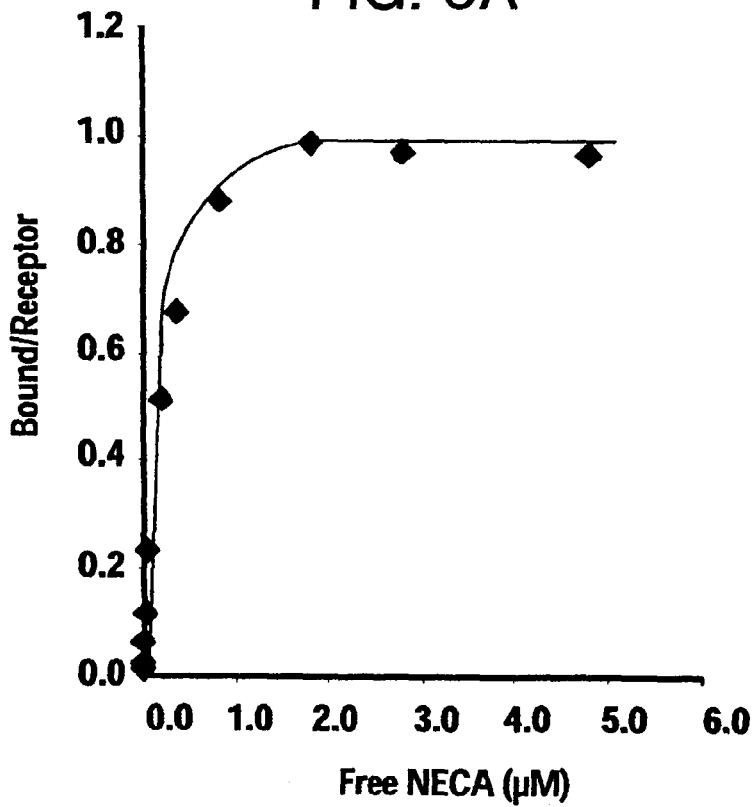
FIG. 9B is a saturation curve depicting characterization of NECA binding to GRP94. The curve is plotted with respect to GRP94 dimer concentration. The maximal binding stoichiometry is 1 molecule of NECA per molecule of GRP94 dimer.

A kinetic analysis of [$^3$H]-NECA binding to mammalian GRP94 is depicted in FIGS. 9A and 9B. [$^3$H]-NECA binding to GRP94 was saturable, with a Kd of 200 nM and displayed a binding stoichiometry of 0.5 mol [$^3$H]-NECA/mol GRP94 monomer. These values are similar to those observed with placental GRP94 (adenotin) by Hutchison et al. (1990) *Biochemistry* 29:5138-5144. A Hill plot of the binding data yielded a slope of 1.2, indicating that [$^3$H]-NECA binding to GRP94 was not cooperative.

Structurally, GRP94 exists as a dimer of identical subunits as described by Wearsch & Nicchitta (1996a) *Prot Express Purif* 7:114-121; Wearsch & Nicchitta (1996b) *Biochemistry* 35:16760-16769; Nemoto et al. (1996) *J Biochem* 120:249-256). Given that the two subunits are identical, a 50% ligand occupancy at binding saturation was unexpected. The dissociation rate of NECA from GRP94 is rapid (Huttemann et al. (1984) *Naunyn Schmiedebergs Arch Pharmacol.* 325:226-33) and so it was considered that the observed fractional occupancy level could reflect an artifact of the method used to separate bound vs. free [$^3$H]-NECA.

To evaluate the accuracy of the half-site occupancy value, the kinetics of NECA-GRP94 interaction were evaluated by isothermal titration calorimetry, a method that does not require the physical separation of bound and free ligand. In these experiments, illustrated in FIG. 9C, the binding stoichiometries of GRP94 for NECA and radicicol were determined. Radicicol is an antibiotic inhibitor of Hsp90 function that binds to the N-terminal nucleotide binding pocket of Hsp90 with high affinity (19 nM) and the expected binding stoichiometry of 2 mol radicicol/mol Hsp90 dimer, as proposed by Roe et al. (1999) *J Med Chem* 42:260-266. Analysis of NECA binding to GRP94 by isothermal titration calorimetry yielded a binding stoichiometry of 1.1 mol NECA/mol GRP94 dimer. (FIG. 9C).

Figure 9C:
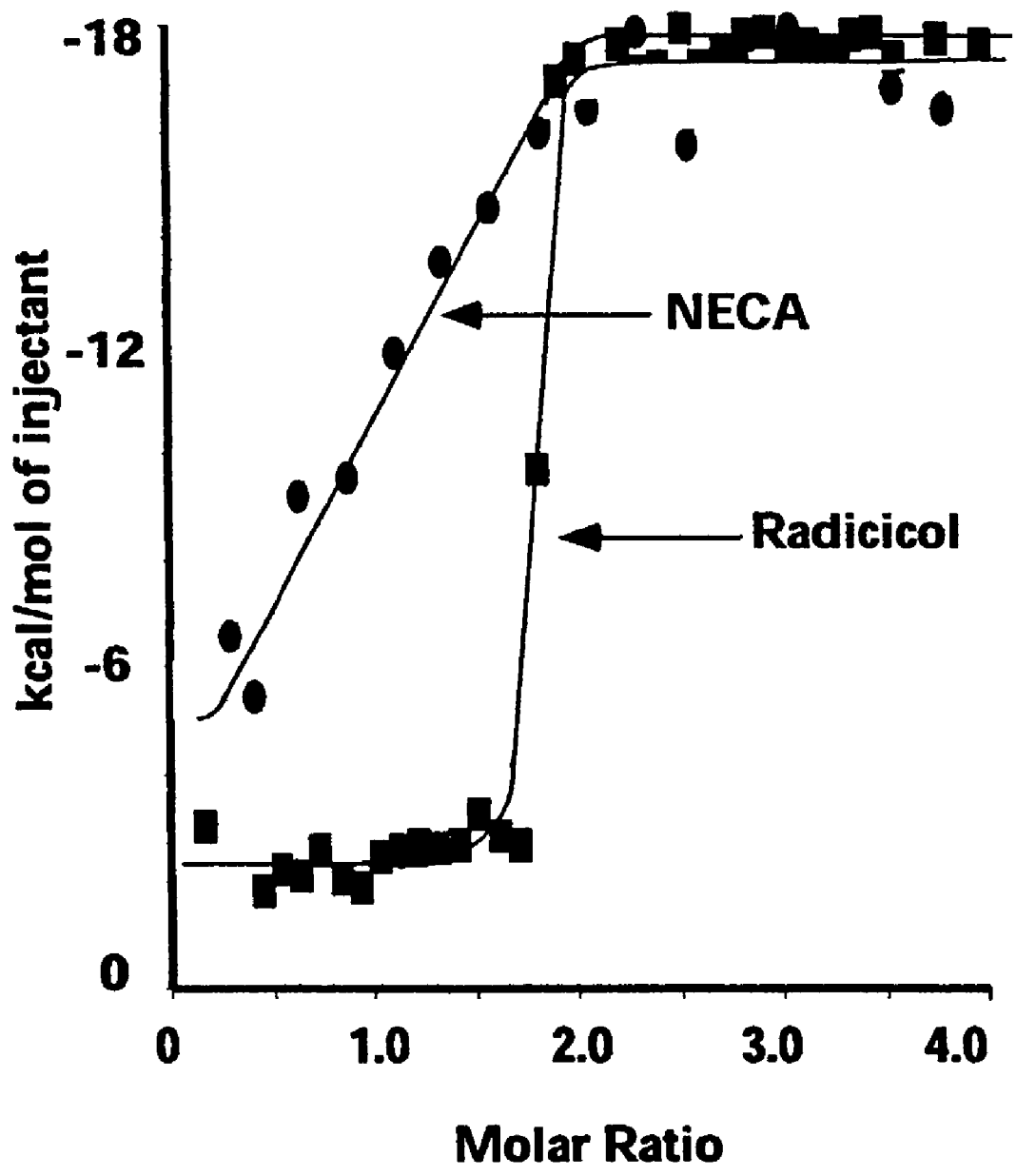
FIG. 9C is a graph depicting stoichiometry of GRP94 binding to NECA (solid oval) and radicicol (solid rectangle). NECA and radicicol binding to GRP94 was assayed by isothermal titration calorimetry. GRP94 was present at a concentration of 5 µM. NECA titrations were performed with a 152 µM NECA stock whereas radicicol titrations were performed with a 115 µM stock. ITC data were collected as µcal/sec versus time and the area under individual injection peaks, determined with the instrument software, was plotted.

Radicicol, in contrast, bound at a stoichiometry of 2 mol radicicol/mol GRP94 dimer, as shown in FIG. 9C. These data indicate that while radicicol can achieve full occupancy of the two nucleotide binding sites present in the native GRP94 dimer, other ligands, such as NECA, either bind to a single unique site on GRP94, or upon binding to one of the nucleotide binding sites, elicit a conformational change in the paired site that prevents further ligand binding.

Example 11

Specificity of Ligand Binding to the Nucleotide Binding Pocket of GRP94

To determine whether NECA bound to a single unique site on GRP94 or, alternatively, displayed half-site occupancy of the N-terminal adenosine nucleotide binding pockets, experiments were first performed to determine if NECA binds to the adenosine nucleotide binding pocket. [$^3$H]-NECA competition assays were performed with geldanamycin and radicicol, both of which are known to bind with high affinities to the nucleotide binding pocket of Hsp90 (Roe et al. (1999) *J Med Chem* 42:260-266, Lawson et al. (1998) *J Cell Physiol* 174: 170-8). The data depicted in FIG. 10A indicate that both geldanamycin and radicicol compete with [$^3$H]-NECA for binding to GRP94 and do so with high relative affinities and in the following rank order, radicicol >geldanamycin.

As described Wearsch & Nicchitta (1997) *J Biol Chem* 272:5152-5156, it is difficult to detect stable binding of ATP to GRP94. Should GRP94 display a similar and quite low affinity for ATP, as reported for Hsp90 (Kd=132 μM) by Prodromou et al. (1997) *Cell* 90:65-75, it would be very unlikely that ATP binding could be detected by standard techniques. Given the high affinity of GRP94 for NECA, however, potential interactions of NECA with the nucleotide binding domain could be addressed by competitive displacement assays. To determine the nucleotide binding specificity of GRP94, the ability of ATP, ADP or AMP to compete with NECA binding to GRP94 was examined. In these experiments, GRP94 was incubated with 20 nM [$^3$H]-NECA in the presence of increasing concentrations of ATP, ADP or AMP and the relative [$^3$H]-NECA binding determined by vacuum filtration. In the presence of nominal (80 μM) Mg$^{2+}$, it was observed that ATP, ADP and AMP effectively competed with [$^3$H]-NECA for binding to GRP94.

Figure 10A:
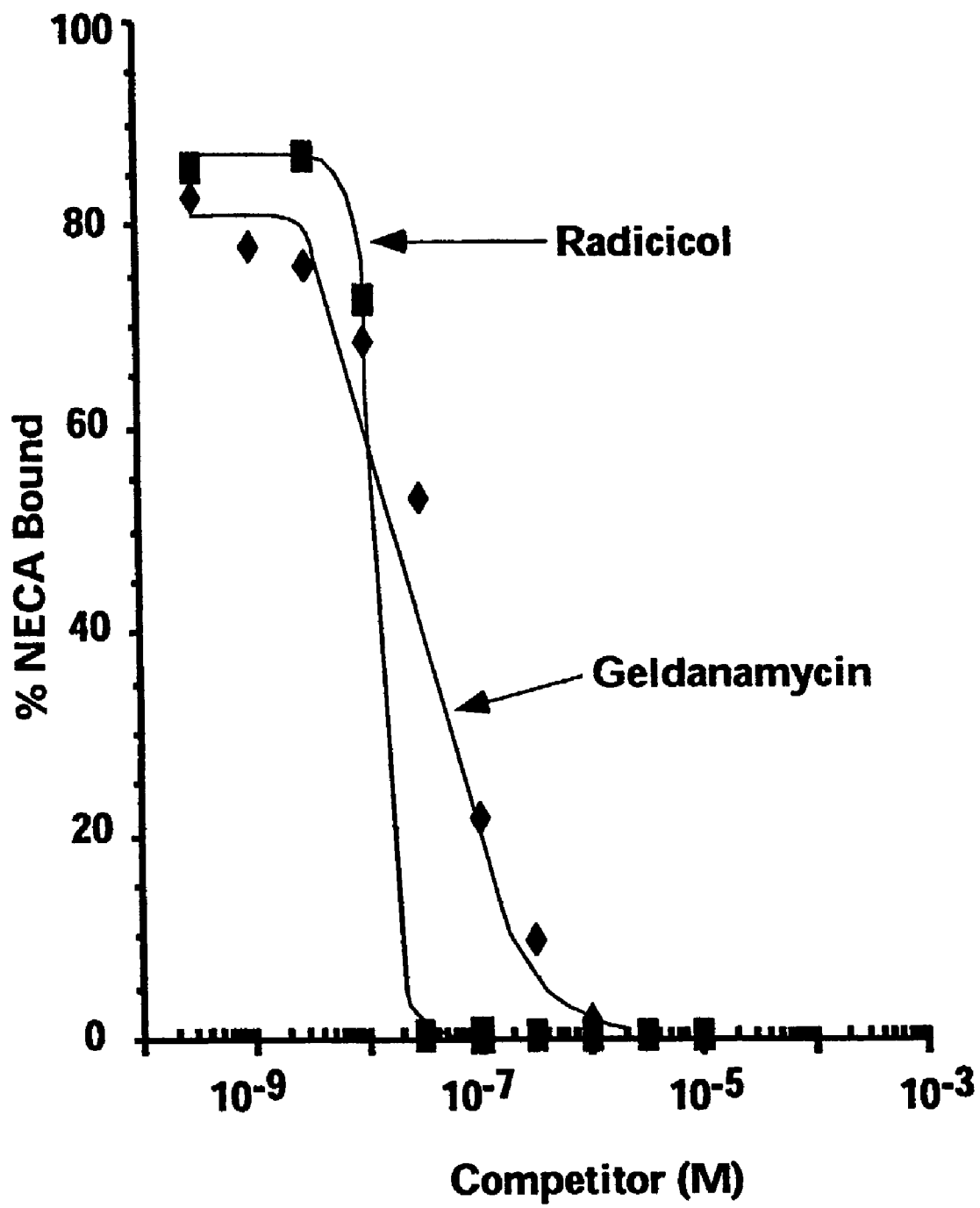
FIG. 10A is a graph depicting a competition assay for NECA by the Hsp90 family inhibitors, geldanamycin (♦) and radicicol (■). GRP94 was incubated with 20 nM [$^3$H]-NECA and increasing concentrations of competitors for 1 hour at 4° C. Bound NECA was separated from free by vacuum filtration with glass filters pre-treated in 0.3% PEI. All data points represent the average of triplicates points minus background (nonspecific NECA binding in the absence of protein).
Figure 10B:
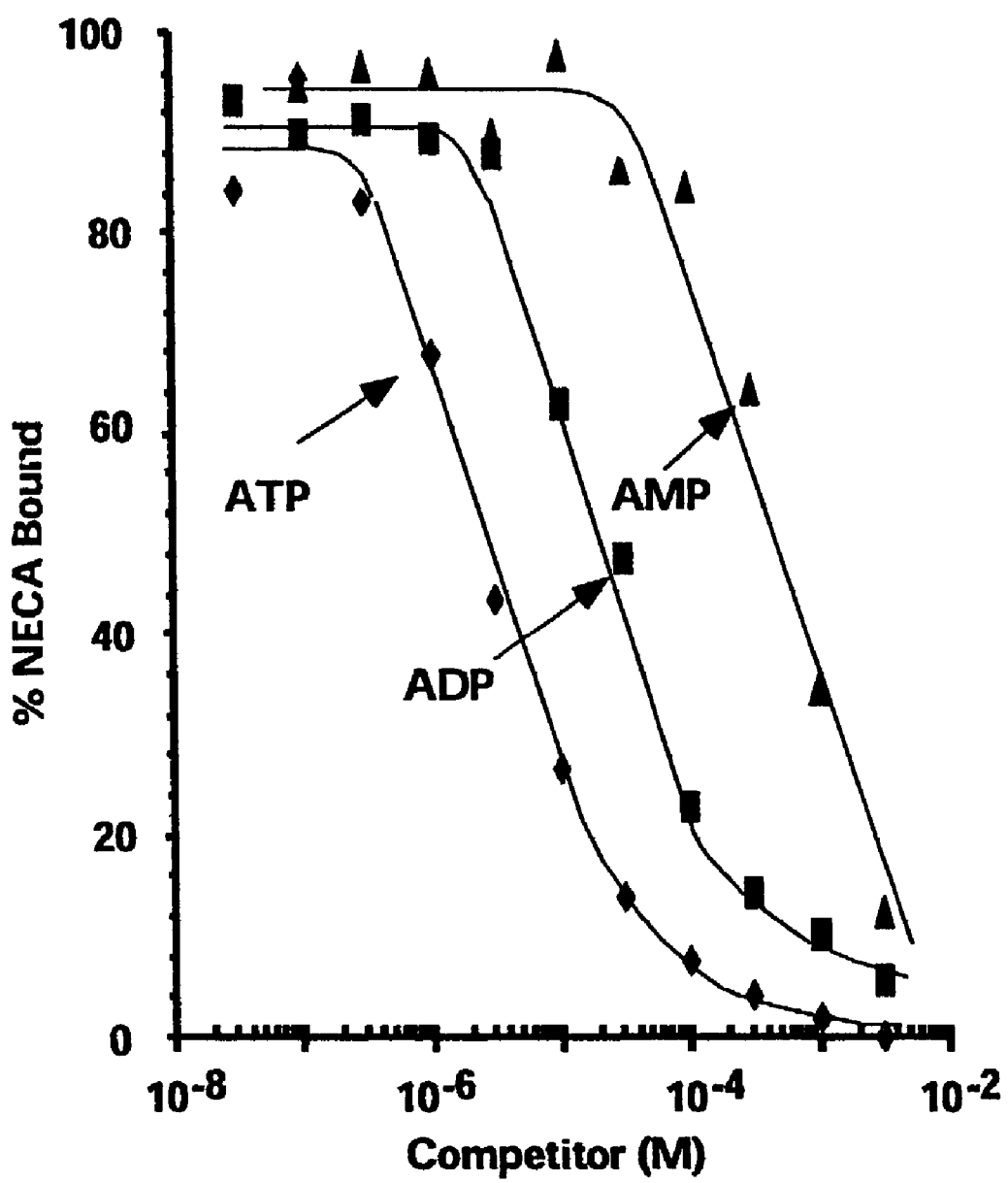
FIG. 10B is a graph depicting a competition assay for NECA by ATP (♦), ADP (■), and AMP (▲). GRP94 was incubated with 20 nM 3H-NECA and increasing concentrations of competitors for 1 hour at 4° C. Bound NECA was separated from free by vacuum filtration with glass filters pre-treated in 0.3% PEI. All data points represent the average of triplicate points minus background (nonspecific NECA binding in the absence of protein).
Figure 10C:
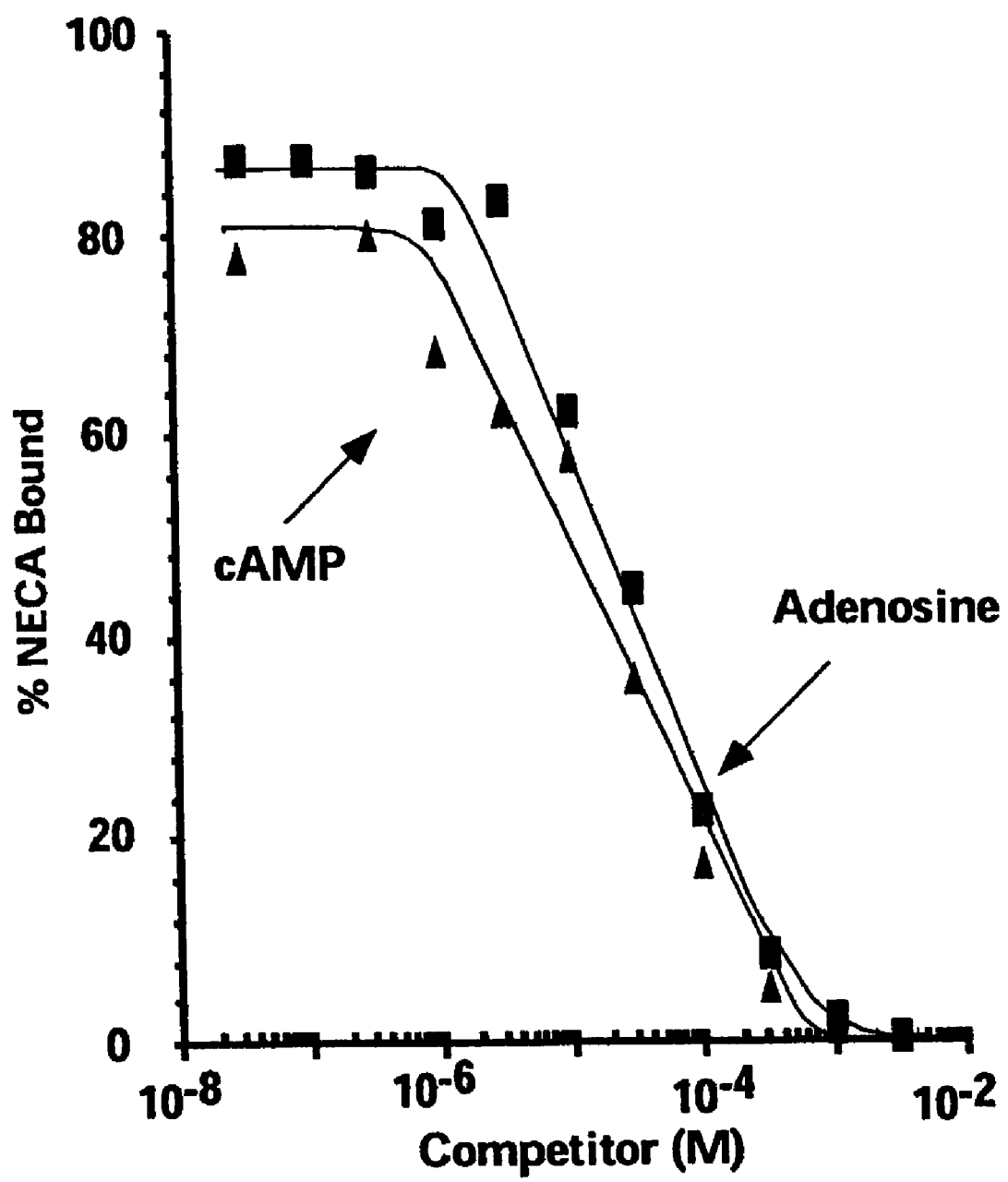
FIG. 10C is a graph depicting a competition assay for NECA by adenosine (▲), and cAMP (■). GRP94 was incubated with 20 nM [$^3$H]-NECA and increasing concentrations of competitors for 1 hour at 4° C. Bound NECA was separated from free by vacuum filtration with glass filters pre-treated in 0.3% PEI. All data points represent the average of triplicates points minus background (nonspecific NECA binding in the absence of protein).

Three points are evident from these experiments. One, because NECA binding to GRP94 can be effectively inhibited by geldanamycin, radicicol, and adenosine nucleotides, it can be concluded that NECA binds to the analogous N-terminal adenosine nucleotide binding domain of GRP94 (FIG. 10A). Two, the relative affinities of GRP94 for ATP, ADP and AMP are quite low (FIG. 10B). Thus, a 50% inhibition of [$^3$H]-NECA binding required approximately a 1000-fold molar excess of ATP. Three, the relatively high binding affinity of GRP94 for NECA, when viewed with respect to the established molecular interactions of the adenine and ribose moieties of adenosine in the adenosine nucleotide binding pocket of Hsp90, suggest that a principal selection for ligands is made on the basis of the adenosine moiety. For this reason, the interaction of other adenosine-bearing ligands with the N-terminal nucleotide binding pocket was examined (FIG. 10C). These data indicated that cAMP and free adenosine also bound to the N-terminal adenosine nucleotide binding pocket of GRP94, with the relative displacement activity approximating that observed for ADP.

Figure 11:
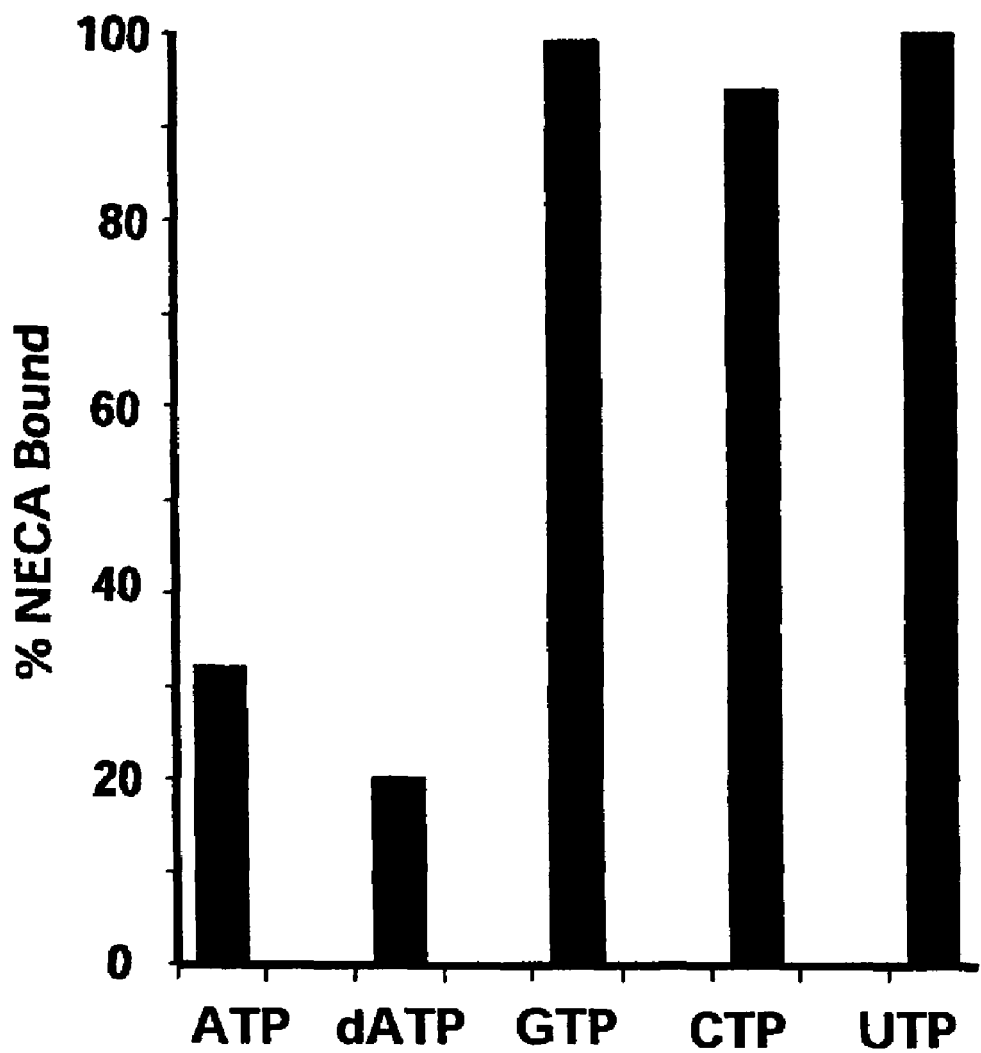
FIG. 11 is a bar graph depicting that ligand binding specificity of GRP94 to the adenosine base. GRP94 was incubated with 20 nM [$^3$H]-NECA and competitors, all at 50 µM final concentration for 1 hour at 4° C., and bound vs. free NECA was separated by vacuum filtration with glass filters pre-treated in 0.3% PEI.

Because the data indicated that GRP94 bound adenosine, adenosine derivatives, and adenosine nucleotides with an unusually broad specificity, additional studies were performed to confirm the nucleoside specificity of these binding phenomena. In the experiment depicted in FIG. 11, the [$^3$H]-NECA competitive displacement assay was used to address the nucleoside base specificity directly. Though GRP94 could bind both ATP and deoxyATP, little to no binding of GTP, CTP or UTP was observed. The nucleotide binding pocket of GRP94 thus appears to be strict in its selection of adenosine-bearing ligands.

In comparing the relative affinities of GRP94 for ATP and ADP, as displayed in NECA competition assays, clear differences between the ATP/ADP binding properties of GRP94 and those previously reported for Hsp90 were noted. Regarding GRP94, ATP was found to compete NECA binding with an eight-fold higher efficacy than ADP. In contrast, the N-terminal domain of Hsp90 binds ADP with a four-fold higher affinity than that observed for ATP (Prodromou et al. (1997) *Cell* 90:65-75). It was hypothesized that this difference was due to a lack of $Mg^{2+}$ ions in the assay buffer, as $Mg^{2+}$ has been demonstrated to be essential for ATP/ADP binding to recombinant forms of the Hsp90 N-terminal nucleotide binding domain by Prodromou et al. (1997) *Cell* 90:65-75 and Obermann et al. (1998) *J Cell Biol* 143:901-910.

Figure 12:
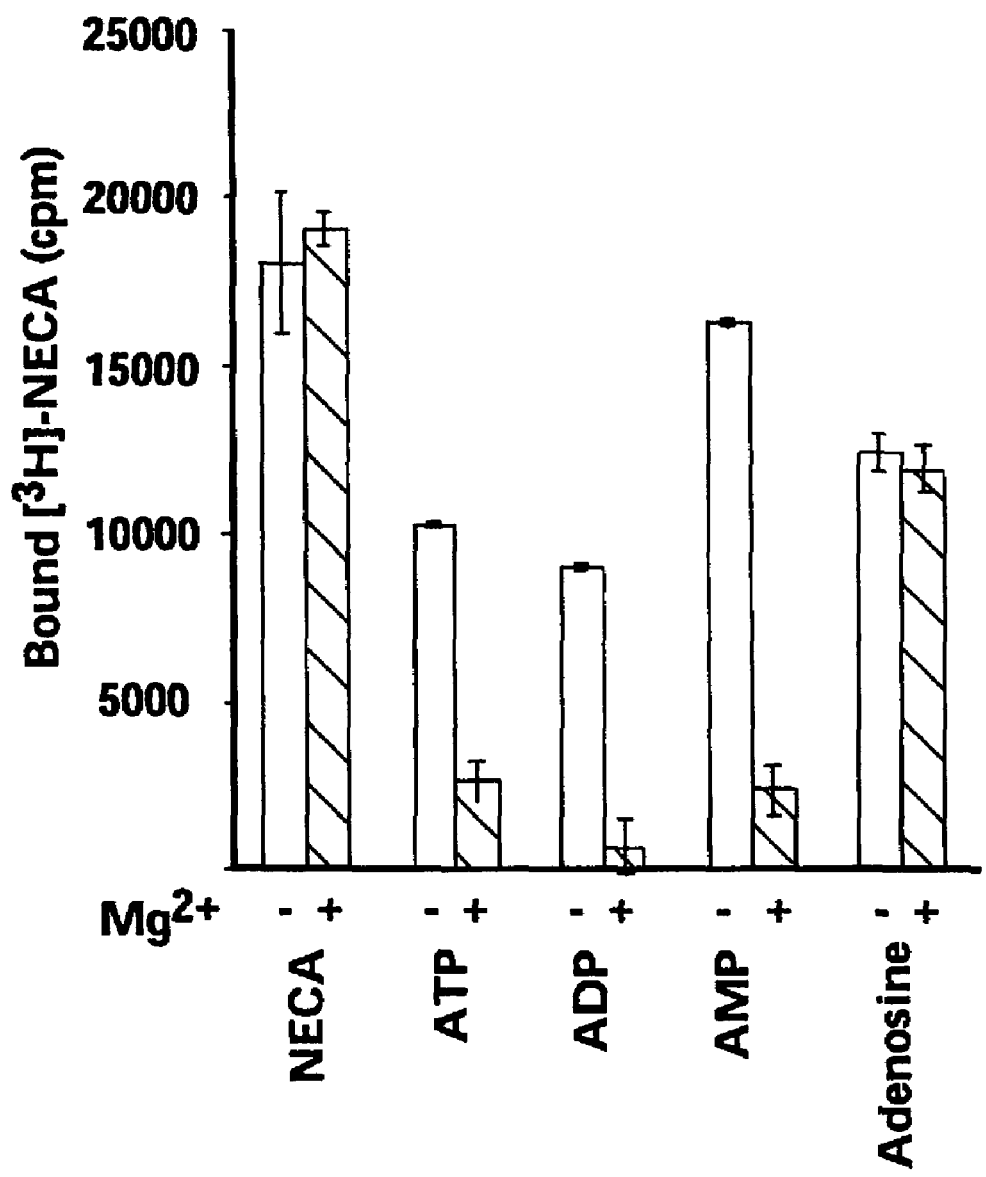
FIG. 12 is a graph depicting that binding of ATP, ADP, and AMP to GRP94 is sensitive to $Mg^{2+}$ concentration. GRP94 was incubated for 1 hour at 4° C. in 50 mM Tris, 20 nM [$^3$H]-NECA and one of the following concentrations of competitor: $3.1 \times 10^{-6}$ M ATP, $3.1 \times 10^{-5}$ M ADP, $6 \times 10^{-4}$ M AMP, or $3.1 \times 10^{-5}$ M adenosine. Reactions were performed in the presence of 10 mM Mg(OAc)$_2$ (hatched bars) or in the presence of nominal, endogenous magnesium (closed bars). Bound vs. free NECA was separated by vacuum filtration with glass filters pretreated in 0.3% PEI.

This hypothesis was examined in experiments where the relative affinity of GRP94 for NECA, adenosine, ATP, ADP and AMP were compared in the presence and absence of excess $Mg^{2+}$ (FIG. 12). In these experiments, it was observed that although excess $Mg^{2+}$ was without effect on the binding of NECA or adenosine to GRP94, $Mg^{2+}$ markedly stimulated the binding of ATP, ADP and AMP. These data are consistent with recent crystal structure data identifying $Mg^{2+}$ interactions with the α and β phosphates as being requisite for ATP/ADP binding to the N-terminal domain of Hsp90. See Prodromou et al. (1997) *Cell* 90:65-75. However, unlike the N-terminal domain of Hsp90, MgATP and MgADP bind to GRP94 with nearly identical relative affinities. It should also be noted that the presence of excess $Mg^{2+}$ was without effect on the relative binding affinities of cAMP and geldanamycin for GRP94.

Example 12

Nucleotide Requirement for Autophosphorylation and ATP Hydrolysis

Figure 13A:
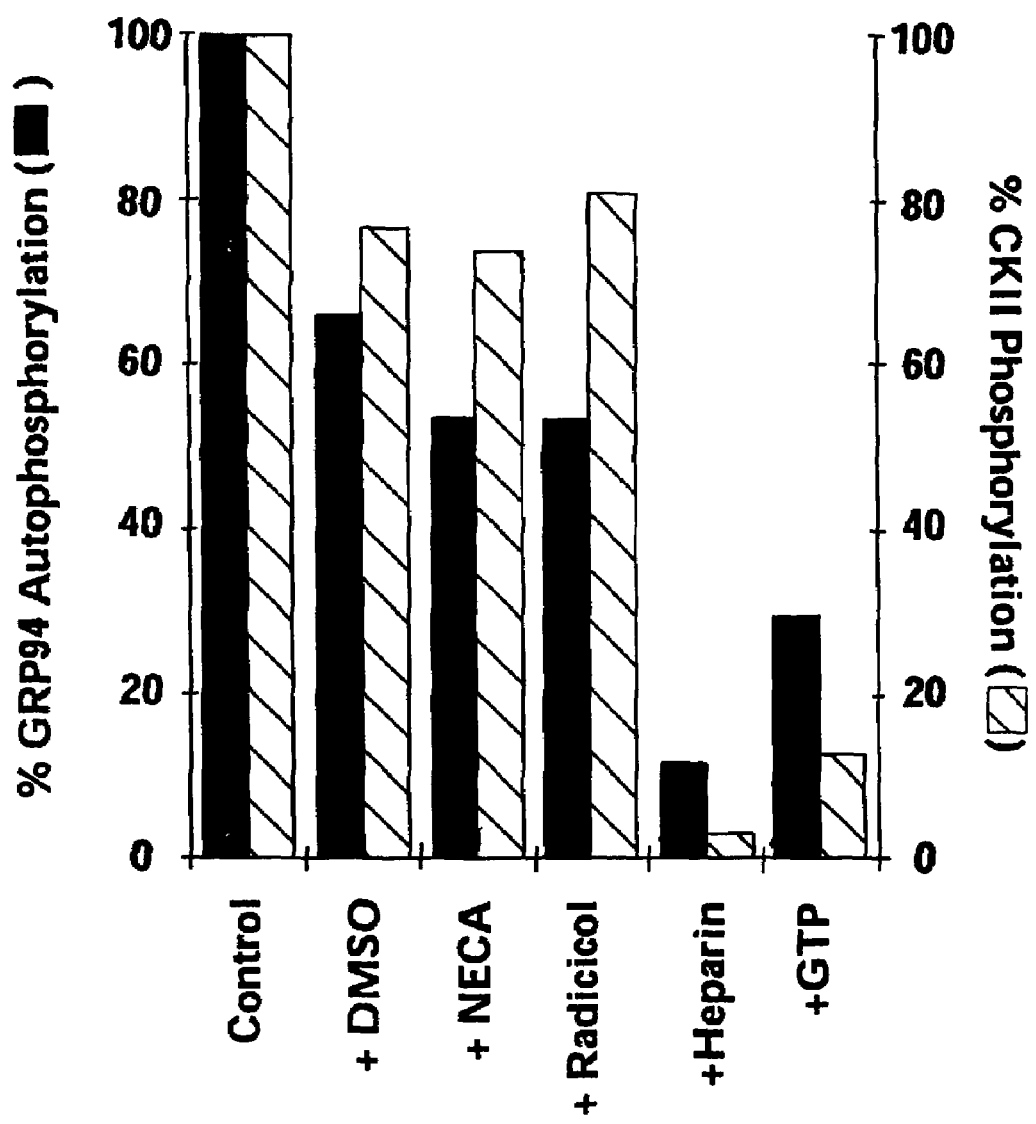
FIG. 13A is a bar graph depicting the effects of NECA on GRP94 autophosphorylation. 25 µl reactions consisting of 1 µM GRP94 (closed bars), 0.15 mM γ-$^{32}$PATP (6000 cpm/pmol), 10 mM Mg(OAc)$_2$, and 50 mM K-Hepes, pH 7.4 ) were incubated for 1 hour at 37° C. One (1) unit casein kinase II (hatched bars) was incubated in the above conditions with the addition of 4 µM casein. Competitors were added to the appropriate samples with a final concentration of 180 µM NECA in 3.6% DMSO, 180 µM radicicol in 3.6% DMSO, 5 µg/ml heparin, 5 mM GTP, or 3.6% DMSO. Phosphorylated species were quantitated on a Fuji MACBAS1000™ phosphorimaging system, and the average PSL units of three independent experiments are displayed.

To test whether binding to the nucleotide binding pocket is directly responsible for the observed GRP94 autophosphorylation activity, NECA and radicicol were utilized as inhibitors of ATP binding to GRP94. Data regarding autophosphorylation activities are shown in FIG. 13A. In this experiment, the autophosphorylation activity of GRP94 was assayed in the presence of NECA, radicicol, heparin and GTP. Heparin and GTP were included on the basis of previous studies indicating a casein kinase II-like contaminant in purified preparations of GRP94 (Wearsch & Nicchitta (1997) *J Biol Chem* 272:5152-5156; Riera et al. (1999) *Mol Cell Biochem* 191:97-104; and Ramakrishnan et al. (1997) *J Cell Physiol* 170:115-29). By similar logic, the relative effects of these compounds on GRP94 kinase activity were compared in parallel with purified casein kinase II, with casein kinase II activity measured with purified casein.

As is evident from the data presented in FIG. 13A, neither NECA nor radicicol, both of which bind to the N-terminal nucleotide binding domain of GRP94, significantly inhibit GRP94 derived or casein kinase II activity below the solvent background. Because of the relatively high hydrophobicity of NECA and radicicol, incubations containing these compounds contained significant concentrations of the ligand solvent, dimethylsulfoxide, which itself significantly reduced both the GRP94-derived and casein kinase II activities. Heparin and GTP markedly attenuated GRP94-derived and casein kinase II activity. In summary, blocking nucleotide access to the N-terminal adenosine nucleotide GRP94 binding pocket does not significantly inhibit GRP94 autophosphorylation activity.

Figure 13B:
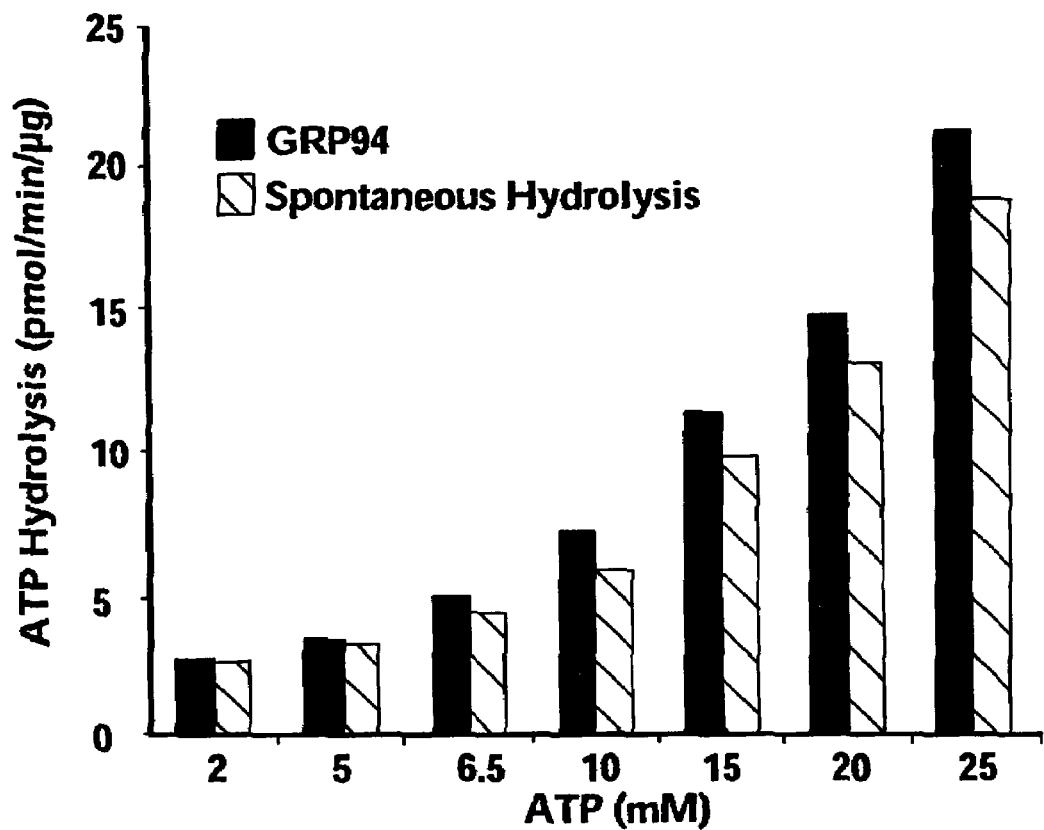
FIG. 13B is a bar graph depicting ATP hydrolysis in the presence and absence of GRP94. 100 µl reactions consisting of 1 µM GRP94 monomer, various concentrations of MgATP (pH 7.0), and 50 mM K-Hepes, pH 7.4, were incubated for two hours at 37° C. ATP and ADP were separated on a Hewlett Packard HPLC using a Partisil SAX column. Spontaneous ATP hydrolysis was determined in the absence of protein. Hydrolysis in the presence of GRP94 is indicated by closed bars and spontaneous hydrolysis is indicated by the hatched bars.

The findings that cycles of ATP binding and hydrolysis function in the regulation of Hsp90 activity, and that GRP94 exhibits an ATPase activity suggest that GRP94 and Hsp90 are indeed regulated by a similar mechanism. To further evaluate this suggestion, the ATPase activity of GRP94 was assayed as a function of ATP concentration (FIG. 13B). Two points are immediately evident from the observed data. First, the ATPase activity does not display saturation; no evidence for a Vmax could be obtained and so traditional criteria for enzymatic function (i.e., Km/Kcat/Vmax) could not be applied. Secondly, the absolute magnitude of the ATPase activity exceeded the spontaneous rate of ATP hydrolysis by only a small factor. The observed ATPase activity was sensitive to inhibition by NECA, and thus is likely generated upon binding of ATP to the N-terminal nucleotide binding domain.

Example 13

Conformational Consequences of Adenosine Nucleotide Binding to GRP94

Figure 14:
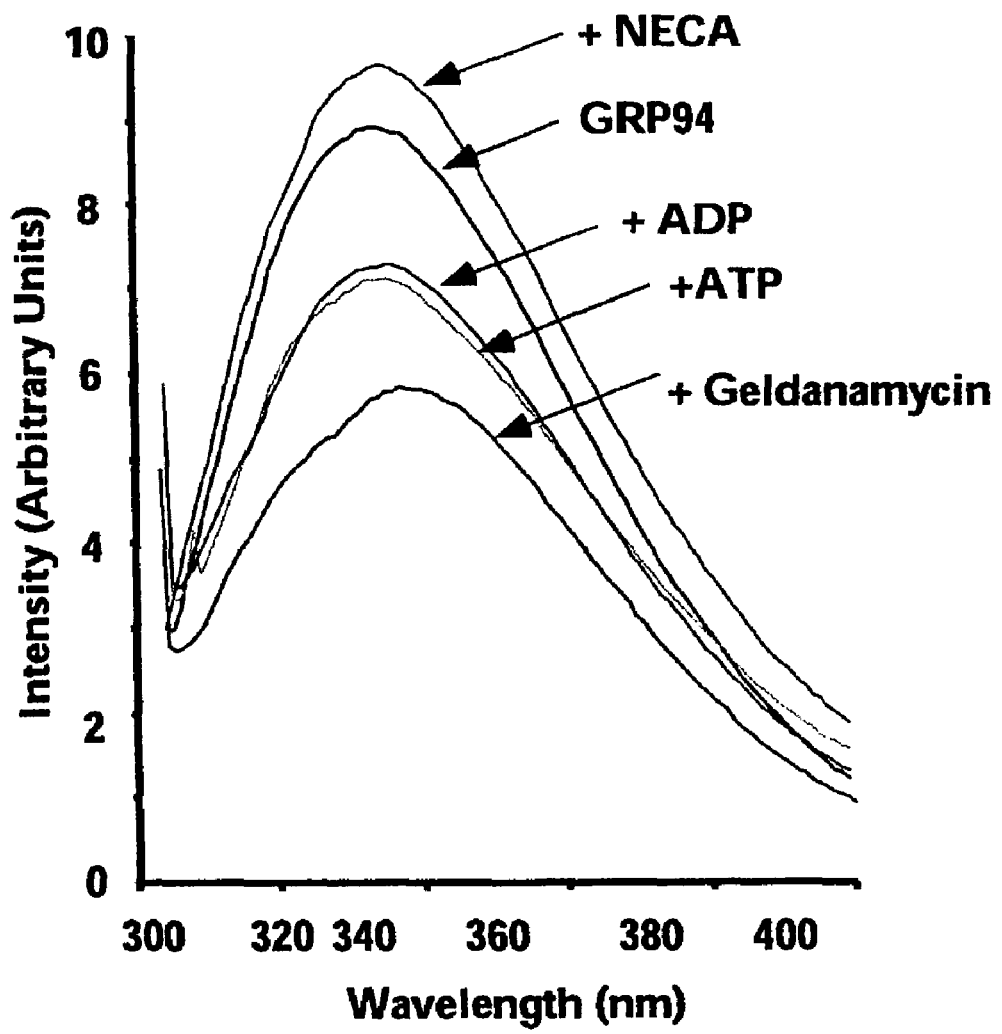
FIG. 14 is a graph depicting ligand-induced conformational changes of GRP94. GRP94 (50 µg/ml) was incubated in buffer A supplemented with 10 mM Mg(OAc)$_2$ and the following concentrations of ligands for 1 hour at 37° C.: 50 µM NECA, 50 µM geldanamycin, 2.5 mM ATP, or 2.5 mM ADP. Samples were excited at a wavelength of 295 nm and the tryptophan emission spectra were recorded from 300-400 nm. All spectra were corrected by subtraction of spectra obtained in buffer alone or buffer+ligand samples.

Having been unable to identify a functional correlate of ATP binding to GRP94, the effects of ATP, ADP, NECA and geldanamycin on GRP94 conformation were assessed. In these studies, the tryptophan emission spectra of GRP94, complexed with the indicated ligands, was examined as a measure of tertiary conformational state in accordance with techniques described by Guilbault (1967) *Fluoresence: Theory, Instrumentation, and Practice*, Marcel Dekker, Inc., New York, N.Y. As shown in FIG. 14, high concentrations of ATP or ADP elicited near identical changes in the GRP94 tryptophan fluorescence spectra. Significantly, in the presence of ATP or ADP, the tryptophan fluorescence was decreased, as was observed in the presence of geldanamycin. These data indicate that ATP and ADP elicit a conformational change similar to that occurring in the presence of the inhibitory ligand geldanamycin and that the conformation of GRP94 in the ATP and ADP-bound state, as assessed by tryptophan fluorescence, are essentially identical. In contrast, the addition of NECA increased the tryptophan fluorescence, indicating that ligands can elicit different conformational states in GRP94. As demonstrated in Examples 1-8 above, such changes in GRP94 conformation can have dramatic effects on GRP94 chaperone function.

Summary of Examples 9-13

Examples 9-13 disclose that Hsp90 paralogs GRP94 and HSP90 display distinct structural and functional interactions with adenosine nucleotides. Unlike HSP90, GRP94 displays specific, high affinity binding interactions with substituted adenosine derivatives such as N-ethylcarboxamidoadenosine (NECA). In analyzing such interactions, the occupancy states of the N-terminal ATP/ADP binding domains of GRP94 are communicated between the two identical subunits. This conclusion is drawn from the observation that at saturation NECA is bound to GRP94 at a stoichiometry of 1 mol NECA: mol GRP94 dimer. In contrast to NECA, the GRP94 inhibitory ligand, radicicol, binds at a stoichiometry of 2 mol:mol GRP94. Thus, although the relevant structural components of the adenosine nucleotide binding pocket are conserved between GRP94 and Hsp90, the ligand specificities of the two binding sites differ. Thus, while it is not applicants' desire to be bound by a particularly mechanistic theory, it is envisioned that the specificity of ligand binding to the N-terminal adenosine nucleotide binding pocket is influenced by the domains C and N-terminal to the binding pocket, where significant sequence divergence between HSP90 and GRP94 can be identified.

The data obtained from both traditional ligand binding studies (FIG. 9) and isothermal titration calorimetry demonstrate that GRP94 binds NECA at a stoichiometry of 1 mol NECA: mol GRP94 dimer. In addition, competition studies indicate that NECA binding to GRP94 can be wholly competed by geldanamycin, radicicol, ATP, and ADP (FIGS. 10A-10C), indicating that NECA is binding to the conserved, N-terminal adenosine nucleotide binding domain. Because GRP94 contains two such sites per molecule (Wearsch & Nicchitta (1996b) *Biochemistry* 35:16760-16769), it then follows that GRP94 subunits communicate with one another to confer single site occupancy.

The identification of ATP and ADP as the native ligands for the Hsp90 proteins is based on crystallographic studies identifying an N-terminal, highly conserved nucleotide binding pocket (Prodromou et al. (1997) *Cell* 90:65-75), complementary in vivo studies demonstrating that the amino acids that participate in ATP/ADP binding are essential for Hsp90 function in vivo and lastly (Obermann et al. (1998) *J Cell Biol* 143:901-910; Panaretou et al. (1998) *EMBO J* 17:4829-4836), that the Hsp90 proteins display ATPase activity (Grenert et al. (1999) *J Biol Chem* 274:17525-17533; Nadeau et al. (1993) *J Biol Chem* 268:1479-1487; Obermann et al. (1998) *J Cell Biol* 143:901-910). That HSP90 and GRP94 differ in NECA binding activity, despite the high homologies in the N-terminal nucleotide binding pockets of the two protein, suggests that differences might also exist in the ability of the two proteins to catalyze ATP hydrolysis. In fact, when the GRP94 ATPase activity was investigated at ATP concentrations appropriate for such a low affinity interaction it was observed that the GRP94 ATPase activity barely exceeded the rate of spontaneous hydrolysis and, more importantly, did not saturate at increasing ATP concentrations.

Further studies of the binding properties of the conserved domain indicated that it displays poor selectivity between adenosine nucleotides, and will bind ATP, dATP, ADP, AMP, cAMP and free adenosine. On the basis of these and other data, GRP94 conformation is regulated in an allosteric manner by an adenosine-bearing ligand other than ATP/ADP, based on ligand-mediated conformational regulation.

GRP94-dependent ATP hydrolysis, as displayed by the purified protein in the absence of any, as yet unidentified co-factors, is non-enzymatic, and therefore unlikely to contribute to the regulation of GRP94 function. Further confounding the assignment of ATP and ADP as the physiological ligands for GRP94 are the following observations. First, neither ATP nor ADP has been demonstrated to regulate GRP94 activity, as described by Wearsch & Nicchitta (1997) *J Biol Chem* 272:5152-5156. Secondly, that by virtue of its insensitivity to NECA and radicicol, the GRP94 autophosphorylation activity does not reflect adenosine nucleotide binding to the N-terminal nucleotide binding domain (FIG. 13). Thirdly, and perhaps most importantly, ATP, ADP, and the inhibitor geldanamycin elicit similar conformational changes in GRP94. Interestingly, in the presence of NECA, a different conformational change from that occurring in the presence of ATP, ADP, or geldanamycin was observed (FIG. 14). These data are consistent with ATP and ADP binding to GRP94 and stabilizing the protein in an inactive conformation, as is observed in the presence of geldanamycin.

In evaluating these data, the inability to identify an enzymatic basis for the ATPase activity and the conformation data suggesting that ATP/ADP would serve as inhibitory agent, either unidentified accessory proteins interact with GRP94 to substantively alter the kinetic and thermodynamic basis for its interaction with ATP/ADP or an adenosine-based ligand, other than ATP/ADP, serves as the physiological ligand. The ligand is produced during times of cell stress, such as anoxia, nutrient deprivation or heat shock, to activate GRP94 function. The ligand elicits a conformational change in GRP94 that substantively alters its interaction with substrate (poly) peptides.

REFERENCES

The references listed below as well as all references cited in the specification are incorporated herein by reference to the extent that they supplement, explain, provide a background for or teach methodology, techniques and/or compositions employed herein.

Anderson & Matovcik (1977) *Science* 197:1371-1374.
Arnold et al. (1995) *J Exp Med* 182:885-889.
Bacalloa et al. (1994) *J Cell Sci* 107:3301-3313.
Basu & Srivastava (1999) *J Exp Med* 189:797-802.
Blachere et al. (1993) *J Immunotherapy* 14:352-356.
Blachere et al. (1997) *J Exp Med* 186:1315-1322.
Bodanszky et al. (1976) *Perptide Synthesis,* 2nd Ed. John Wiley & Sons.
Brawer et al. (1992) *J Urol* 147:841-845.
Buchner et al. (1998) *Methods Enzymol* 290:323-338.
Buchner (1999) *Trends Biochem Sci* 24:136-141.
Bumal (1988) *Hybridoma* 7(4):407-415.
Caplan (1999) *Trends Cell Biol* 9:262-268.
Catalona et al. (1993) *JAMA* 270:948-958.
Chadli et al. (1999) *J Biol Chem* 274:4133-4139.
Chang et al. (1997) *Mol Cell Biol* 17:318-25.
Chavany et al. (1996) *J Biol Chem* 271:4974-4977.
Chen et al. (1996) *Mol Endocrinol* 10:682-693.
Chen et al. (1996) *J Cereb Blood Flow Metab* 16:566-577.
Chien et al. (1991) *Proc Natl Acad Sci USA* 88:9578-9582.
Choi et al. (1987) *J Neurosci* 7:357.
Csermely & Kahn (1991) *J Biol Chem* 266:4943-4950.
Csermely et al. (1995) *J Biol Chem* 270:6381-6388.
Csermely et al. (1993) *J Biol Chem* 268:1901-1907.
Csermely et al. (1998) *Pharmacol Ther* 79:129-168.
Davis & Maher (1994) *Brain Res* 652(1):169-173.
Demotz et al. (1989) *Nature* 343:682-684.

Dittmar et al. (1998) *J Biol Chem* 273:7358-7366.
Doherty et al. (1995) *Neuron* 14:57-66.
Duina et al. (1996) *Science* 274:1713-1715.
Elliott et al. (1990) *Nature* 348:191-197.
Falk et al. (1991) *Nature* 351:290-296.
Falk et al. (1990) *Nature* 348:248-251.
Fan et al. (1999) *J Mol Med* 77:577-596.
Ferreira et al. (1994) *J Cell Biochem* 56:518-26.
Fields et al. (1990) *Int J Peptide Protein Res* 35:161-214.
Flynn et al. (1989) *Science* 245:385-390.
Freireich et al. (1966) *Cancer Chemotherap Rep* 50:219-244.
Gerweck et al. (1979) *Cancer Res* 39:966-972.
Ginsberg & Busto (1989) *Stroke* 20:1627.
Glasebrook et al. (1980) *J Exp Med* 151:876.
Gradin et al. (1996) *Mol Cell Biol* 16:5221-5231.
Grenert et al. (1999) *J Biol Chem* 274:17525-17533.
Grollman et al. (1993) *J Biol Chem* 268:3604-3609.
Hansen et al. (1989) *Electrophoresis* 10:645-652.
Hebert et al. (1996) *EMBO J* 15:2961-2968.
Hebert et al. (1997) *J Cell Biol* 139:613-623.
Heike et al. (1996) *J Leukoc Biol* 60:153-8.
Heike et al. (1994) *J Immunotherapy* 15:165-174.
Henttu & Vihko (1989) *Biochem Biophys Res Comm* 160 (2):903-910.
Horch et al. (1999) *Neuron* 23:353-364.
Hutchison et al. (1990) *Biochemistry* 29:5138-5144.
Hutchison & Fox (1989) *J Biol Chem* 264:19898-19903.
Huttemann et al. (1984) *Naunyn Schmiedebergs Arch Pharmacol* 325:226-233.
Inaba (1992) *J Exp Med* 176:1693-1702.
Ishii et al. (1999) *J Immunol* 162:1303-1309.
Israeli et al. (1993) *Cancer Res* 53:227-230.
Jakob et al. (1995) *J Biol Chem* 270:7288-7294.
Jakob et al. (1996) *J Biol Chem* 271:10035-10041.
Johnson et al. (1996) *J Steroid Biochem Mol Biol* 56:31-37.
Karpiak et al. (1989) *Ann Rev Pharmacol Toxicol* 29:403.
Kassenbrock & Kelly (1989) *EMBO J* 8:1461-1467.
Kosano et al. (1998) *J Biol Chem* 273:32973-32979.
Kuznetsov et al. (1994) *J Biol Chem* 269:22990-22995.
Kuznetsov (1996) *Proc Natl Acad Sci USA* 93:8584-8589.
Lawson et al. (1998) *J Cell Physiol* 174:170-178.
Li & Srivastava (1993) *EMBO J* 12:3143-3151.
Li et al. (1993) *EMBO J* 12:3143-3151.
Mandel et al. (1994) *J Cell Sci* 107:3315-224.
Masliah et al. (1992) *Exp Neurol* 136:107-122.
Massa et al. (1996) "The Stress Gene Response in Brain" in *Cerebrovascular and Brain Metabolism Reviews*, pp. 95-158, Lippincott-Raven Publishers, Philadelphia, Pa.
McAllister et al. (1997) *Neuron* 18:767-778.
McAuley (1995) *Cerebrovasc Brain Metab Review* 7:153-180.
McOmie (1973) *Protective Groups in Organic Chemistry*, Plenum Press, New York, N.Y.
Meienhofer (1983) *Hormonal Proteins and Peptides* Vol. 2, pp. 46, Academic Press, New York, N.Y.
Melnick et al. (1992) *J Biol Chem* 267:21303-21306.
Melnick et al. (1994) *Nature* 370:373-375.
Merrifield (1969) *Adv Enzymol* 32:221-296.
Microcal Software (1998) *MicroCal ORIGIN™*, Micro-Cal Inc., Northhampton, Mass.
Mitchell et al. (1998) *Eur J Immunol* 28:1923-1933.
Mizoe et al. (1997) *J Surg Res* 73(2):160-165.
Myers & Jakoby (1975) *J Biol Chem* 250:3785-3789.
Nadeau et al. (1993) *J Biol Chem* 268:1479-1487.
Nair et al. (1999) *J Immunol* 162:6426-6432.
Natali et al. (1987) *Cancer* 59:55-63.
Navarro et al. (1991) *Virology* 184:253-264.
Nemoto et al.(1996) *J Biochem* 120:249-256.
Nicchitta (1998) *Curr Opin Immunol* 10:103-109.
Nieland et al. (1996) *Proc Natl Acad Sci USA* 93:6135-6139.
Norrby (1985) "Summary" in *Vaccines* 85, Lerner et al. (eds.), pp. 388-389, Cold Spring Harbor Press, Cold Spring Harbor, N.Y.
Obermann et al. (1998) *J Cell Biol* 143:901-910.
Ortmann et al. (1997) *Science* 277:1306-1309.
Palladino et al. (1987) *Cancer Res* 47:5074-5079.
Palleros et al. (1991) *Proc Natl Acad Sci USA* 88:5719-5723.
Panaretou et al. (1998) *EMBO J* 17:4829-4836.
Perez & Walker (1990) *J Immunol* 142:3662-3667.
Pratt (1998) *Proc Soc Exp Biol Med* 217:420-434.
Pratt et al. (1996) *Exs* 77:79-95.
Prodromou et al. (1999) *EMBO J* 18:754-762.
Prodromou et al. (1997) *Cell* 90:65-75.
Ramachandran & Gottlieb (1961) *Biochim Biophys Acta* 53:396-402.
Ramakrishnan et al. (1997) *J Cell Physiol* 170:115-29.
Riera et al. (1999) *Mol Cell Biochem* 191:97-104.
Robbins & Angell (1976) *Basic Pathology*, 2nd Ed., pp. 68-79, W. B. Saunders Co., Philadelphia, Penn.
Roe et al. (1999) *J Med Chem* 42:260-266.
Rose et al. (1987) *Biochemistry* 26:6583-6587.
Rosen & Weber (1969) *Biochemistry* 8:3915-3920.
Rotzsche et al. (1990) *Nature* 348:252-254.
Rotzsche et al. (1990) *Science* 249:283-287.
Sadasivan et al. (1996) *Cell* 5:103-114.
Sastry & Linderoth (1999) *J Biol Chem* 274:12023-12035.
Sato et al. (1995) *Clin Immunol Pathol* 74:35-43.
Schagger et al. (1994) *Anal Biochem* 217:220-230.
Schaiff et al. (1992) *J Exp Med* 176:657-666.
Scheibel & Buckner (1998) *Biochem Pharm* 56:675-82.
Scheibel et al. (1998) *Proc Natl Acad Sci USA* 95:1495-1499.
Scheibel et al. (1997) *J Biol Chem* 272:18608-18613.
Schild et al. (1999) *Curr Opin Immunol* 11:109-113.
Schnell et al. (1990) *Nature* 343:269-272.
Schroder et al. (1965) *The Peptides*, Vol. 1, Academic Press, New York, N.Y.
Schroder et al. (1965) *JAMA* 193:443.
Sciandra et al. (1984) *Proc Natl Acad Sci USA* 81:4843-4847.
Seale et al. (1998) *Methods Enzymol* 290:318-323.
Seip & Evans (1980) *J Clin Microbiol* 11:226-233.
Sharma et al. (1998) *J Biol Chem* 273:15474-15478.
Sharma et al. (1998) *Oncogene* 16:2639-2645.
Shi et al. (1994) *Biochemistry* 33:7536-7546.
Shirkey (1965) *JAMA* 193:443.
Smith et al. (1993) *J Biol Chem* 268:18365-18371.
Sriram et al. (1997) *Structure* 5:403-414.
Srivastava et al. (1986) *Proc Natl Acad Sci USA* 83:3407-3411.
Srivastava et al. (1998) *Immunity* 8:657-665.
Srivastava et al. (1994) *Immunogenetics* 39:93-98.
Stebbins et al. (1997) *Cell* 89:239-250.
Steinman (1991) *Annu Rev Immunol* 9:271-294.
Steward et al. (1969) *Solid Phase Peptide Synthesis*, W. H. Freeman Co., San Francisco, Calif.

Su et al. (1998) *J Mol Cell Cardiol* 30(3):587-598.
Sullivan et al. (1997) *J Biol Chem* 272:8007-8012.
Supino-Rosin et al. (2000) *J Biol Chem* 275(29):21850-21855.
Suto & Srivastava (1995) *Science* 269:1585-1588.
Tacchini et al. (1997) *Hepatology* 26(1):186-191.
Tailer et al. (1990) *Nuc Acids Res* 18(16):4928.
Takashi et al. (1977) *Proc Natl Acad Sci USA* 74:2334-2338.
Tamura et al. (1997) *Science* 278:117-120.
Toft (1998) *Trends Endocrinol Metab* 9:238-243.
Toggas et al. (1994) *Nature* 367:188-193.
Udono et al. (1994) *Proc Natl Acad Sci USA* 91:3077-81.
U.S. Pat. No. 4,244,946
U.S. Pat. No. 4,968,671
U.S. Pat. No. 5,066,578
U.S. Pat. No. 5,250,414
U.S. Pat. No. 5,352,660
U.S. Pat. No. 5,504,090
U.S. Pat. No. 5,645,999
U.S. Pat. No. 5,571,840
U.S. Pat. No. 5,733,916
U.S. Pat. No. 5,739,278
U.S. Pat. No. 5,747,332
U.S. Pat. No. 5,750,119
U.S. Pat. No. 5,756,492
U.S. Pat. No. 5,786,152
U.S. Pat. No. 5,830,464
U.S. Pat. No. 5,834,228
U.S. Pat. No. 5,837,251
U.S. Pat. No. 5,872,011
U.S. Pat. No. 5,898,066
U.S. Pat. No. 5,932,542
U.S. Pat. No. 6,017,965
U.S. Pat. No. 6,046,381
U.S. Pat. No. 6,080,730
Van Bleek et al. (1990) *Nature* 348:213-216.
Vijayasardahl et al. (1990) *J Exp Med* 171 (4):1375-1380.
Wearsch & Nicchitta (1996a) *Prot Express Purif* 7:114-121.
Wearsch & Nicchitta (1996b) *Biochemistry* 35:16760-16769.
Wearsch & Nicchitta (1997) *J Biol Chem* 272:5152-5156.
Wearsch et al. (1998) *Biochemistry* 37:5709-5719.
Weber (1991) *Adv Protein Chem* 41:1-36.
Weber & Farris (1979) *Biochemistry* 18:3075-3078.
WO 95/24923
WO 97/10000
WO 97/10002
WO 98/34641
WO 99/26966
WO 99/61585
Xiao et al. (1999) *J Neurochem* 72:95-101.
Yagita et al. (1999) *J Neurochem* 72:1544-1551.
Yamamoto et al. (1986) *Brain Res* 384:1-10.
Yamamoto et al. (1990) *Acta Neuropathol* 80:487-492.
Yu et al. (1991) *Cancer Res* 51 (2):468-475.
Zimmer et al. (1993) *Pertides*, pp. 393-394, ESCOM Science Publishers, B. V.

It will be understood that various details of the invention can be changed without departing from the scope of the invention. Furthermore, the foregoing description is for the purpose of illustration only, and not for the purpose of limitation—the invention being defined by the claims.

What is claimed is:

1. A method for purifying a complex comprising a GRP94 protein from a sample, the method comprising:
   (a) contacting a sample comprising a complex comprising a GRP94 protein with a binding agent comprising an adenosine moiety or structural mimetic thereof having a 5' substitution, wherein the binding agent preferentially binds GRP94, the binding agent immobilized to a solid phase support at the 5' substitution, to immobilize the complex to the solid phase support;
   (b) collecting the remaining sample; and
   (c) eluting the complex from the solid phase support to give purified complex in the eluate.

2. The method of claim 1, wherein the binding agent is free of ATP or ADP.

3. The method of claim 1, wherein the binding agent comprises a compound of formula (I):

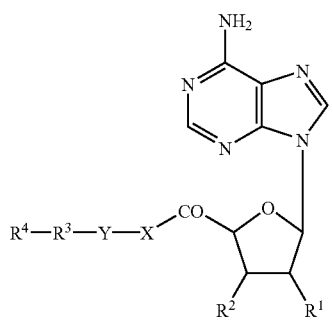

where:

X and Y together are:

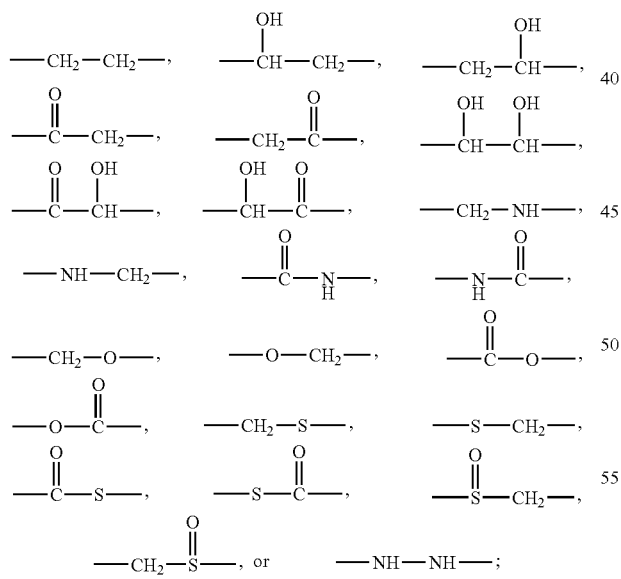

$R^1$ =hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^1$ is halo where halo is chloro, fluoro, bromo, or iodo;

$R^2$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^2$ is halo where halo is chloro, fluoro, bromo, or iodo; and $R^3$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^3$ is halo where halo is chloro, fluoro, bromo, or iodo.

4. The method of claim 1, wherein the complex further comprises an antigenic molecule.

5. The method of claim 1, wherein the complex is from a warm-blooded vertebrate.

6. The method of claim 5, wherein the complex is from a mammal.

7. The method of claim 6, wherein the mammal is selected from the group consisting of human, mouse, pig, rat, ape, monkey, cat, guinea pig, cow, goat, and horse.

8. The method of claim 1, wherein the complex is produced in vitro.

9. The method of claim 1, wherein the complex is purified from cancerous tissue.

10. The method of claim 9, wherein the complex is purified from cancerous tissue autologous to a vertebrate subject to be treated with the complex.

11. The method of claim 9, wherein the complex is purified from cancerous tissue from a second vertebrate subject that is the same type as a cancerous tissue present in a first vertebrate subject to be treated with the composition.

12. The method of claim 9, wherein the complex is obtained from a tumor cell line of a type of cancer.

13. The method of claim 9, wherein the cancerous tissue comprises a sarcoma or carcinoma, selected from the group consisting of fibrosarcoma, myxosarcoma, liposarcoma, chond rosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenströom's macroglobulinemia, and heavy chain disease.

14. The method of claim 1, wherein the complex is purified from a eukaryotic cell infected with a pathogen that causes an infectious disease.

15. The method of claim 14, wherein the infectious disease is caused by a pathogen selected from the group consisting of viruses, bacteria, fungi, protozoa, and parasites.

16. The method of claim 15, wherein the viral pathogen is selected from the group consisting of hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus (RSV), papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

17. The method of claim 15, wherein the bacterial pathogen is selected from the group consisting of *Mycobacteria, Rickettsia, Mycoplasma, Neisseria,* and *Legionella.*

18. The method of claim 15, wherein the protozoal pathogen is selected from the group consisting of *Leishmania, Kokzidioa, Trypanosoma, Chiamydia,* and *Rickettsia.*

19. The method of claim 1, wherein complex bound to the immobilized binding agent is eluted by washing the solid phase support with a buffer comprising the binding agent to give complex in the eluate.

20. A method for isolating an antigenic molecule associated with a GRP94 complex, the method comprising:
  (a) contacting a sample comprising a complex comprising a GRP94 protein and an antigenic molecule with a binding agent comprising an adenosine moiety or structural mimetic thereof having a 5' substitution, wherein the binding agent preferentially binds GRP94, the binding agent immobilized to a solid phase support at the 5' substitution, to immobilize the complex to the solid phase support;
  (b) collecting the remaining sample;
  (c) eluting the complex from the solid phase support to give purified complex in the eluate; and
  (d) isolating the antigenic molecule from the eluate.

21. The method of claim 20, wherein the binding agent is free of ATP or ADP.

22. The method of claim 20, wherein the complex comprising GRP94 and the antigenic molecule is from a warm-blooded vertebrate.

23. The method of claim 22, wherein the complex comprising GRP94 and the antigenic molecule is from a mammal.

24. The method of claim 23, wherein the mammal is selected from the group consisting of human, mouse, pig, rat, ape, monkey, cat, guinea pig, cow, goat, and horse.

25. The method of claim 20, wherein the complex comprising GRP94 and the antigenic molecule is produced in vitro.

26. The method of claim 20, wherein the antigenic molecule is an exogenous antigenic peptide.

27. The method of claim 20, wherein the antigenic molecule is a peptide with which the GRP94 complex is endogenously associated in vivo.

28. The method of claim 20, wherein the complex comprising GRP94 and the antigenic molecule is isolated from cancerous tissue.

29. The method of claim 28, wherein the complex comprising GRP94 and the antigenic molecule is isolated from cancerous tissue autologous to a vertebrate subject to be treated with the complex comprising GRP94 and the antigenic molecule.

30. The method of claim 28, wherein the complex comprising GRP94 and the antigenic molecule is isolated from cancerous tissue from a second vertebrate subject that is the same type as a cancerous tissue present in a first vertebrate subject to be treated with the complex comprising GRP94 and the antigenic molecule.

31. The method of claim 28, wherein the complex comprising GRP94 and the antigenic molecule is obtained from a tumor cell line of a type of cancer.

32. The method of claim 28, wherein the cancerous tissue comprises a sarcoma or carcinoma, selected from the group consisting of fibrosarcoma, myxosarcoma, liposarcoma, chond rosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenströom's macroglobulinemia, and heavy chain disease.

33. The method of claim 20, wherein the antigenic molecule is an antigenic peptide that is present in a eukaryotic cell infected with a pathogen which causes said infectious disease but not present in said eukaryotic cell when said eukaryotic cell is not infected with said pathogen.

34. The method of claim 33, wherein said infectious disease is caused by a pathogen selected from the group consisting of viruses, bacteria, fungi, protozoa, and parasites.

35. The method of claim 34, wherein said viral pathogen is selected from the group consisting of hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus (RSV), papilloma virus, papaya virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-I).

36. The method of claim 34, wherein said bacterial pathogen is selected from the group consisting of *Mycobacteria, Mycoplasma, Neisseria*, and *Legionella*.

37. The method of claim 34, wherein said protozoal pathogen is selected from the group consisting of *Leishmania, Kokzidioa, Trypanosoma, Chiamydia*, and *Rickettsia*.

38. The method of claim 20, wherein the binding agent comprises a compound of formula (I):

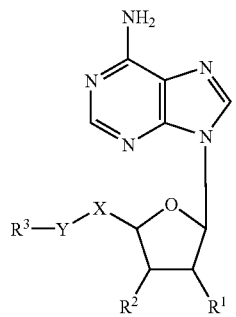

where:

X and Y together are:

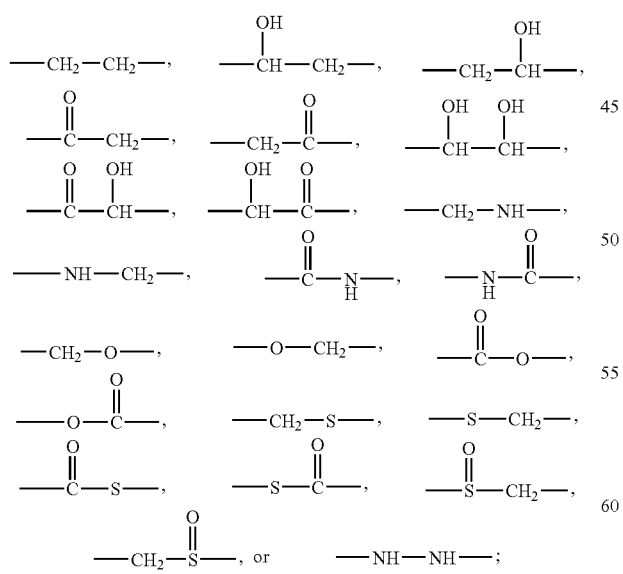

$R^1$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arlyester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^1$ is halo where halo is chloro, fluoro, bromo, or iodo;

$R^2$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arlyester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^2$ is halo where halo is chloro, fluoro, bromo, or iodo; and $R^3$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arlyester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^3$ is halo where halo is chloro, fluoro, bromo, or iodo.

39. The method of claim 20, wherein complex bound to the immobilized binding agent is eluted by washing the solid phase support with a buffer comprising the binding agent to give complex in the eluate.

40. The method of claim 1, wherein the binding agent comprises a compound of formula (II):

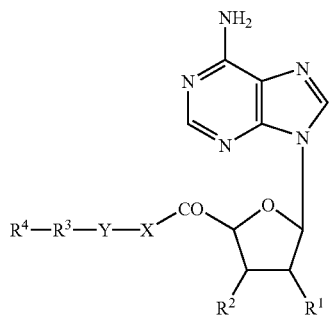

where:

X and Y together are:

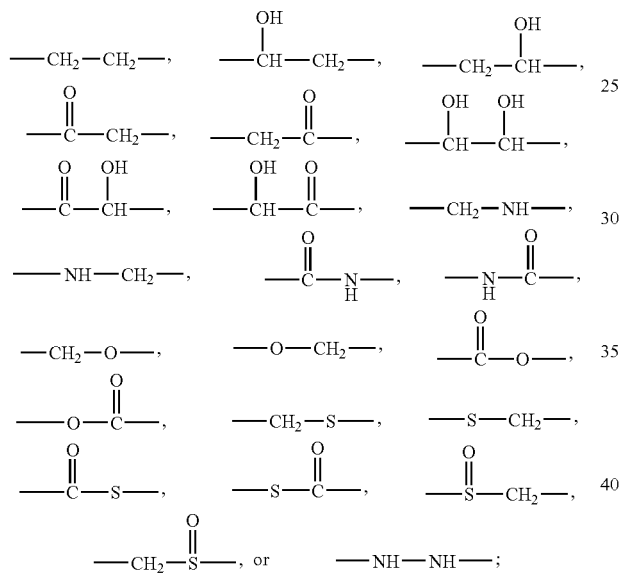

$R^1$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^1$ is halo where halo is chloro, fluoro, bromo, or iodo;

$R^2$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^2$ is halo where halo is chloro, fluoro, bromo, or iodo;

$R^3$=$C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; and $R^4$=$C_1$ to $C_6$ alkyl, $C_1$ to $C_6$ branched alkyl, $C_4$ to $C_8$ cycloalkyl with or without O, N or S in the ring, $C_1$ to $C_6$ alkenyl, branched $C_1$ to $C_6$ alkenyl, $C_4$ to $C_8$ cycloalkenyl with or without O, N or S in the ring, $C_4$ to $C_8$ aroyl, $C_4$ to $C_8$ aryl, $C_4$ to $C_{12}$ heterocyclic or heteropolycyclic alkyl or aryl with O, N or S in the ring, $C_4$ to $C_8$ aryl-substituted $C_1$ to $C_6$ alkyl, alkyl-substituted or aryl-substituted $C_4$ to $C_{12}$ heterocyclic or heteropolycyclic alkyl or aryl with O, N or S in the ring, alkyl-substituted $C_4$ to $C_8$ aroyl, or alkyl-substituted $C_4$ to $C_8$ aryl; or hydroxyl-, amino-, or halo-substituted versions thereof where halo is chloro, bromo, fluoro or iodo.

41. The method of claim 20, wherein the binding agent comprises a compound of formula (II):

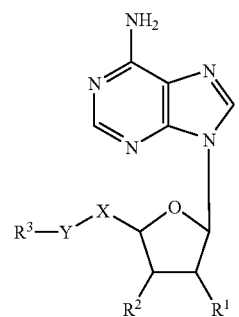

where:

X and Y together are:

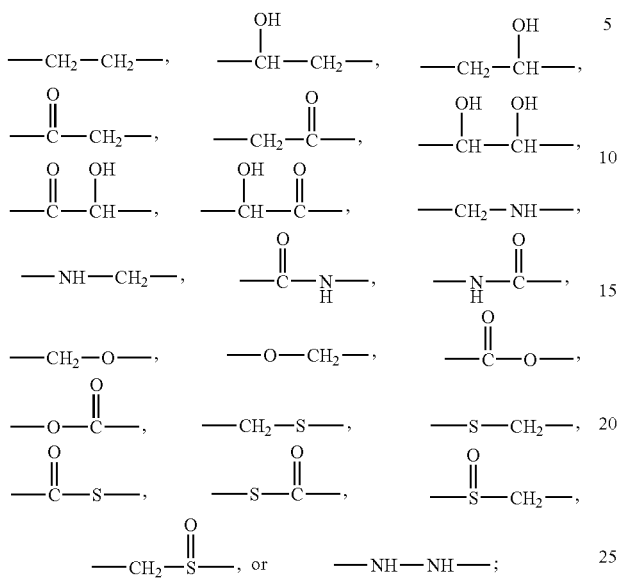

$R^1$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyf, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^1$ is halo where halo is chloro, fluoro, bromo, or iodo;

$R^2$=hydrogen, hydroxyl, $C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; or $R^2$ is halo where halo is chloro, fluoro, bromo, or iodo;

$R^3$=$C_1$ to $C_6$ alkyl, $C_1$ to $C_6$ branched alkyl, $C_1$ to $C_6$ hydroxyalkyl, branched $C_1$ to $C_6$ hydroxyalkyl, $C_4$ to $C_8$ cycloalkyl, $C_1$ to $C_6$ alkenyl, branched $C_1$ to $C_6$ alkenyl, $C_4$ to $C_8$ cycloalkenyl, $C_4$ to $C_8$ aryl, $C_4$ to $C_8$ aroyl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, primary, secondary or tertiary $C_1$ to $C_6$ alkylamino, primary, secondary or tertiary branched $C_1$ to $C_6$ alkylamino, primary, secondary or tertiary cycloalkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ arylcarboxylic acid, $C_4$ to $C_8$ arylester, $C_4$ to $C_8$ aryl substituted $C_1$ to $C_6$ alkyl, $C_4$ to $C_{12}$ heterocyclic or heteropolycyclic alkyl or aryl with O, N or S in the ring, alkyl-substituted or aryl-substituted $C_4$ to $C_{12}$ heterocyclic or heteropolycyclic alkyl or aryl with O, N or S in the ring; or hydroxyl-, amino-, or halo-substituted versions thereof; and $R^4$=$C_1$ to $C_6$ alkyl, $C_1$ to $C_6$ branched alkyl, $C_4$ to $C_8$ cycloalkyl with or without O, N or S in the ring, $C_1$ to $C_6$ alkenyl, branched $C_1$ to $C_6$ alkenyl, $C_4$ to $C_8$ cycloalkenyl with or without O, N or S in the ring, $C_4$ to $C_8$ aroyl, $C_4$ to $C_8$ aryl, $C_4$ to $C_{12}$ heterocyclic or heteropolycyclic alkyl or aryl with O, N or S in the ring, $C_4$ to $C_8$ aryl-substituted $C_1$ to $C_6$ alkyl, alkyl-substituted or aryl-substituted $C_4$ to $C_{12}$ heterocyclic or heteropolycyclic alkyl or aryl with O, N or S in the ring, alkyl-substituted $C_4$ to $C_8$ aroyl, or alkyl-substituted $C_4$ to $C_8$ aryl; or hydroxyl-, amino-, or halo-substituted versions thereof where halo is chloro, bromo, fluoro or iodo.

* * * * *

UNITED STATES PATENT AND TRADEMARK OFFICE
CERTIFICATE OF CORRECTION

| | | |
|---|---|---|
| PATENT NO. | : 7,598,355 B2 | Page 1 of 1 |
| APPLICATION NO. | : 10/210333 | |
| DATED | : October 6, 2009 | |
| INVENTOR(S) | : Nicchitta et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1087 days.

Signed and Sealed this

Twenty-eighth Day of September, 2010

David J. Kappos
*Director of the United States Patent and Trademark Office*